US007180600B2

(12) United States Patent
Horii et al.

(10) Patent No.: US 7,180,600 B2
(45) Date of Patent: Feb. 20, 2007

(54) OPTICAL IMAGING APPARATUS

(75) Inventors: Akihiro Horii, Hachioji (JP); Hitoshi Ueno, Hachioji (JP); Shuhei Iizuka, Hachioji (JP); Hitoshi Mizuno, Koganei (JP); Tadashi Hirata, Hachioji (JP)

(73) Assignee: Olympus Corporation, Tokyo (JP)

( * ) Notice: Subject to any disclaimer, the term of this patent is extended or adjusted under 35 U.S.C. 154(b) by 157 days.

(21) Appl. No.: 10/874,573

(22) Filed: Jun. 24, 2004

(65) Prior Publication Data

US 2005/0168751 A1    Aug. 4, 2005

Related U.S. Application Data

(63) Continuation of application No. 09/398,366, filed on Sep. 17, 1999, now abandoned.

(30) Foreign Application Priority Data

| Sep. 21, 1998 | (JP) | 10-266752 |
| Sep. 21, 1998 | (JP) | 10-266753 |
| Oct. 22, 1998 | (JP) | 10-301306 |
| Jun. 7, 1999  | (JP) | 11-159270 |

(51) Int. Cl.
*G01B 9/02* (2006.01)
*A61B 6/00* (2006.01)

(52) U.S. Cl. ........................... 356/479; 600/478
(58) Field of Classification Search ............... 356/477, 356/479, 497; 250/227.19, 227.27; 385/12; 600/478

See application file for complete search history.

(56) References Cited

U.S. PATENT DOCUMENTS

| 5,321,501 A | 6/1994  | Swanson et al. |
| 5,383,467 A | 1/1995  | Aner et al.    |
| 5,872,879 A | 2/1999  | Hamm           |
| 6,069,698 A | 5/2000  | Ozawa et al.   |
| 6,134,003 A | 10/2000 | Tearney et al. |

FOREIGN PATENT DOCUMENTS

| JP | 411056786 A | * | 3/1999 |
| JP | 11-148897   |   | 6/1999 |
| WO | WO 97/32182 |   | 9/1997 |

OTHER PUBLICATIONS

Tearney, G.J., et al., "Rapid Acquisition of InVivo Biological Images by Use of Optical Coherence Tomography," Optics Letters, vol. 21 (No. 17), p. 1408-1410, (Sep. 1, 1996).
Tearney, G.J. et al., "In Vivo Endoscopic Optical Biopsy with Optical Coherence Tomography," Science, p. 2037-2039, (Jun. 27, 1997).

* cited by examiner

*Primary Examiner*—Gregory J. Toatley, Jr.
*Assistant Examiner*—Patrick Connolly
(74) *Attorney, Agent, or Firm*—Pillsbury Winthrop Shaw Pittman, LLP

(57) ABSTRACT

An optical imaging apparatus has an optical scanning probe configured to irradiate low-coherence light onto a subject and to perform photo-reception of light scattered at the subject, and an observation device adapted to construct a cross-section image of the subject based on information from the light received through the optical scanning probe. The optical scanning probe is detachably connected to the observation device.

7 Claims, 44 Drawing Sheets

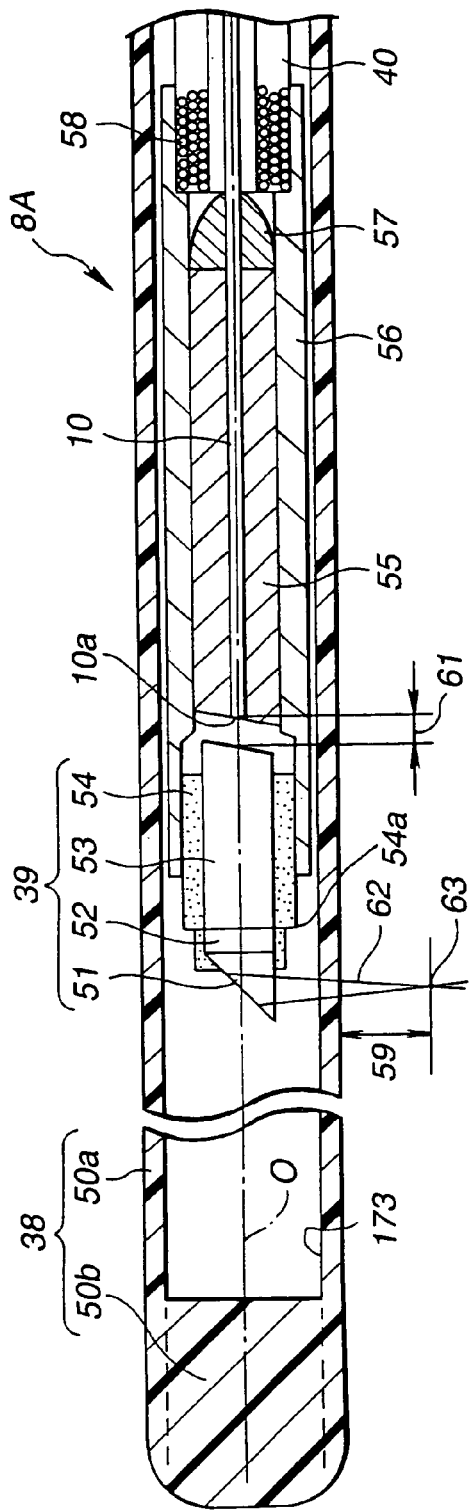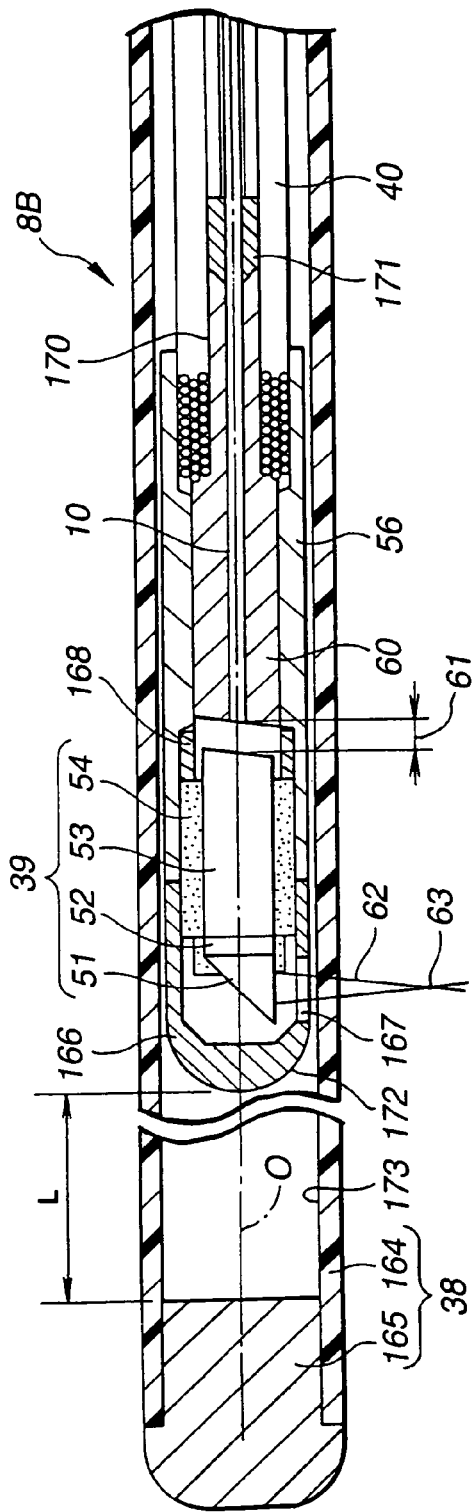

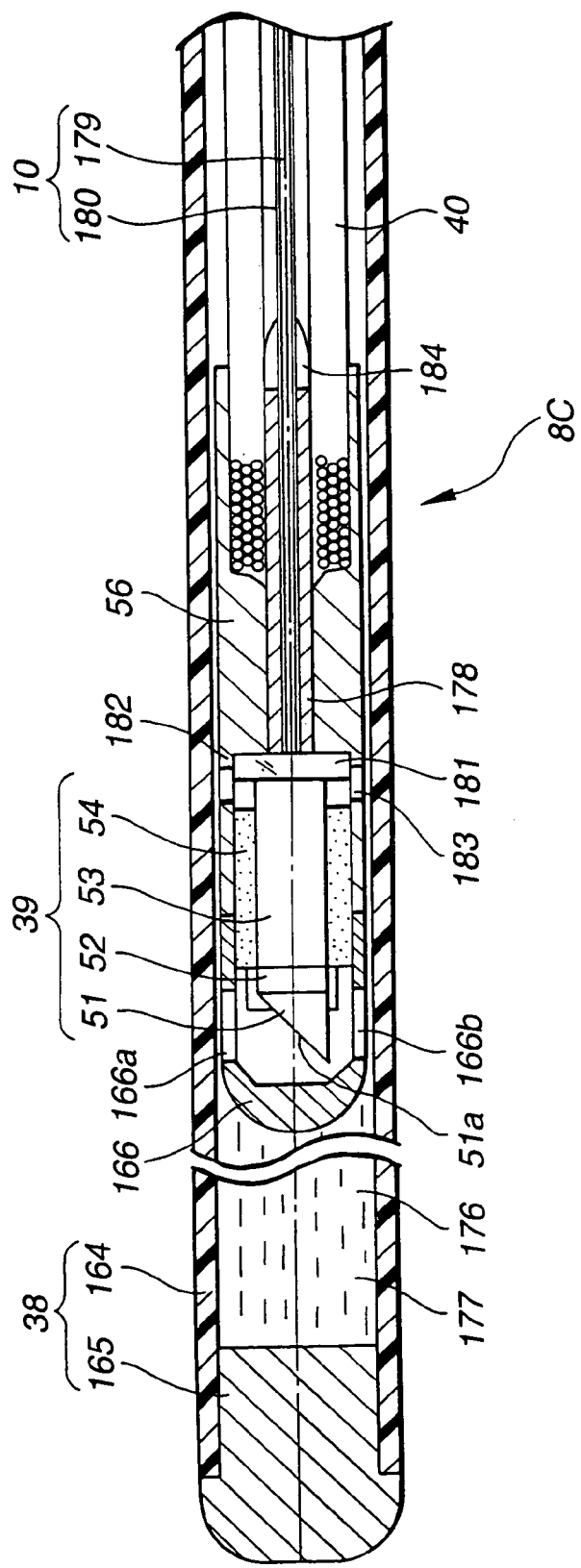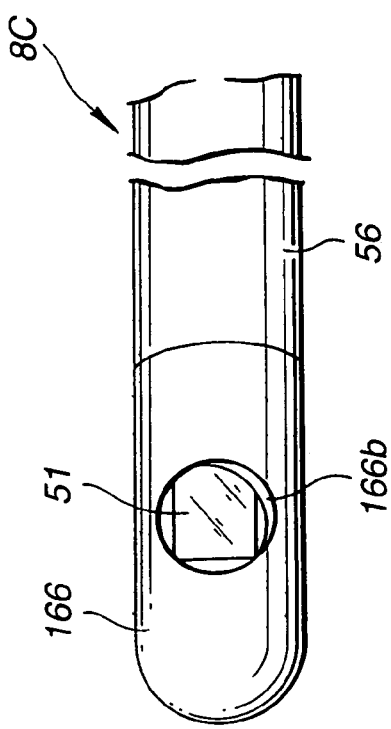
FIG.18A
FIG.18B

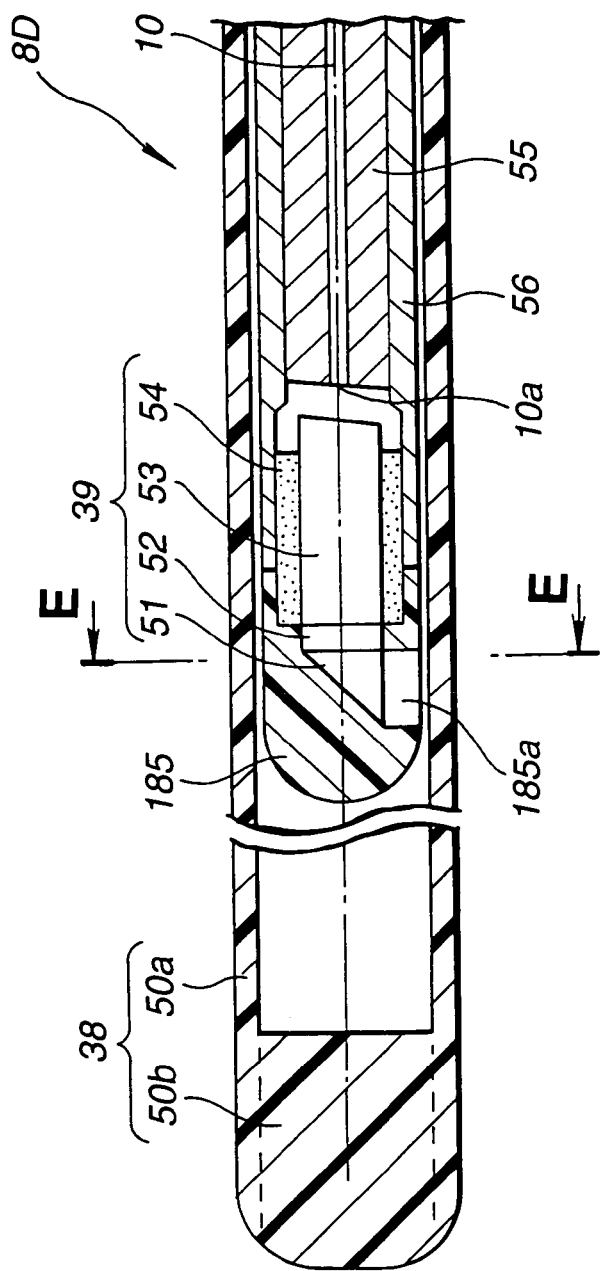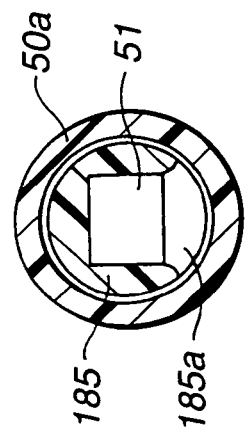

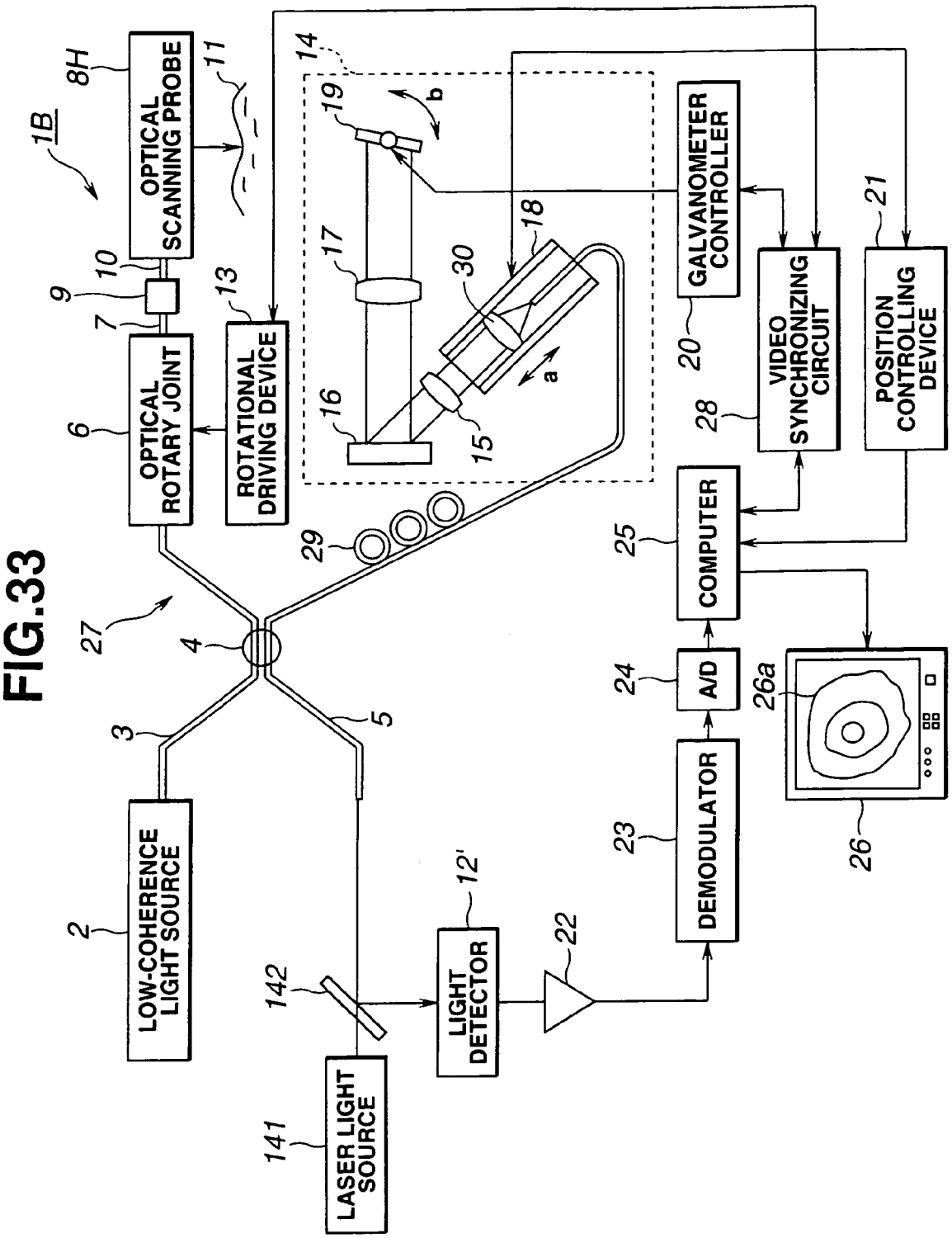

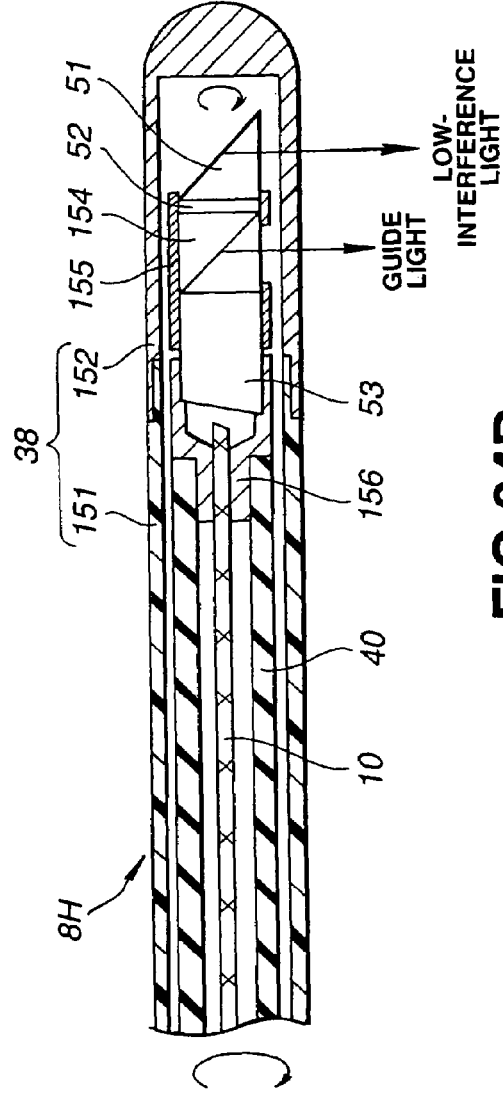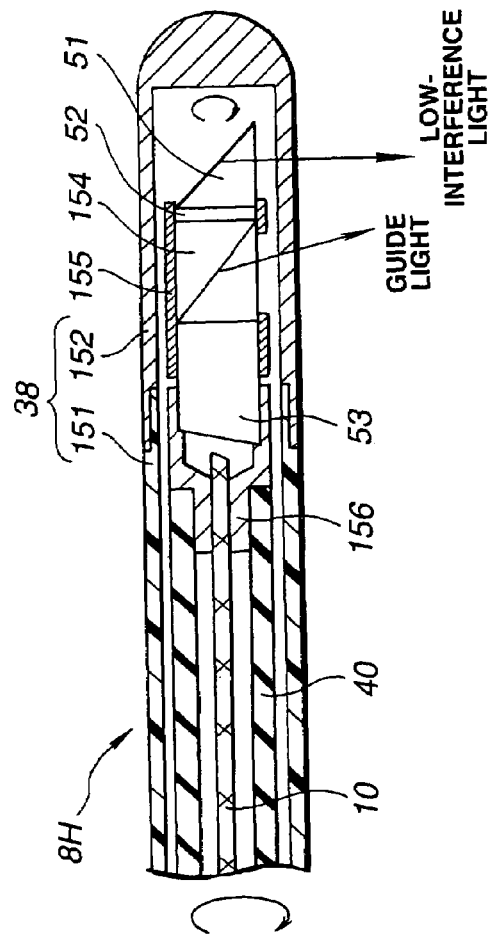

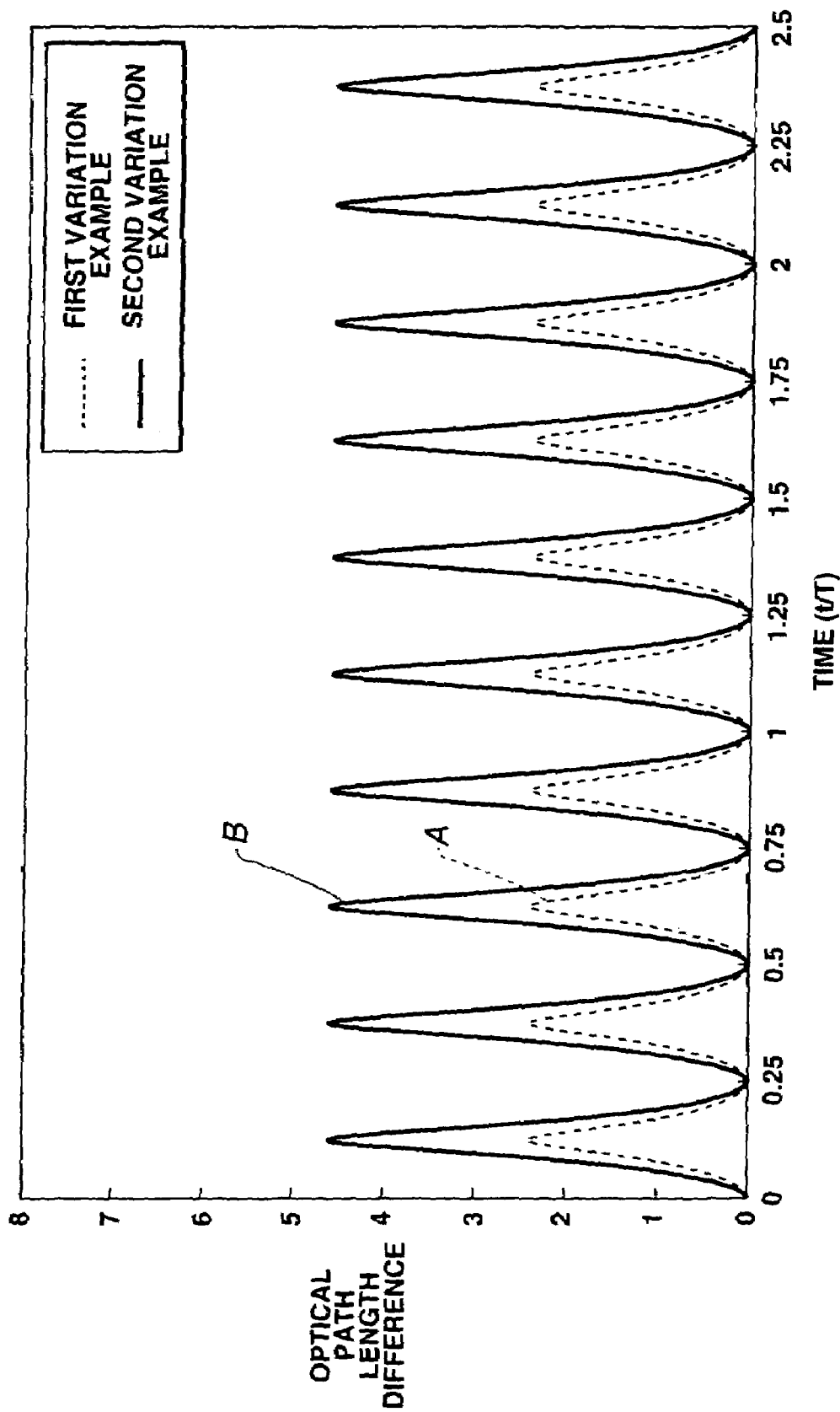

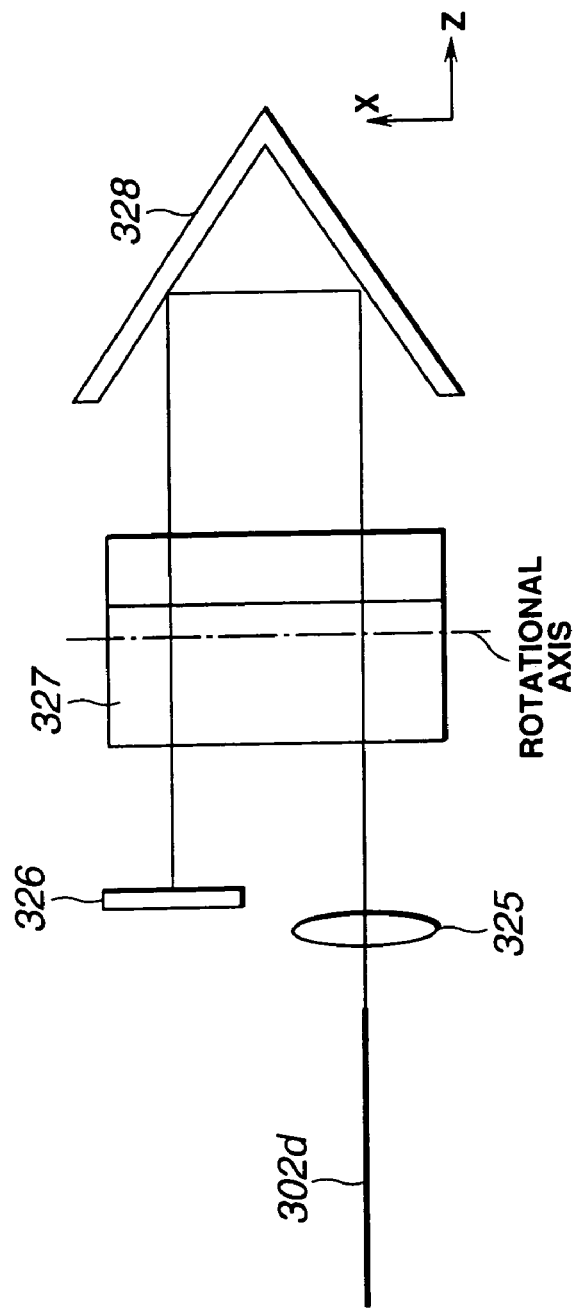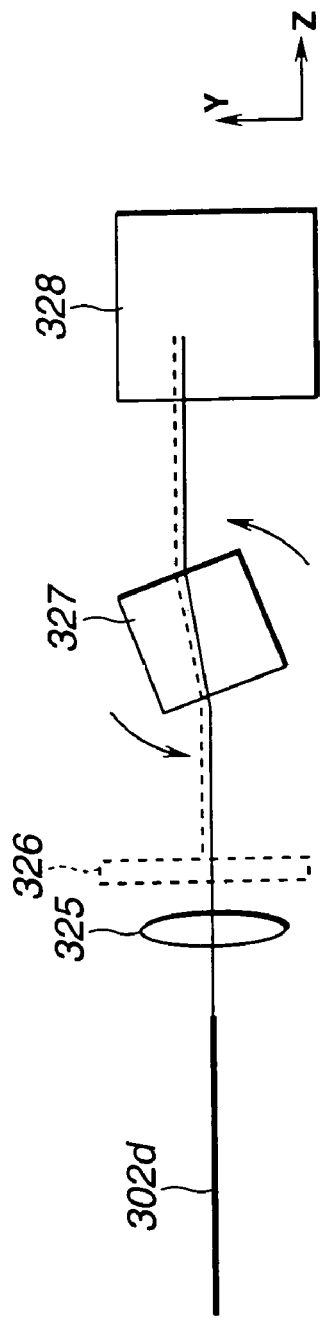

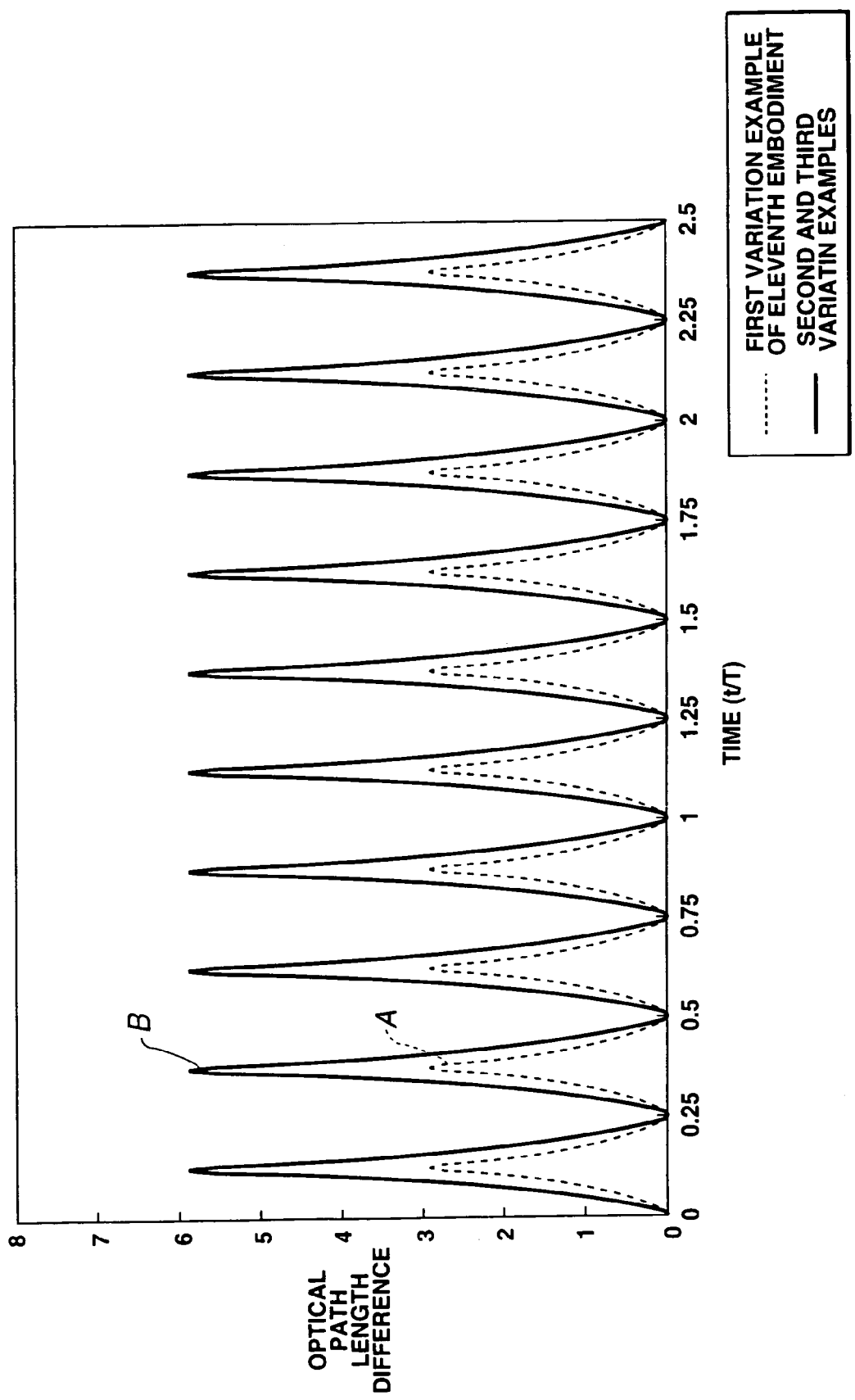

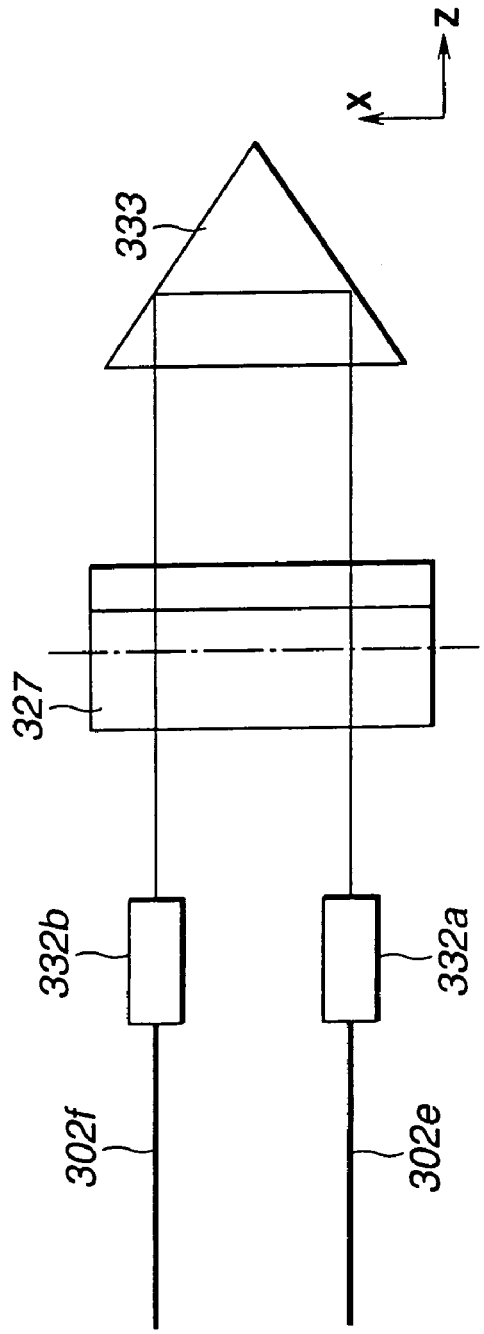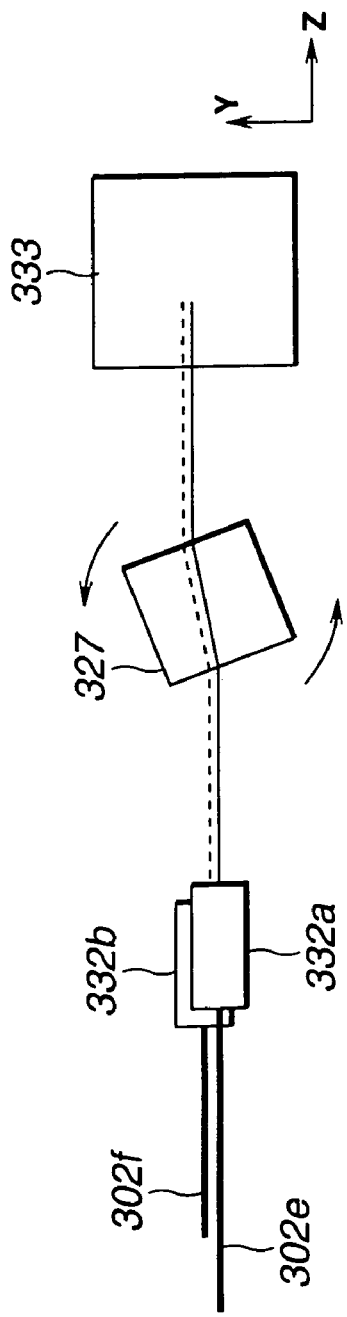

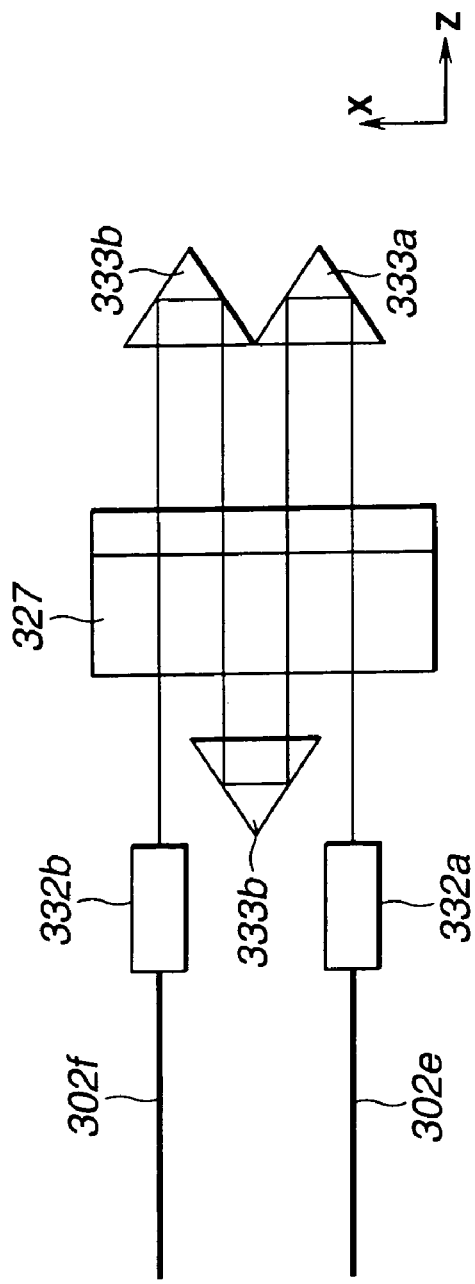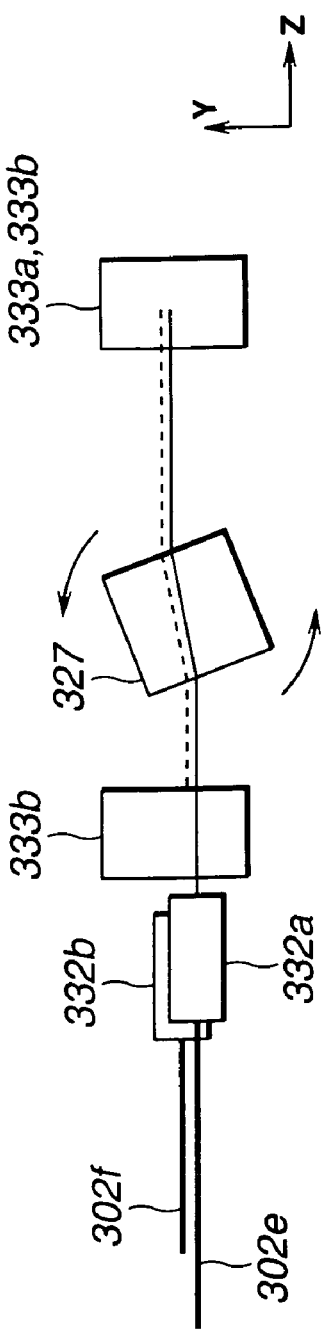
FIG.48A
FIG.48B

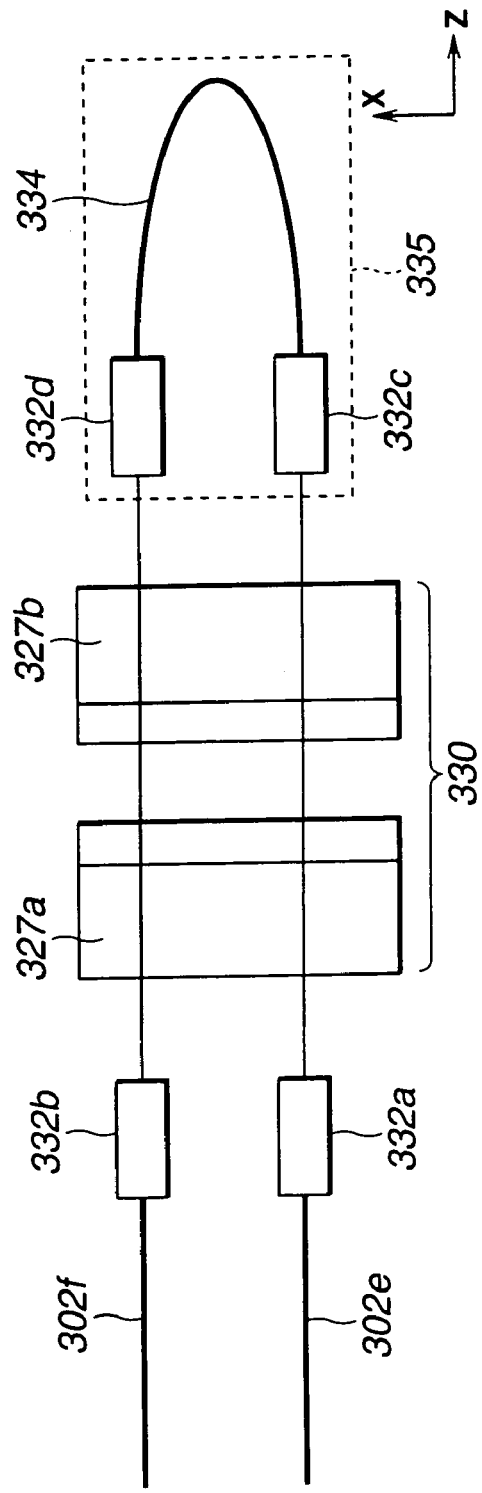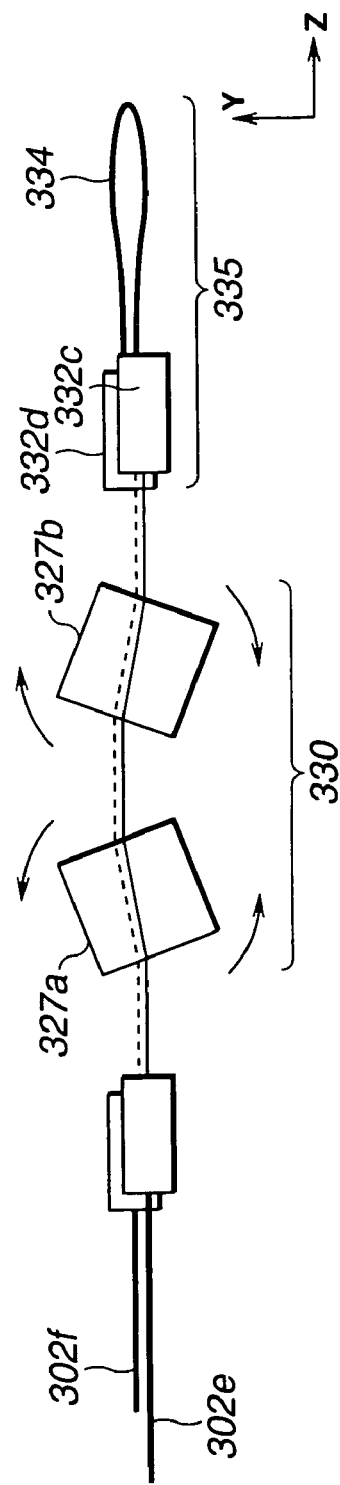

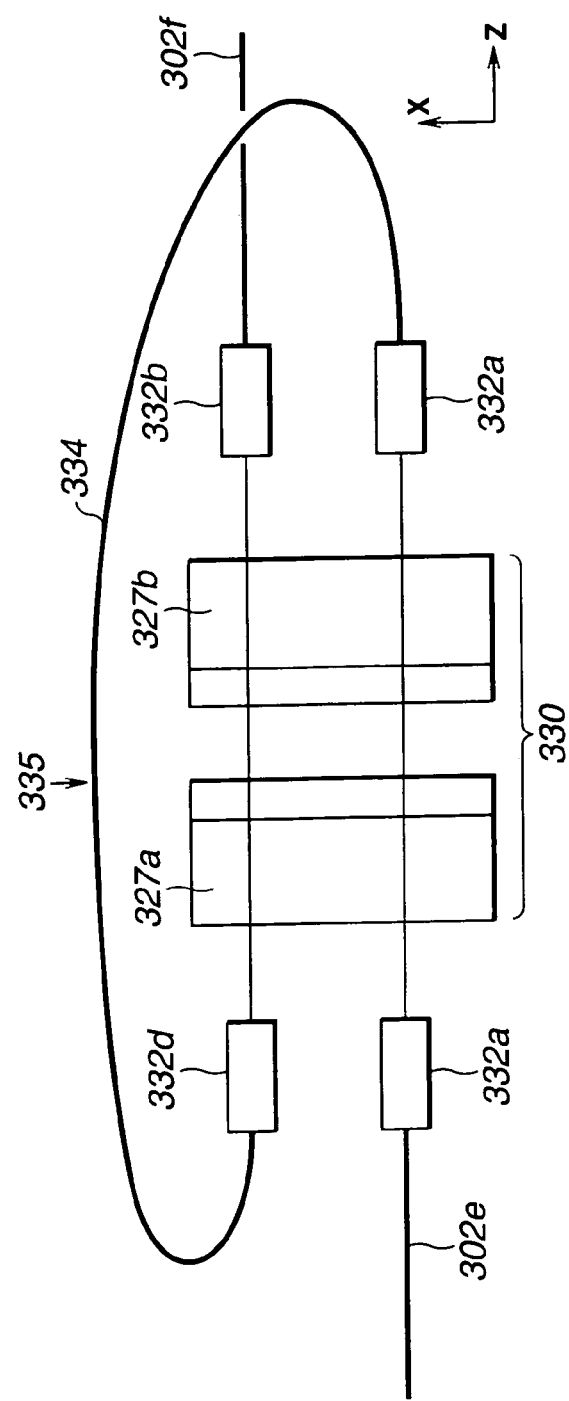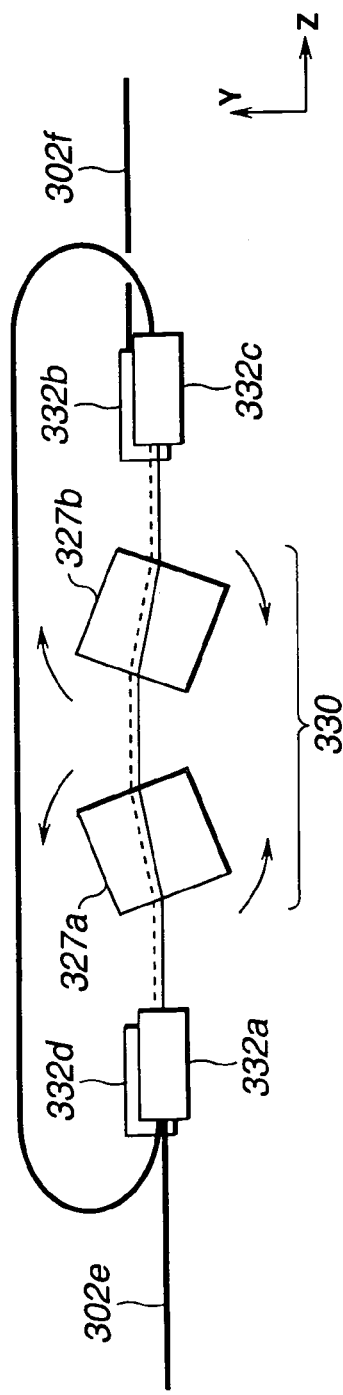

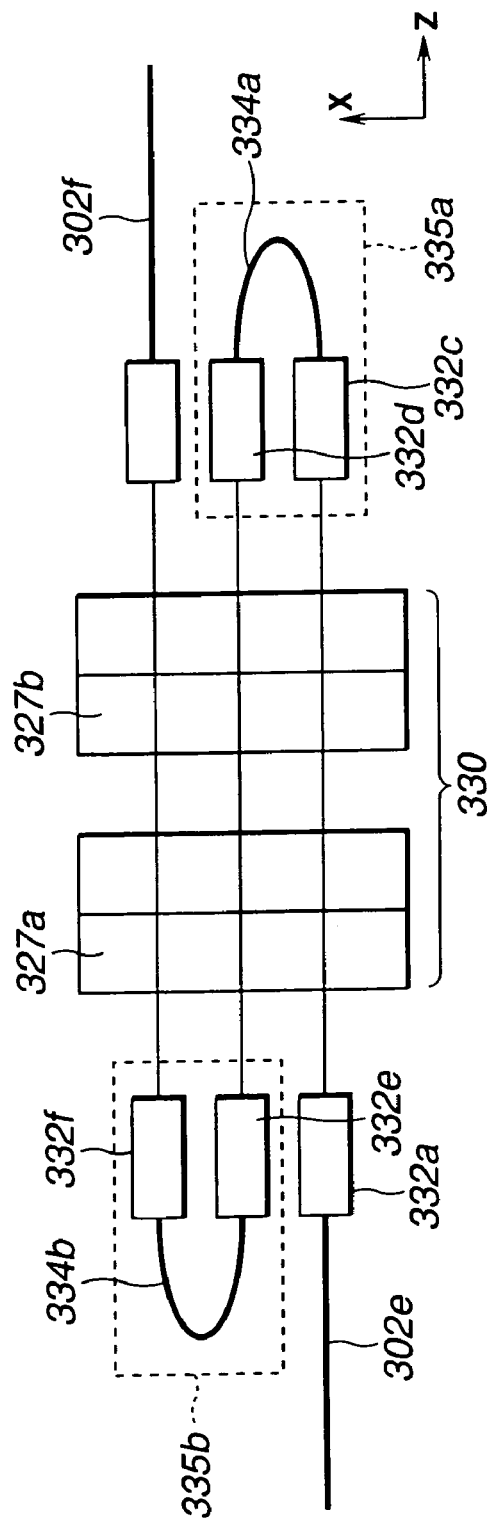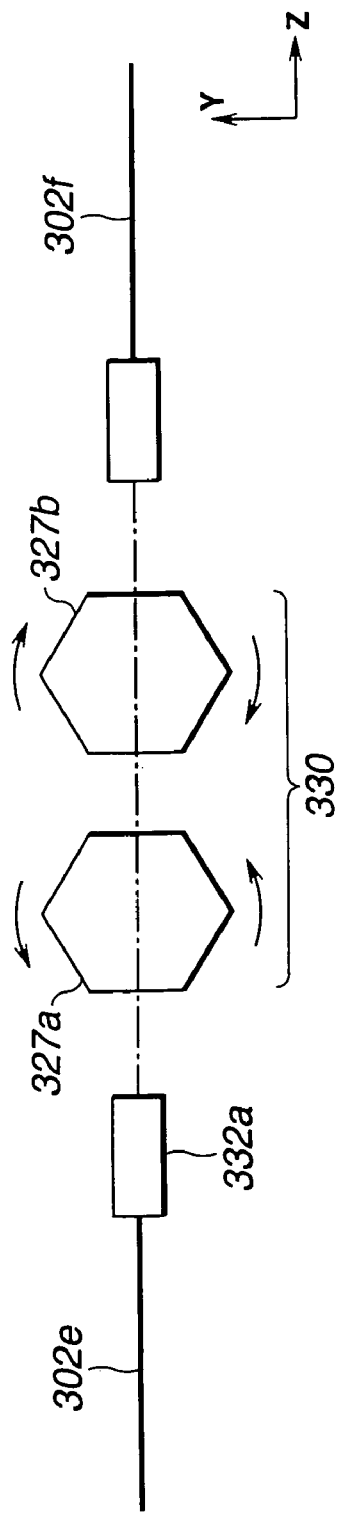

OPTICAL IMAGING APPARATUS

This is a continuation of U.S. patent application Ser. No. 09/398,366, filed on Sep. 17, 1999, now abandoned the contents of which are incorporated herein by reference in their entirety.

BACKGROUND OF THE INVENTION

1. Field of the Invention

The present invention relates to an optical imaging apparatus which irradiates low-coherence light onto a subject and constructs a cross-section image of the subject based on information from the light scattered at the subject.

2. Description of the Related Art

In recent years, an interference-type OCT (optical coherence tomography) apparatus capable of obtaining cross-sectional images of a subject using low-coherence light has been proposed as an apparatus capable of obtaining optical information within tissue of an organism being diagnosed, such as disclosed in WO92/19930 (U.S. Pat. No. 5,321,501), for example.

This WO92/19930 discloses a probe provided with a rotating tube provided with an optical element and optical element inside an outer tube-shaped sheath for insertion into the body cavity. However, no probe detaching means is provided, so scrubbing and sterilization necessary for use in the body cavity cannot be performed. Also, the optical element such as the prism at the tip end is exposed from the external sheath and rotates in that state, so there is the possibility that the organism may be damaged.

Also, Japanese Unexamined Patent Publication No.11-148897 discloses an optical probe for OCT wherein the optical probe portion and the observation apparatus portion are detachable. A detachable connector portion is provided, and the optical element such as the prism at the tip end is covered and sealed with a transparent sheath.

However, according to this art, rotational force is not transmitted smoothly unless the rotational shaft of the rotation transmitting means for rotating the rotating tube provided within the connector portion of the optical probe, and the rotational shaft of the rotation driving means provided in the observation apparatus are precisely matched, resulting in irregularities and instability in the rotating speed, but in practice, it is difficult to match the two rotational shafts in a precise manner.

Further, the rotation transmitting means at the base portion of the rotating tube and the optical fiber connecting member are formed integrally, so in the event that any inclination occurs between the two, or in the event that slack occurs in the bearing supporting the rotating shafts so as to move in the direction of the fiber, the connection of the optical fiber of the optical probe and the optical fiber of the observation apparatus becomes unstable, which has been a problem.

Particularly, in the case of the single mode fiber used for OCT, there is the need to abut the fiber cores at a precision in the order of several µm, so even slight shifting or a slight gap at the fiber ends results in massive loss of light, deterioration in the observation S/N ratio, and irregularities in the intensity of the observed image due to change in the connection state owing to rotation.

SUMMARY OF THE INVENTION

Accordingly, it is a first object of the present invention to provide an optical imaging apparatus, wherein a stable connection can be secured between the optical fiber of the optical scanning probe and the optical fiber of the observation apparatus, even in the event that shifting of the shafts, inclination in the angle, and slack in the shaft direction occur at the connector portion between the rotating shaft of the rotation transmitting means provided to the optical scanning probe and the rotating shaft of the rotation driving means provided to the observation apparatus.

It is a second object of the present invention to provide an optical imaging apparatus wherein optical connection can be easily made without re-polishing, even in the event that the fiber end at the observation apparatus side to be optically connected to the fiber end portion of the optical scanning probe is soiled.

It is a third object of the present invention to provide an optical imaging apparatus wherein the optical scanning probe can be easily attached to the observation apparatus.

It is a fourth object of the present invention to provide an optical imaging apparatus provided with a variable-length optical path mechanism capable of high-speed scanning over a wide range.

To this end, an optical imaging apparatus, which has an optical scanning probe which irradiates low-coherence light onto a subject and performs photo-reception of the light scattered at the subject, and an observation device for constructing a cross-section image of the subject, based on information from the light received through the optical scanning probe, with the optical scanning probe detachably connected thereto, comprises:

an optical scanning probe comprising:

a sheath, the greater portion thereof being formed of a flexible resin tube with at least the tip thereof being formed of a material with good light transmittance;

a mounting/detaching means for mounting housing provided to the base end of the sheath to the observation device housing;

a pipe member provided rotatably within the sheath, around the longitudinal axis thereof;

a rotational force transmitting means provided to the base portion of the pipe member;

a rotation holding means for holding the rotational force transmitting means rotatably to the housing;

fiber comprised of single mode fiber provided within the pipe member, with the tip portion thereof being fixed to the tip of the pipe member, such that the light cast from a low-coherence light source is cast into the base end thereof;

a lens for converging light cast from the fiber provided to the fiber tip; and a cast light path changing means fixed to the lens for changing the optical path of the cast light;

a fiber end fixing means provided to the base end of the fiber; and an elastic means provided between the fiber end fixing means and the rotational force transmitting means; and an observation device, comprising;

a rotational driving device for providing rotational force to the rotational force transmitting member of the optical probe; and an optical connecting means for connecting the fiber for sending and receiving observation light, provided to the single mode fiber of the optical probe of the observation device.

The configuration is such that, at the time of connecting the optical scanning probe and the observation device by the mounting/detaching means, the fiber end fixing means comes into close contact with the optical connecting means due to elastic means of the optical probe, so as to be optically connected, so that the fiber end for the optical scanning probe rotates while being pressed against the fiber end of the observation apparatus, such that both fiber ends are connected in a stable manner regardless of shifting of the shafts, inclination in the angle, and slack in the shaft direction occurring with the rotating shaft of the rotation transmitting member and the rotating shaft of the rotation driving device provided to the observation apparatus.

BRIEF DESCRIPTION OF THE DRAWINGS

FIGS. 1 through 7B relate to a first embodiment of the present invention, with FIG. 1 being a configuration diagram of an optical imaging apparatus according to the first embodiment;

FIG. 2 is a diagram illustrating the endoscope through which the optical scanning probe is inserted, shown together with the optical scanning probe;

FIG. 3 is a cross-sectional diagram illustrating the configuration of the rotation driving device and the optical scanning probe;

FIG. 4 is a cross-sectional diagram illustrating the detailed configuration of the optical scanning probe;

FIG. 5 is a cross-sectional diagram illustrating the configuration of the connection portion between the connector portion and the rotation driving device;

FIGS. 7A and 7B are cross-sectional diagrams respectively illustrating the state of the connector portion when being washed and when being stored;

FIG. 8B is a diagram illustrating the cross-section along C—C in FIG. 8A;

FIG. 10 is a diagram illustrating the cross-section along D—D in FIG. 9;

FIGS. 13A through 15B relate to a fifth embodiment of the present invention, FIGS. 13A through 13D being diagrams illustrating the relation between the scanning timing in the depth direction by the optical scanning means and the rotational angle of the optical scanning probe;

FIG. 14 is a block diagram illustrating the configuration of the principal members of the means for correcting irregularities in speed of the scanning of the optical scanning probe in the rotating direction, and displaying an observed image;

FIGS. 15A and 15B are explanatory diagrams for describing the scanning method in a variation example;

FIGS. 16 through 21 relate to a sixth embodiment of the present invention, FIG. 16 being a cross-sectional diagram illustrating the configuration of the tip side of the optical scanning probe;

FIG. 17 is a diagram illustrating the configuration of the tip side of the optical scanning probe according to a first variation example;

FIGS. 18A and 18B are diagrams illustrating the configuration of the tip side of the optical scanning probe according to a second variation example;

FIGS. 19A and 19B are diagrams illustrating the configuration of the tip side of the optical scanning probe according to a third variation example;

FIG. 21 is a cross-sectional diagram illustrating a detailed configuration of the connector portion;

FIGS. 23 through 33 related to an eighth embodiment of the present invention, FIG. 23 being a diagram illustrating the configuration of the variable-length optical path mechanism in the optical imaging apparatus according to the eighth embodiment;

FIG. 24 is a diagram illustrating the configuration of the variable-length optical path mechanism according to a variation example;

FIG. 26 is a flowchart illustrating the procedures for determining the optical path length for the center of the image;

FIG. 27 is a diagram illustrating the state of calibration equipment positioned to the tip side of the optical scanning probe;

FIG. 28 is a flowchart illustrating the procedures for determining the length of the optical path for the center of the image, by using reflection information from the calibration equipment;

FIG. 29 is a diagram illustrating the tip side of an optical scanning probe which scans in the horizontal direction;

FIG. 30 is a diagram illustrating an OCT image obtained using the optical scanning probe shown in FIG. 29;

FIG. 31 is a diagram illustrating the tip side of an optical scanning probe which scans the front linearly;

FIG. 32 is a diagram illustrating an OCT image obtained using the optical scanning probe shown in FIG. 31;

FIGS. 33 through 34B relate to a ninth embodiment of the present invention, with FIG. 33 being a configuration diagram of an optical imaging apparatus according to the ninth embodiment;

FIGS. 34A and 34B are cross-sectional diagrams illustrating the configuration of the tip side of the optical scanning probe;

FIG. 36 is a second explanatory diagram for describing the principle for the variable-length optical path optical system;

FIG. 37 is a diagram illustrating the specific configuration for canceling light ray shifting;

FIG. 38 is a configuration diagram illustrating the optical imaging apparatus according to a tenth embodiment of the present invention;

FIG. 39 is a configuration diagram of the variable-length optical path optical system;

FIG. 40 is a diagram illustrating time-change of the optical path length;

FIG. 42 is a diagram illustrating time-change of the optical path length in first and second variation examples;

FIGS. 43A and 43B are configuration diagrams illustrating the variable-length optical path optical system acquiring to a second variation example;

FIG. 46 is a diagram illustrating time-change of the optical path length in the eleventh embodiment through the third variation example thereof;

FIGS. 47A and 47B are configuration diagrams illustrating the variable-length optical path optical system acquiring to a first variation example of the eleventh embodiment;

FIGS. 48A and 48B are configuration diagrams illustrating the variable-length optical path optical system acquiring to a second variation example;

FIGS. 49A and 49B are configuration diagrams illustrating the variable-length optical path optical system acquiring to a third variation example;

FIGS. 50A and 50B are configuration diagrams illustrating the variable-length optical path optical system acquiring to a fourth variation example;

FIGS. 51A and 51B are configuration diagrams illustrating the variable-length optical path optical system acquiring to a fifth variation example;

DETAILED DESCRIPTION OF THE PREFERRED EMBODIMENTS

The first embodiment of the present invention will now be described with reference to FIG. 1 through FIG. 7B.

An object of the present embodiment is to prevent shifting of the shafts, inclination in the angle, and slack in the shaft direction from occurring between the rotating shaft of the rotation transmitting means provided to the optical scanning probe and the rotating shaft of the rotation driving means provided to the observation apparatus, and to secure a stable connection between the optical fiber of the optical probe and the optical fiber of the observation apparatus.

Also, another object is to secure a good optical connection by allowing the detachable single mode fiber provided to the connection portion of the observation apparatus and optical probe to be replaced without re-polishing even in the event that the fiber end at the observation apparatus side to be optically connected to the fiber end portion of the optical scanning probe is soiled.

Further, another object is to connect rotational force transmission and also connect optical connecting means with a single attaching action of the connector portion to the observation apparatus, thereby providing an apparatus which is easy to use.

Figure 1:
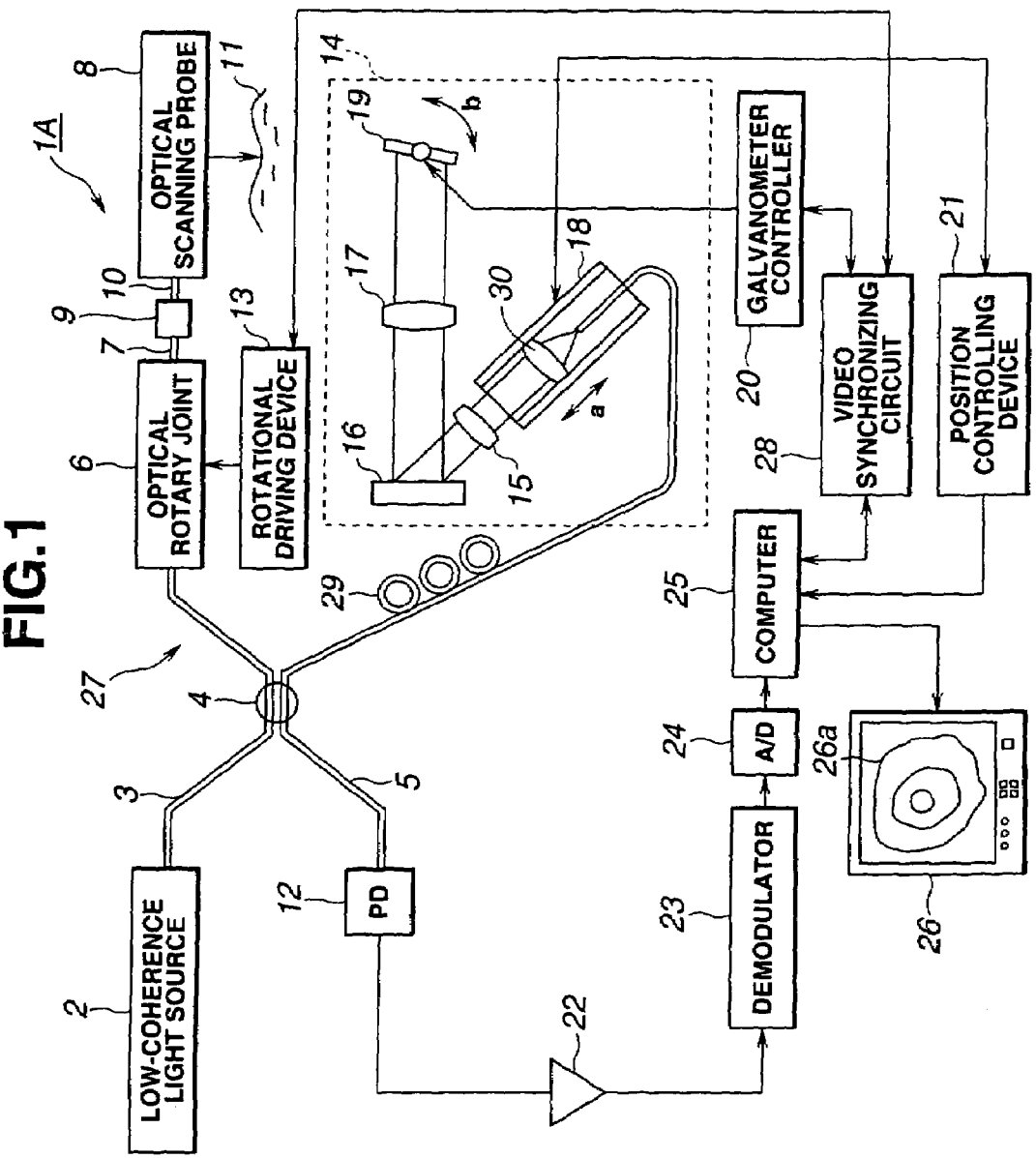

The optical imaging apparatus (optical tomography apparatus) IA shown in FIG. 1 has a low-coherence light source 2 such as a super-high luminance light-emitting diode (hereafter abbreviated as "SLD") or the like, within the observation apparatus 27. The wavelength of the low-coherence light source 2 is 1300 nm for example, characterized in that the interference is exhibited only in an extremely short range such as a coherency distance of around 17 μm. In other words, in the event that this light is split into two, and then mixed again, in the event that the difference in the two optical paths from the point of splitting to the point of mixing is within a short range of around 17 μm or so, the light is detected as interfered light, and in the event that the distance is greater than that, there is no interference.

The light from this low-coherence light source 2 is cast into one end of a first single mode fiber 3, and transmitted to the other end (the tip plane) thereof. This first single mode fiber 3 is optically connected with a second single mode fiber 5 with an optical coupler 4 along the way. Accordingly, the light is split two ways by this optical coupler 4 and thus transmitted.

An optical rotary joint 6, which performs optical connection whereby light can be transmitted through a non-rotating portion, and a non-rotating portion is introduced at the tip side (as viewed from the optical coupler 4) of the first single mode fiber 3. A connector portion 9 for an optical scanning probe 8 is detachably connected to the tip of a third single mode fiber 7 within this optical rotary joint 6, and passed through the optical scanning probe 8, so that light from the low-coherence light source 2 is transmitted (guided) to a rotationally driven fourth single mode fiber 10.

Then, the transmitted light is irradiated from the tip side of the optical scanning probe 8 to the organism tissue 11 serving as the subject, while being scanned. Also, a portion of reflected light due to scattering and the like at the surface or within the organism tissue 11 is taken in, returns to the first single mode fiber 3 side by passing over the reverse optical path, at which point a portion thereof is passed to the second single mode fiber 5 by the optical coupler 4, and cast from the end of the second single mode fiber 5 into a photo-diode 12 or the like serving as a photo-detector.

Incidentally, the optical rotary joint 6 is rotatably driven by a rotation driving device 13 within the observation apparatus 27.

Also, a variable-length optical path mechanism 14 for changing the optical path length of reference light is provided toward the tip of the second single mode fiber 5 as viewed from the optical coupler 4. This variable-length optical path mechanism 14 has a first optical path length changing means for high-speed changing of the optical path length within and corresponding to a scanning range of an optical path scanned by the optical scanning probe 8 in the depth direction of the organic tissue 11 over a certain scanning range only; and a second optical path length changing means capable of changing optical path lengths of around a length corresponding to the irregularities in the length of optical scanning probes, so that irregularities in the length of individual optical scanning probes can be absorbed.

A collimating lens 30 attached to a monoaxial stage 18 and movable in the direction indicated by the reference symbol "a" is positioned facing the tip of the second single mode fiber 5, and a grating 16 is positioned with a lens 15 facing 15, the same introduced therebetween. A galvanometer 19 capable of turning at a minute angle is attached as the first optical path length changing means, placed with a lens 17 facing the grating (diffraction grating) 16, this galvanometer mirror 19 being vibrated at a high speed in a rotating manner as indicated by the reference symbol "b," by a galvanometer controller 20.

This galvanometer mirror 19 causes reflection with the mirror of a galvanometer, wherein driving signals are applied to a galvanometer, thereby vibrating a mirror attached thereto at a high speed in a rotating manner.

That is to say, driving signals are applied by a galvanometer controller 20 so that high-speed scanning can be performed by the optical scanning probe 8 for a particular distance in the depth direction of the organism tissue, these driving signals causing vibrating at a high speed in a rotating manner as indicated by the reference symbol "b."

Then, the optical path of the light, which is emitted from the end plane of the second single mode fiber 5 due to this rotational vibrating and which returns by being reflected at the galvanometer mirror 19, changes by the amount of the scanning range of the certain distance in the depth direction of the organism tissue.

That is to say, a first optical path length changing means for obtaining a depth-direction tomogram is comprised of the galvanometer mirror 19. This optical path length changing means using a galvanometer mirror 19 is disclosed in Science, Vol. 276, 1997, pp. 2037–2039.

Also, the second single mode fiber 5 and collimating lens 30 are provided on a monoaxial stage 18 movable in the direction of the optical axis, as indicated by the reference symbol "a," thereby comprising the second optical path length changing means.

Also, a fiber loop 29 for polarization plane adjusting is provided to the second single fiber 5 in order to remove the effects of birefringence due to bending of fiber within the optical scanning probe 8 and of the entire interferometer comprised of fiber.

On the other hand, the monoaxial stage 18 has a second variable-length optical path means, having a variable length for the optical path capable of absorbing irregularities in the optical length of optical scanning probes, for dealing with replacing of the optical scanning probe 8, and also has adjusting means for performing offset adjusting so that an image can be formed from a desired position (that surface position even in the example that the tip of the optical scanning probe 8 is not in close contact with the surface of the organism tissue 11, for example, by changing the optical path length by the monoaxial stage 18 to set the interference state for the surface position of the organism tissue 11) in the event of obtaining an image in the depth direction through the optical path length according to the galvanometer mirror 19.

This monoaxial stage 18 has a motor for moving the stage, and the monoaxial stage 18 is moved in the direction indicated by the reference symbol "a," by a position controlling device 21.

The light of which the optical path length has been changed by this variable-length optical path mechanism 14 is mixed with the light leaking from the first single mode fiber 3 side at the coupler portion 4 provided partway on the second single mode fiber 5, and both are received by the photo-diode 12.

For example, the second single mode fiber 5 is set such that in the event that the monoaxial stage 18 is set at a position near the middle of the variable range thereof, the optical path length from the optical coupler through the fourth single mode fiber 9 and the optical scanning probe 8 to the organism tissue 11, and the optical path length passing through the second single mode fiber 5 and reflected by the galvanometer mirror 19 on the monoaxial state 18, are approximately the same length.

Then, setting the position of the monoaxial state 18 so as to be variable according to the optical scanning probe 8 to be actually connected and used absorbs irregularities in the length of the individual optical scanning probes 8, and rotationally vibrating the galvanometer mirror 19 at high speed in a rotating manner, or performing high-speed vibration thereof, so as to cyclically change the optical path length of the reference light thereof, causes interference with the reflected light at the depth position of the organism tissue 11 of the same value as this optical path length, and causes non-interference with reflected light at other depth portions.

The signals subjected to photoelectric converting at the above photo-diode 12 are amplified by an amplifier 22, and input to a demodulator 23. A demodulating process is performed at this demodulator 23 wherein only the signal components of the interference light are extracted, and the output thereof is passed through an A/D converter 24 and input to a computer 25. The computer 25 generates image data corresponding to the tomography image, outputs the data to the monitor 26, thereby displaying an OCT image on the display screen thereof.

The computer 25 is connected to the position controlling device 21, and the computer 25 controls the position of the monoaxial stage 18 via the position controlling device 21. Also, the computer 25 is connected to a video synchronizing circuit 28, so that the tomography image data is stored in internal memory in a manner synchronous with the video synchronizing signals for forming an image.

Also, the video synchronizing signals of the video synchronizing circuit 28 are also each sent to the galvanometer controller 20 and the rotation driving device 13, whereby, for example, the galvanometer controller 20 outputs driving signals at a frequency synchronized with video synchronizing signals (more specifically, of two video synchronizing signals, i.e., high-speed and low-speed video synchronizing signals, the high-speed first video synchronizing signals), and the rotation driving device 13 outputs driving signals at a frequency synchronized with the first video synchronizing signals at a cycle synchronized with video synchronizing signals (more specifically, the low-speed second video synchronizing signals), so that light is scanned in the circumference direction by rotation of the rotation driving device 13.

The optical scanning probe 8 in the first embodiment is arranged such that the optical scanning probe 8 can be inserted through the forceps insertion opening 32 in the endoscope 31 and passed through the forceps passage channel thereof so as to protrude from the top side of the optical scanning probe 8.

This endoscope 31 has a slender and flexible insertion portion 33 so as to be readily inserted into the body cavity, and an operating unit 34 of a greater diameter is provided at the rear end of the insertion portion 33. The forceps insertion opening 32 is provided near the rear end of this insertion portion 33, and the inside of the forceps insertion opening 32 is connected to the forceps passage channel.

An unshown light guide is passed through the insertion portion 33, the incidental end of this light guide is connected to the light source device, and illumination light is emitted from an illumination window provided at the tip portion of the insertion portion 33, thereby illuminating the affected portion or the like. Also, the arrangement is such that an observation window is provided next to the illumination window, to which an object optical system is attached so that the affected portion being illuminated can be optically observed. Then, under observation of the observation optical system at the tip portion of the endoscope 31, low-coherence light is irradiated from the optical scanning probe 8 toward the part of the organism tissue 11 which is the object of interest, i.e., the affected portion or the like, and internal tomography image data of the organism tissue 11 is obtained, so that the OCT image 26a can be displayed on the display screen of the monitor 26.

Figure 2:
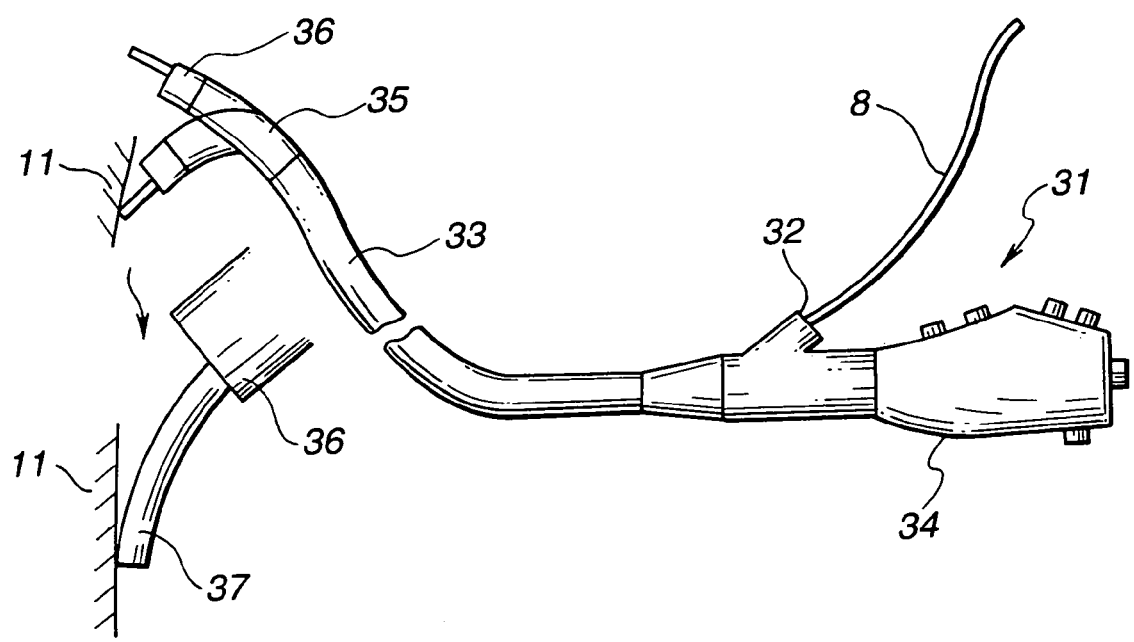

Also, a curving portion 35 and an endoscope tip portion 36 is provided to the tip portion of the insertion portion 33. The tip portion 36 of the optical scanning probe curves with a small curving diameter as shown in FIG. 2, when inserting the optical scanning probe 8 via the curving portion 35, or when protruding the tip 37 of the optical scanning probe 8 from the endoscope tip portion 36.

Figure 3:
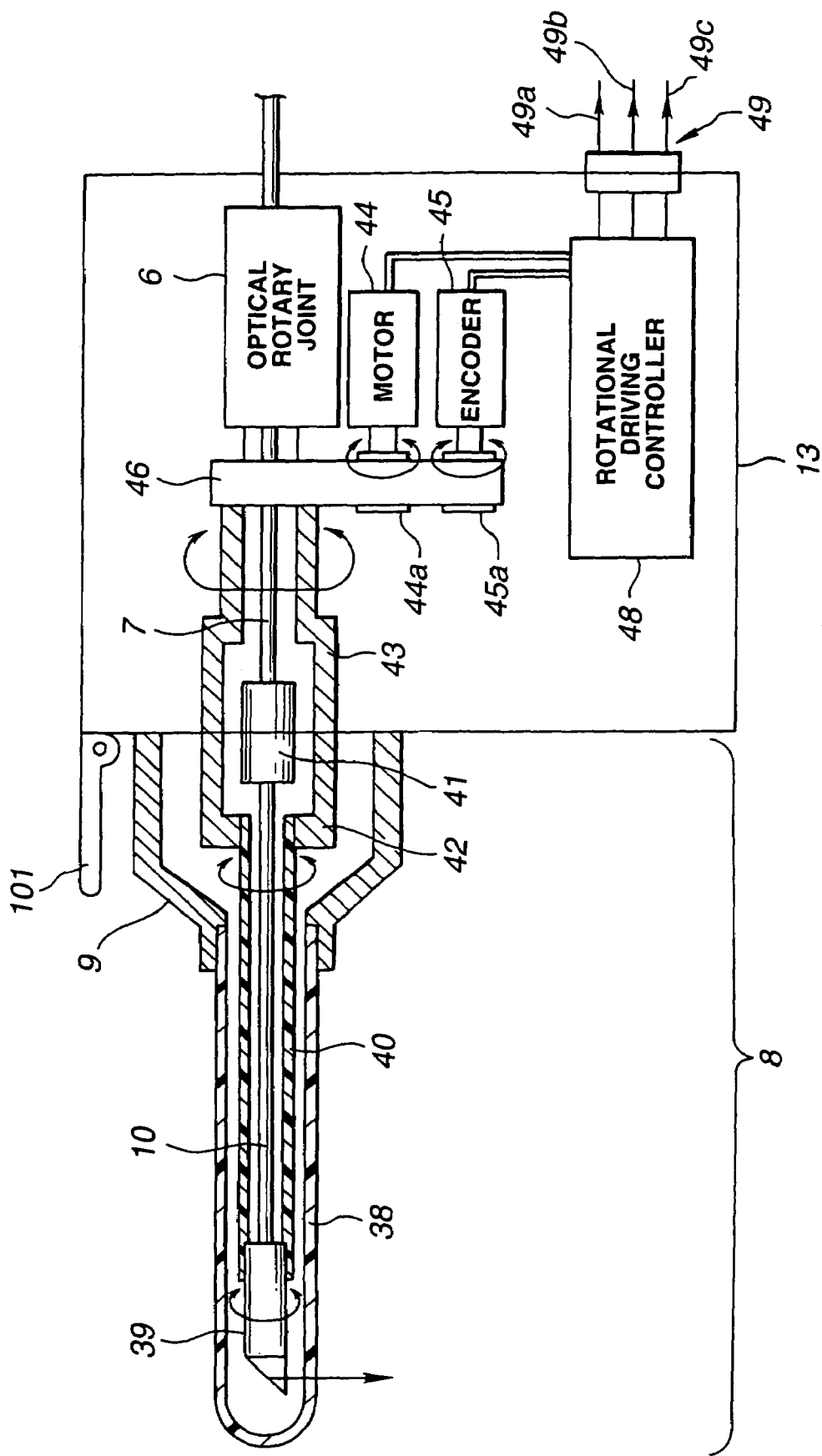

FIG. 3 illustrates the configuration of the optical scanning probe 8 and the rotation driving device 13 at the observation apparatus to which the optical scanning probe 8 is detachably connected. Incidentally, FIG. 3 illustrates the overall configuration of the connection portion of the optical scanning probe 8, with the detailed configuration thereof being shown in FIG. 5.

As shown in FIG. 3, the optical scanning probe 8 is configured of an optical sheath 38 configured of a slender tubular resin tube, a connector portion 9 detachably connecting this optical sheath 38 to the rotation driving device 13, a flexible shaft 40 which is a flexible pipe member for transmitting rotation force by rotating, a fourth single mode fiber 10 provided within the hollow of the flexible shaft 40, a lens unit 39 connected to the tip of the flexible shaft 40, a rotation transmitting connector 42 connected to the rear end of the flexible shaft 40, and an optical connector connected to the rear end of the fourth single mode fiber 10.

The rotation driving device 13 to which the rear end of the optical scanning probe 8 is connected has a hollow rotating shaft 43 and an optical rotary joint 6 connected to the rear end of the rotating shaft 43. An optical connector 41 is provided to the tip portion of this rotating shaft 43, and the optical connector 41 and the optical rotary joint 6 are connected by a third single mode fiber 7 provided within the hollow interior of the rotating shaft 43.

Also, the rotation driving device 13 has a motor 44 for rotating the rotating shaft 43 and an encoder 45 for detecting the rotations of the rotating shaft 43, with a belt 46 connecting a motor pulley 44a attached to the rotating shaft of a motor 44, an encoder pulley 45a attached to the rotating shaft of the encoder pulley 45a, and the rotating shaft 43.

Also, the motor 44 and encoder 45 are connected to a rotation driving controller 48.

Next, the action of the rotation driving device 13 will first be described. The rotations of the motor 44 are transmitted to the motor pulley 44a, and transmitted to the rotating shaft 43 and the encoder pulley 45a by the belt 46. The encoder 45 detects the rotating speed of the rotating shaft 43, and controls the driving current of the motor 44 by the rotation driving controller 48, so that the rotation speed is a specified speed. Accordingly, the rotating shaft 43 rotates at the specified speed in a constant manner. Also, the rotation angle of the rotating shaft 43 is detected by the encoder 45, and signals 49 are sent to the video synchronizing circuit 28 side via the rotation driving controller 48.

The signals 49 are comprised of A phase signals 49a of an A phase consisting of pulses obtained by one rotation being divided into 256 pulses, B phase signals 49b of a B phase which is offset from the A phase by 45 degrees, and one-rotation signals 49c which is a single pulse per rotation.

Next, the operation of the optical scanning probe 8 will be described. The light transmitted by the third single mode fiber 7 is transmitted to the fourth single mode fiber 10, by the optical connector 41. Also, the rotations of the rating shaft 43 are transmitted to the flexible shaft 40 by the rotation transmitting connector 42.

The transmitted light of the fourth single mode fiber 10 are sent to the lens unit 39, and emitted external therefrom through the optical sheath as inspection light, and the reflection light from the organism tissue is received and transmitted to the fourth single mode fiber 10 again. The tip of the flexible shaft 40 is connected to the lens unit 39, so the flexible shaft 40, lens unit 39, and fourth single mode fiber 10 rotate in an integral manner.

Figure 4:
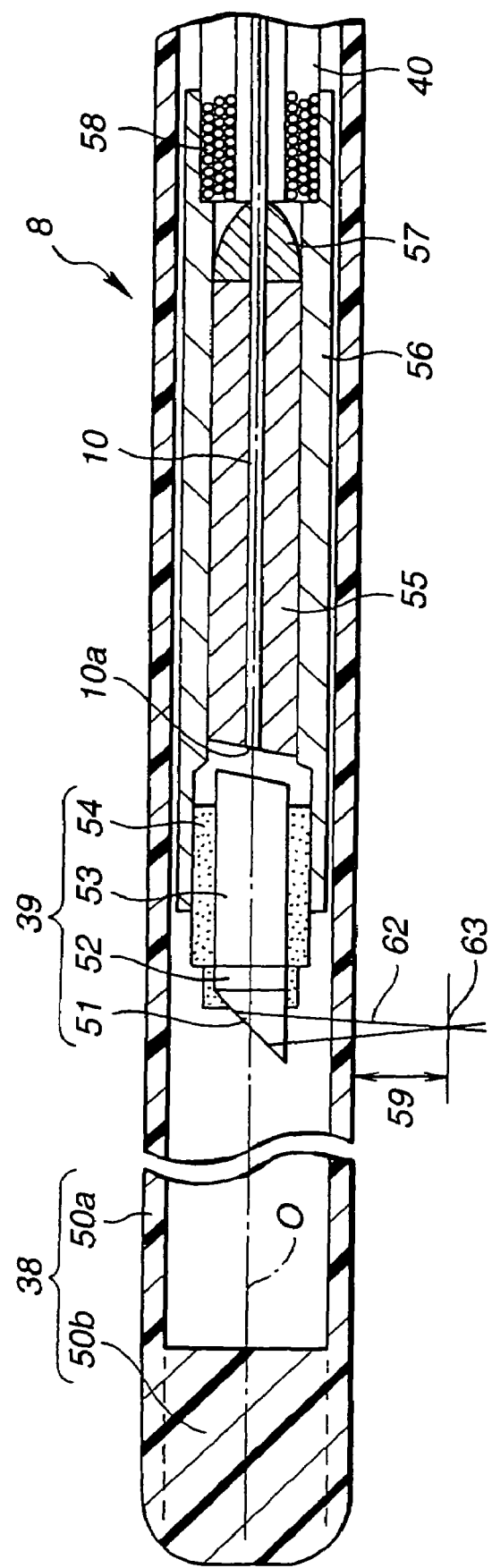

FIG. 4 illustrates the detailed configuration of the optical scanning probe. The optical sheath is comprised of a resin tube 50a which has flexibility, and a tip member 50b for closing off the tip opening of this resin tube 50a, with the resin tube 50a and the tip member 50b being joined by thermal fusion.

The lens unit 39 is comprised of a prism 51 serving as emission direction changing means for changing the emission direction of the low-coherence light, a Faraday rotator (Faraday rotation element) 52 for rotating the polarization plane of the low-coherence light, a converging GRIN lens (index distribution lens) 53, and a lens frame 54 for holding the above members. Also, the fourth single mode fiber is adhered to a ferrule 55, by an adhesive agent at the rear end of the ferrule 55.

The lens unit 39, ferrule 55, and flexible shaft 40 are connected with a hollow connecting member 56. Also, the tip of the flexible shaft 40 is inserted into the connecting member 56, and adhered with an adhesive agent 58 so as to be liked and fixed.

The low-coherence light transmitted following the center axis O of the single mode fiber 10 is emitted from the fiber end 10a at the tip of the single mode fiber 10, cast into the opposing GRIN lens 53 and converged, and further bent at a right angle by the prism 51, thereby transmitting the sheath 50a and becoming an observation beam 62, which is converged at a focal point 63 at a distance 59 from the outer surface of the sheath 50a, for example.

Incidentally, the tip side of the optical sheath, or more specifically the resin tube 50a of the portion facing the prism 51 at least, is formed of a good light-transmitting material which transmits low-coherence light.

Figure 5:
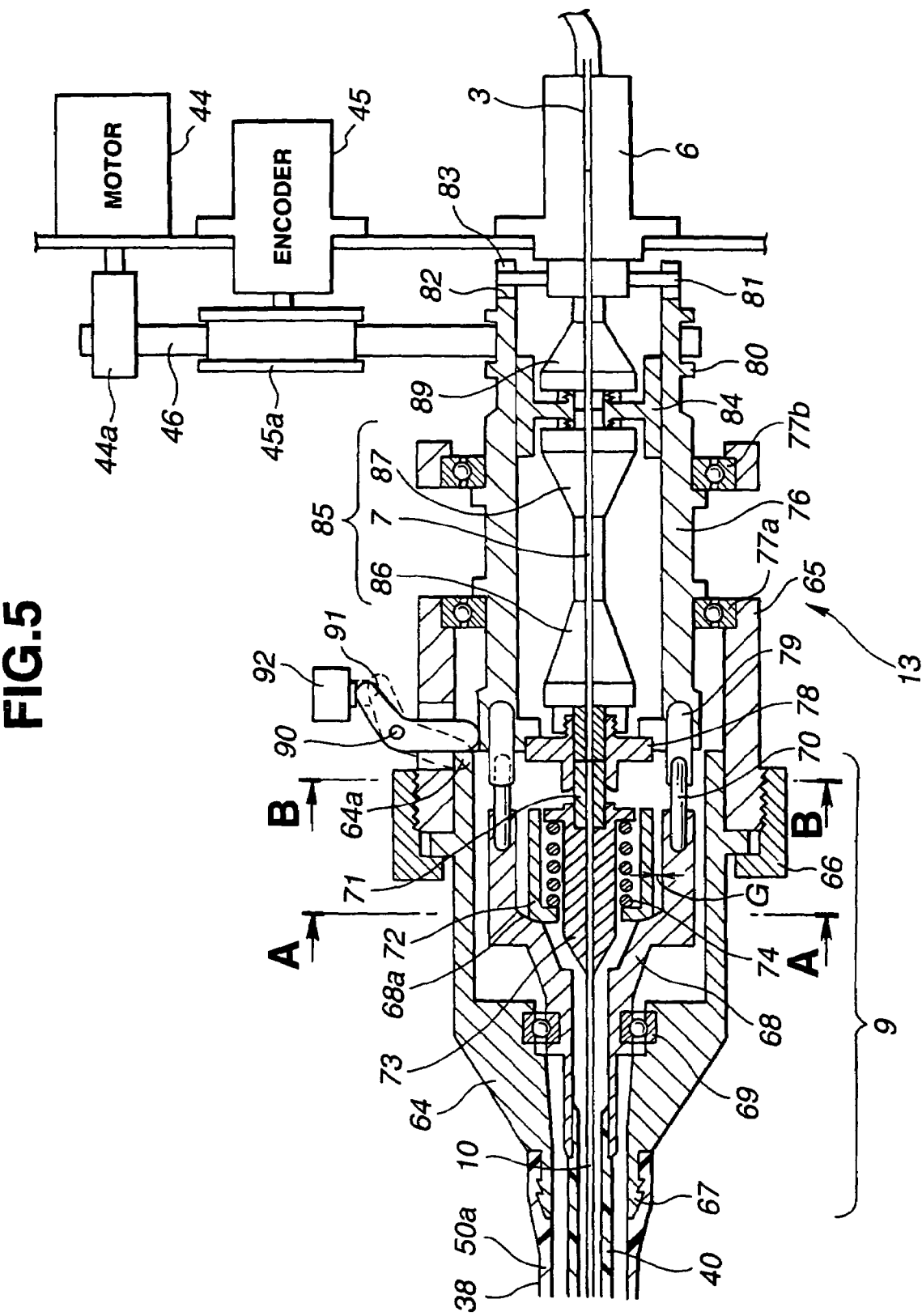

The detailed configuration of the connector portion 9 and the rotation driving device 13 is shown in FIG. 5.

The connector portion 9 is configured as follows.

The connector portion 9 is detachably connectable to the housing of the rotation driving device 13 with an attaching ring 66, by the connector case 64 which comprises the case portion thereof.

The rear end of the resin tube 50a forming the optical sheath 38 is connected to the sheath connecting portion 67 at the tip of the connector case 64, and the rear end (base) of the flexible shaft 40 is connected to the inner side of the connector case 64, with a shaft retainer 68 (equivalent to reference numeral 42 in FIG. 3) being provided as a rotation force transmitting member which transmits the rotation from the rotation driving device 13 to the flexible shaft 40 side.

This shaft retainer 68 is rotatably suspended by the bearing 69 serving as a rotating holding member provided between the shaft retainer 68 and the connector case 64. Rotation transmitting pins 70 (see FIG. 6B) are opposingly positioned at two positions on the shaft retainer 68 facing the circumference direction thereof.

The single mode fiber 10, ferrule 71, and a spring bracket 72 which is generally cylindrical in form, with the tip thereof having a protrusion which protrudes inwards, are provided to the inner hollow of the portion with an increased diameter at the rear end of the shaft retaining 68. The ferrule 71 is fixed to the optical connector 73 (equivalent to reference numeral 41 in FIG. 3) at the rear end of the single mode fiber 10. The rear end of the optical connector 73 has a protrusion protruding outwards, and a coil spring 74 serving as an elastic member having an internal diameter greater than the outer diameter of the optical connector 73 is positioned in the space between the optical connector 73 and the spring bracket 72, in a compressed state.

This coil spring 74 presses the protrusion of the optical connector 73 backwards with the elasticity thereof, and presses the protrusion of the spring bracket 72 forwards, so that the spring bracket 72 is pressed against the shaft retainer 68. Then, in the state with the connector portion 9 connected to the rotation driving device 13, the spring 74 presses the optical connector 73 (and the ferrule 71 joined to the fiber end) against the optical adapter 78 side toward the rear (the side of the rotation driving device 13).

Figure 6A:
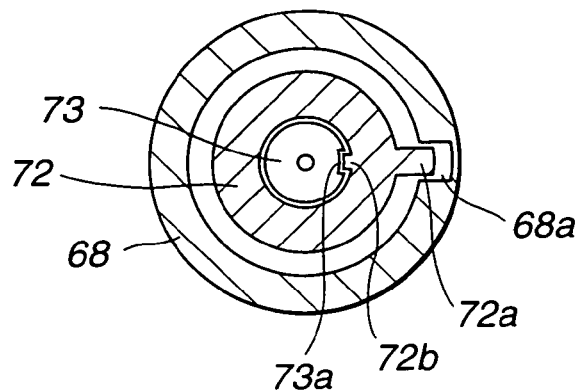
FIGS. 6A and 6B are cross-sectional diagrams illustrating the cross-sections A—A and B—B in FIG. 5.
Figure 6B:
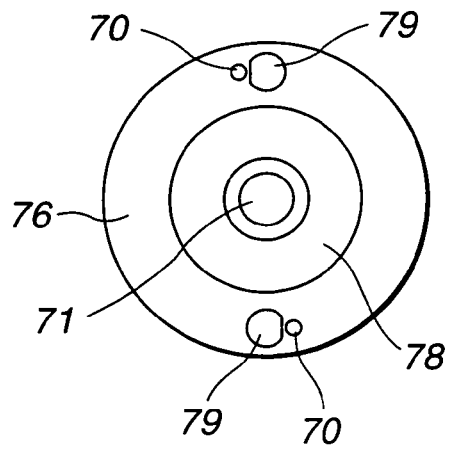
Figure 6C:
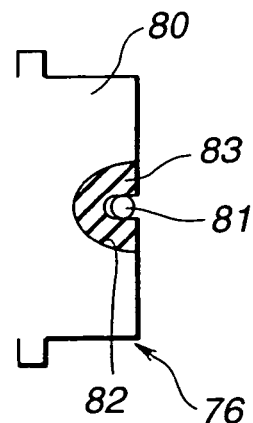
FIG. 6C is a diagram illustrating the configuration of the pulley portion.

Also, the spring bracket 72 is provided with protrusions 72a and 72b such as shown in the cross section along A—A in FIG. 6 and in FIG. 6A, and the shaft retainer 68 and optical connector 73 respectively are provided with corresponding recessions 68a and 73a, thereby preventing the optical connector 73 from unexpectedly rotating against the shaft retainer 68. Also, the attaching ring 66 detachably connects the connector case and the entire connector portion 9 to the housing 65 of the rotation driving device 13.

Next, the detailed configuration of the rotation driving device 13 comprising the observation apparatus 27 will be described.

A rotating shaft 76 is provided in the inner hollow of the housing 65, being rotatably held by two bearings, 77a and 77b. Two rotation transmitting levers 79 provided facing an optical adapter 78 connected by the rear end of the ferrule 71 being fit to one end thereof are provided to the rotating shaft 76. The ferrule attached to the tip of the single mode fiber 7 is inserted from the rear side of the optical connection hole of the optical adapter 78 and fit partway therein, and the ferrule 71 of the optical connector 9 side is fit from the front side thereof so as to position and thereby facilitate optical connection. Then, the rear end of the fiber 10 and the front end of the fiber 7 are brought into close contact by the elasticity of the spring 74, thus securing a stable light-transmitting state.

Also, the front portion of the optical connecting hole of the optical adapter is of a tapered wide diameter, so that even in the event that the ferrule 71 from the optical connector 9 side (or the rear end of the fiber 10) shifts in the axial direction with regard to the ferrule at the rotation driving side (or the front end of the fiber 7), the tapered surface serves as a guide, so as to correct the shifting and execute positioning.

As shown in FIG. 6 illustrating the cross-section along B—B in FIG. 5, the rotating shaft at the outer side of the optical adapter is arranged so that rotation transmission levers 79 protrude forwards at two opposing positions around the center axis, with each of the rotation transmission levers 79 neighboring rotation transmitting pins 70 provided to the shaft retainer 68 so as to protrude backwards, so that when the rotation transmission levers 79 rotate, the rotation transmitting pins 70 neighboring in the circumference direction are pressed so as to rotate together, thus transmitting the rotation.

Also, a pulley portion 80 is provided to the rear end of the rotation shaft 76, and provided to this pulley portion 80 is a U-groove 82 for rotating the rotation pin 81 of the optical rotary joint 6 as shown in FIG. 6, and an elastic member 83 provided between the U-groove 82 and the rotation pin 81.

Also, an optical fiber portion 85 is provided in the inner hollow of the rotating shaft 76, between the optical adapter 81 attached to the front end thereof, and the optical adapter 84 provided to the rear end thereof.

This optical fiber portion 85 comprises an optical connector 86 connecting with the optical adapter 78, an optical connector 87 connecting with the optical adapter 84, and a single mode fiber 7 connecting the optical connector 86 and the optical connector 87. Also, the optical connector 89 of the optical rotary joint 6 is connected to the optical connector 87 by the optical adapter 84.

Also, an insertion detecting lever 91 moving centrally around the shaft 90, and a switch 92, are provided to the connector connection portion to which the connector portion 9 is inserted and connected in the housing 65, with a form such as shown by dotted lines in FIG. 5 in the event that the connector portion 9 is not inserted, wherein inserting the connector portion 9 turns on the switch 92 by the insertion detecting lever 91 turning as shown from the dotted lines to the solid lines.

With the present embodiment, in the event of connecting the connector portion 9 to the connector connecting portion of the rotation driving device 13, a gap G is provided to the connector portion 9 side in the radius direction between the spring bracket 72 and shaft retainer 68 so as to absorb parallel offset between the rotating shafts, even in the event that the rotating axis of the rotating shaft 76 and the rotating axis of the shaft retainer 68 at the connector 9 side do not perfectly meet.

Also, the spring bracket 72 and shaft retainer 68 meet at a spherical portion 68a with rotation symmetry s to the rotation axes thereof, thereby absorbing angular differences between the rotation axes.

Figure 7A:
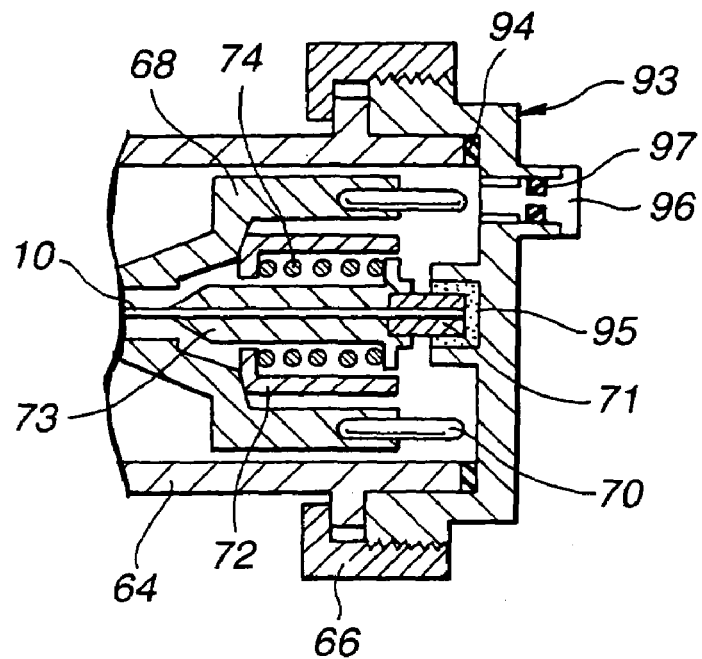

FIG. 7A shows the state of the connector portion 9 when being washed and when being stored.

A waterproof cap 93 is connected to the connector case 64 by the attaching ring 66, and a waterproof seal formed of an elastic member is provided between the waterproof cap 93 and the connector case 64, thereby comprising a watertight structure. Also, an optical connector cleaner 95 is provided at the portion of the waterproof cap 93 facing the ferrule 71, thereby preventing scratching or soiling of the optical fiber base of the ferrule 71, thus maintaining a clean state.

Also, the waterproof cap 93 is provided with a watertight test cap 96 and an O-ring for maintaining the watertightness of the watertight test cap 96 and the waterproof cap 93, thereby enabling the watertight test cap 96 to be removed, pressurized air to be introduced, and confirmation to be made of the watertight state of the optical scanning probe 8 according to whether or not air leaks from the optical scanning probe 8.

Figure 7B:
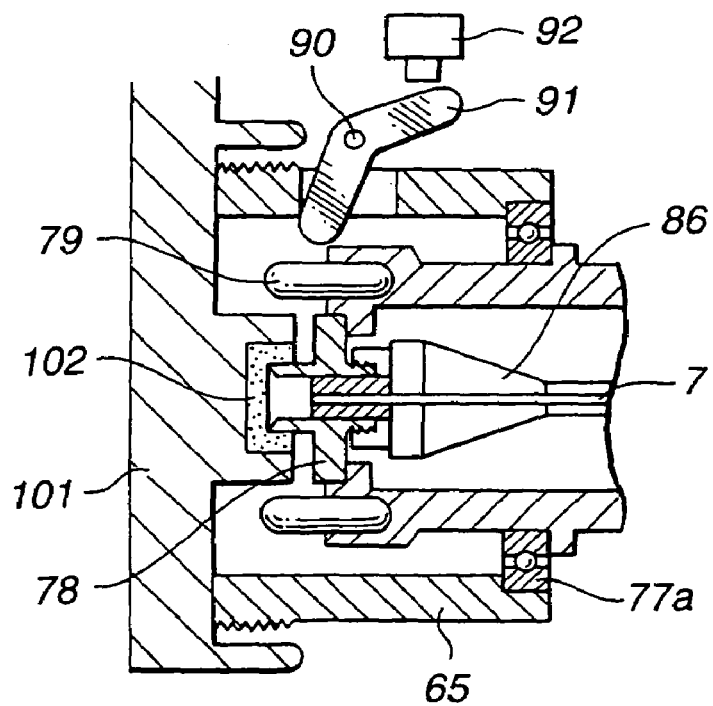

FIG. 7B illustrates the connector connecting portion at the rotation driving device 13 with the connector portion 9 not mounted.

A connector cap 101 is pressed against the housing 65, protecting the inside of the housing 65 so as not to be touched when not in use. Also, a dust-proofing cap 102 is provided at the portion coming into contact with the optical adapter 78 of the connector cap 101, thereby preventing intrusion of dust into the optical adapter 78.

The insertion detecting lever 91 is pressed by an unshown spring so as to rotate in the right direction clockwise, so the switch 92 does not conduct electricity.

Next, the operation of the optical connector portion 9 and the rotation driving device 13 will be described with reference to FIGS. 5, 7A, and 7B.

The waterproof cap 93 is removed from the optical connector portion 9, and the connector cap 1014 is removed from the housing 65. The connector case 64 is inserted into the housing 65, and is mounted to the housing 65 with the attaching ring 66. Accordingly, the optical connector portion 9 is fixed to the rotation driving device 13.

The insertion detecting lever 91 rotates to the left (i.e., counter-clockwise) on the shaft 90 by the edge portion 64a of the connector case 64, so the switch 92 conducts electricity. Electricity is provided to the motor only the switch 92 conducts electricity, the rotations of the motor 44 are transmitted to the belt 46 by the motor pulley 44a, and transmitted to the pulley 80 of the rotating shaft 76.

The rotating shaft 76, optical adapter 78, optical fiber cable 84, optical adapter 84, optical connector 89 of the optical rotary joint and rotating pin 81 rotate integrally. The rotation transmitting lever 79 provided to the rotating shaft 79 presses the rotation transmitting pin 70 provided to the rotating shaft 76, thereby transmitting the rotations to the shaft retainer 68 of the connector portion 9.

At this time, the optical connector 73 also rotates integrally with the shaft retainer 68, owing to the protrusions 72 and 72b provided to the spring bracket 72. Then, the rotations of the shaft retainer 68 are transmitted to the flexible shaft 40.

Now, generally, the rotating axis of the rotating shaft 76 and the rotating axis of the shaft retainer 68 do not perfectly meet, but a gap G is provided in the radius direction between the spring bracket 72 and shaft retainer 68 so as to absorb parallel offset between the rotating shafts, so parallel offset between the rotating shafts is absorbed by the spring bracket 72 moving by the amount of offset.

Also, the spring bracket 72 and shaft retainer 68 meet at a spherical portion 68a, thereby absorbing almost all angular differences between the rotation axes. Also, the ferrule is pressed against the optical adapter 78 side by elastic force of the spring 74, so even in the event that there is offset in the rotation axis direction, the tightly pressed optical connection state between the optical fibers 10 and 7 is maintained.

Also, once the switch 92 conducts electricity by movement of the insertion detecting lever 91, and the insertion of the optical scanning probe 8 is detected, an unshown low-coherence light emission display lamp is lit, and following a certain amount of time, the interlocking circuit (a safety circuit whereby the light source does not emit light in the event that the circuit is not conducting) of the low-coherence light source 2 begins conducting, and low-coherence light is emitted.

According to the present embodiment, even in the event that there is offset between axes, angular inclination, or slack in the axial direction, between the rotation axis of the rotation transmitting means for rotating the rotating tube provided to the connector portion 9 of the optical scanning probe 8, and the rotation axis of the rotation driving means provided to the observation device 27 side, such offsets can be absorbed to secure a stable connection between the optical fiber of the optical scanning probe 8 and the optical fiber of the observation device 27 side. Also, rotating force is smoothly transmitted from the rotation shaft of the rotation driving means to the rotation shaft of the rotation transmitting means.

Also, even in the event that the fiber end of the connection portion for the optical scanning probe 8 and the observation device 27 is soiled, the detachably provided signal mode fiber 7 at the connection portion with the optical probe of the observation device 27 can be replaced, and a good optical connection secured without the task of polishing the fiber end.

Also, the rotational force transmission connection and optical connecting means connection are both performed at the same time with a single attaching action of the connector portion 9 to the observation apparatus 27, facilitating ease of use.

Figure 8A:
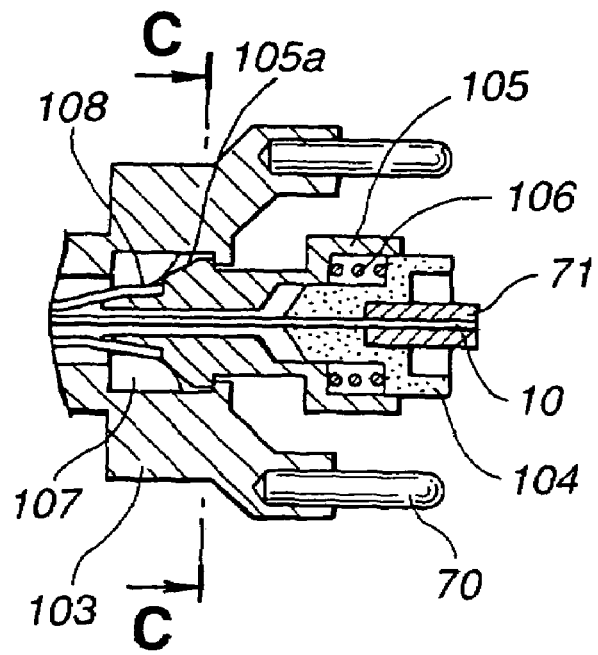
FIGS. 8A and 8B relate to a second embodiment of the present invention, FIG. 8A being a cross-section diagram of the principal members of the connector portion.

Next, a second embodiment according to the present invention will be described with reference to FIGS. 8A and 8B.

The objects of the present embodiment are the same as those of the first embodiment.

The difference with the arrangement shown in FIG. 5 will be described below, and other configurations are the same as those of the first embodiment. A shaft retainer 103 is provided instead of the shaft retainer 68.

The ferrule 71 is connected to a ferrule retainer 104, with the connector housing 105 and ferrule retainer 104 being slidable in the horizontal direction (the axial direction of the single mode fiber 10), and the ferrule retainer 104 is pressed to the right by the elastic force of the spring 106.

The base side of the connector housing has a tapered portion 105a provided thereto, coming into contact with the curved portion 108 of a sliding member 107 formed of a sliding plastic such as Derlin, provided to the shaft retainer 103.

Contact is made between a tapered form and a rounded form, so the connector housing 105 is somewhat movable in the shaft direction of the shaft retainer 103.

Figure 8B:
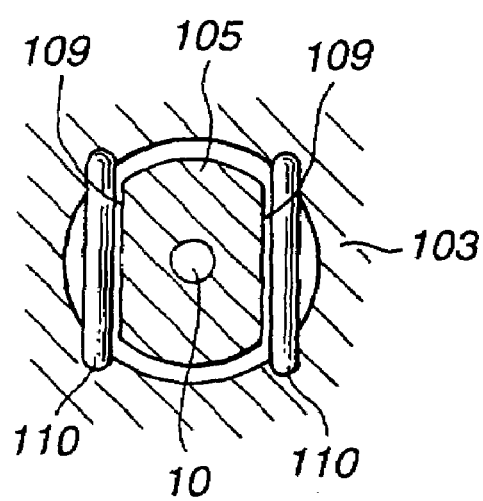

As shown in FIG. 8B which shows the cross-section along C—C, the connector housing 105 has a flat plane 109, a rotation preventing pin 110 is provided to the shaft retainer 103, and there are gaps between the shaft retainer 103, connector housing 105, and rotation preventing pin 110, so the connector housing 105 is integral with the shaft retainer 103, but is capable of some movement in the radius direction.

Accordingly, even in the event that offset occurs between the rotation axes of the rotating shaft 76 and optical connector portion 9, the offset can be absorbed, as with the FIG. 5 of the first embodiment.

The present embodiment has the following advantages.

In addition to those of the first embodiment, the connector housing 105, ferrule retainer 104, ferrule 71, spring 106, and so forth, can be configured of commercially-available optical connector parts such as FC connectors, thereby reducing costs.

Next, a third embodiment will be described with reference to FIGS. 9 and 10. The objects of the present embodiment are the same as those of the first embodiment.

Figure 9:
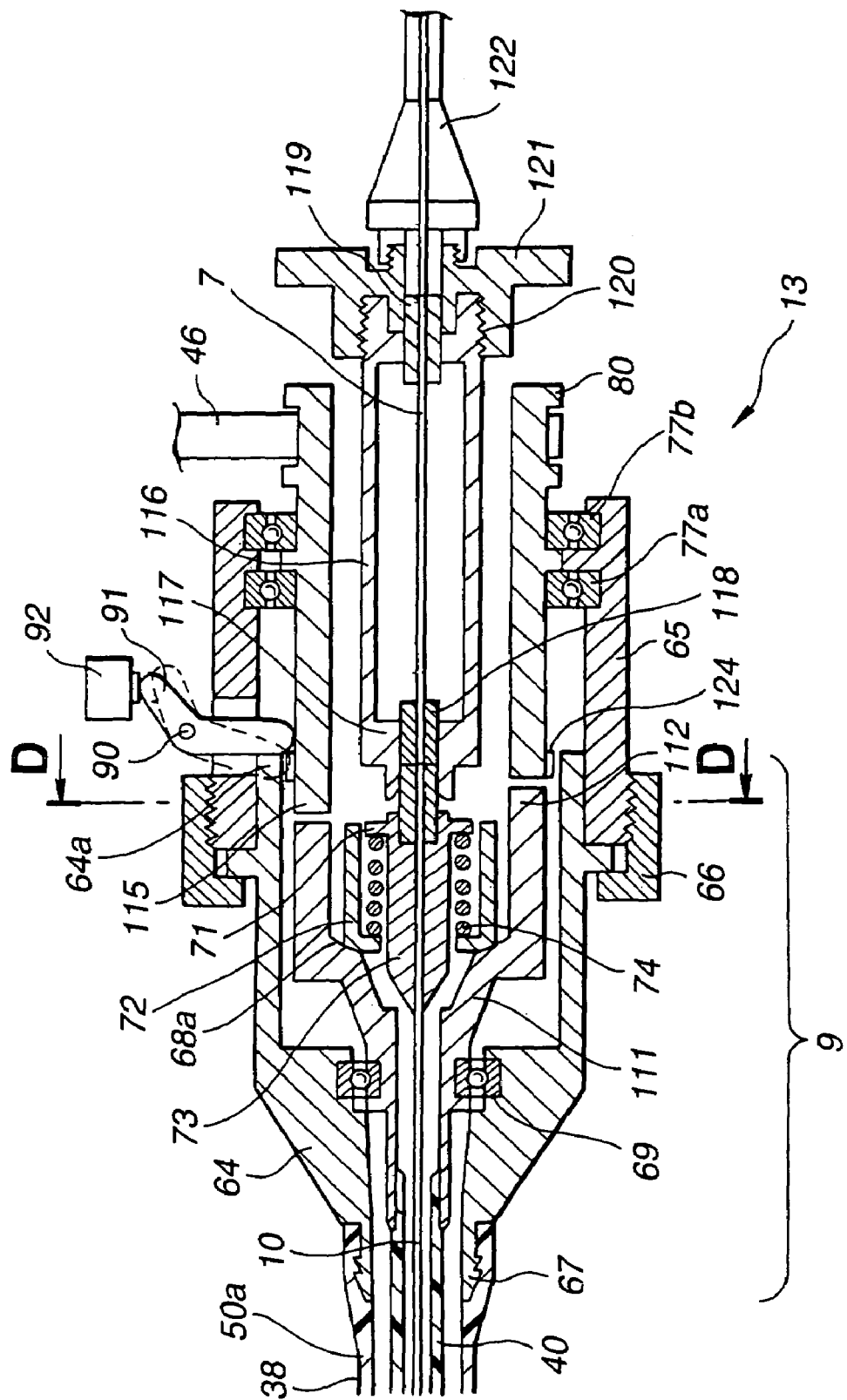

FIG. 9 shows the configuration of the connector connecting portion of the connector portion and rotation driving device according to the third embodiment.

The difference between the third embodiment shown in FIG. 9 and the first embodiment shown in FIG. 5 is that while with the first embodiment the optical adapter of the rotation driving device 13 rotates integrally with the rotating shaft 76, with the present embodiment, it is fixed.

With the present embodiment, the rotation transmitting pins 70 shown in FIG. 5 are not provided to the shaft retainer 111 provided instead of the shaft retainer 68 provided within the connector case 64 in FIG. 5.

Also, an optical fiber adapter 116 is provided in the inner hollow of the rotating shaft 115 provided instead of the rotating shaft 76 shown in FIG. 5. The tip end of this optical fiber adapter 116 comprises an optical adapter portion 117, with a ferrule 118 being provided to this optical adapter portion 117.

A ferrule 119 is provided to the rear end of the optical fiber adapter 116 and is fixed to the adapter 121 with a screw portion 120. The adapter 121 is fixed to the housing 65, so the optical fiber adapter 116 is also fixed to the housing 65.

The ferrule 119 and an optical connector 122 are connected by the adapter 121. An exchangeable single mode fiber 7 is passed through the ferrule 118 and the ferrule 119, in the same way as with the first embodiment.

Figure 10:
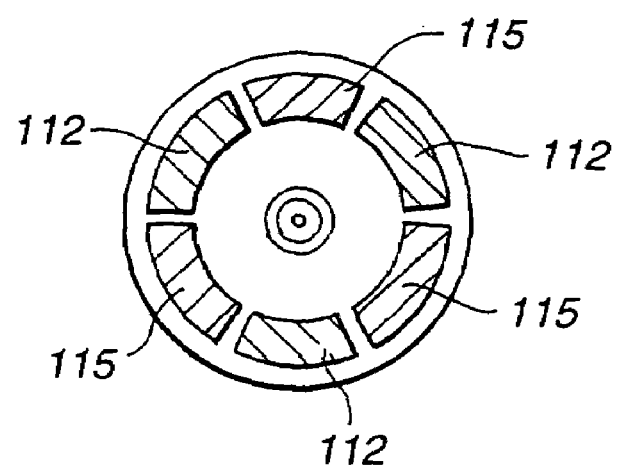
FIGS. 9 and 10 relate to a third embodiment of the present invention, FIG. 9 being a cross-section diagram illustrating the configuration of the connection portion between the connector portion and rotation driving device according to the third embodiment.

The rear end portion 112 of the shaft retainer 111 (i.e., the tip portion at the time of mounting/detaching) and the tip portion 115 of the rotating shaft 114 are positioned so that the ends thereof alternately neighboring in the circumference direction, as shown in FIG. 10 illustrating the cross-section along D—D in FIG. 9, and the rotation of the rotating shaft 114 is transmitted to the shaft retainer 111 by the tip portion 115 and the rear end portion 112.

Also, a plurality of rotation stoppers 124 are provided to the tip of the rotating shaft 115. In the state that the connector portion 9 is not inserted, the insertion detecting lever 91 is held at the position shown by dotted lines, by an unshown spring.

Accordingly, the insertion detecting lever 91 and the rotation stoppers 124 interfere, so there is no further rotation. In the event that the connector portion 9 is inserted, the insertion detecting lever 91 moves to the position shown by solid lines, so there is no interference with the rotation stoppers 124, and the rotating shaft 115 is free to rotate. Accordingly, mechanical rotation prevention preventing means are added to the electrical rotation prevention of the switch 92 when there is no insertion, effectively preventing wrapping in of the rotating portion.

With the present embodiment, in addition to the advantages of the first embodiment, the optical connection portion of the rotation driving device 13 and the optical scanning probe 8 also serves as the optical rotary joint 6 in the first embodiment, thereby reducing costs.

Next, a fourth embodiment of the present invention will be described with reference to FIGS. 11 and 12.

It is an object of the present embodiment to prevent offset between axes, angular inclination, or slack in the axial direction, between the rotation axis of the rotation transmitting means for rotating the rotating tube provided to the connector portion of the optical probe, and the rotation axis of the rotation driving means provided to the observation device, so as to secure a stable connection between the optical fiber of the optical probe and the optical fiber of the observation device side. Another object is to smoothly transmit rotating force from the rotation shaft of the rotation driving means to the rotation shaft of the rotation transmitting means.

Another object is to form the optical connector and rotation transmitting means between the optical scanning probe and rotation transmitting means of a single means, thereby simplifying the structure and lowering costs.

A further object is to use commercially-available optical connector parts such as FC connectors for the optical connector, thereby reducing costs.

Figure 11:
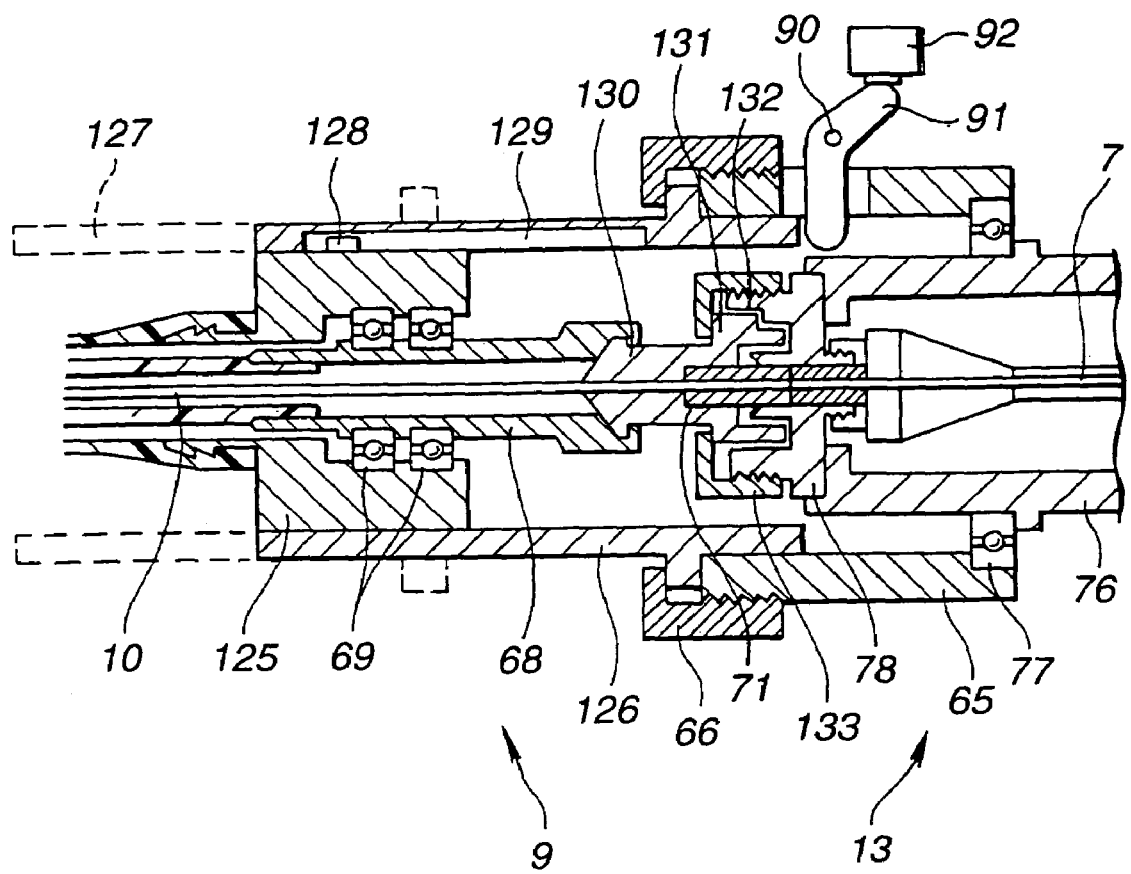
FIG. 11 is a cross-section diagram illustrating the configuration of the connection portion between the connector portion and rotation driving device according to a fourth embodiment of the present invention.

FIG. 11 shows the structure of the connector portion and rotation driving device according to the fourth embodiment. The difference with the arrangement shown in FIG. 5 will be described below, and other configurations are the same as those of the first embodiment. A connector case 125 is provided instead of the connector case shown in FIG. 5. The shaft retainer 68 within the connector case 125 is rotatably supported by the connector case by two bearings 69.

The connector case 125 comes into contact with the inner side of a pipe-shaped slide pipe 126, and the slide pipe 126 is slidable horizontally as to the connector case 125, to the position 127 shown by dotted lines in FIG. 11.

The slide pipe 126 is fixed to the housing of the rotation driving device 13 by the attaching ring 66. A rotation stopper 128 is provided to the connector case 125, and a sliding slit 129 is provided to the slide pipe 126, so there is no danger of the connector case 125 and shaft stopper 68 rotating together.

Figure 12:
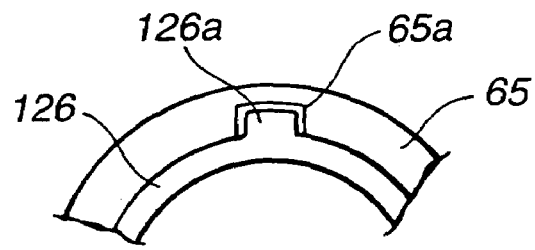
FIG. 12 is a diagram illustrating a rotation stopping mechanism between the slide pipe and housing shown in FIG. 11.

Also, a protrusion 126a such as shown in FIG. 12 is provided to the rear end of the slide pipe 126 (i.e., the tip portion at the time of mounting/detaching), so as to correspond with the recession provided in the housing 65, forming a rotation stopper, so not to rotate mutually in the event that the slide pipe 126 is attached to the housing 65 with the attaching ring 66.

The ferrule 71 is connected to the optical connector housing 130, and the optical connector housing 130 is joined to the shaft retainer 68.

The difference between the rotation driving device 13 according to the present embodiment and the arrangement shown in FIG. 5 is that the rotation transmitting lever 79 is absent from the tip of the rotating shaft 76, with only the optical adapter 78 provided. A protrusion 131 for stopping rotation is provided to the optical connector housing 130, and a groove 132 corresponding thereof is provided to the optical adapter 78. The optical connector housing 130 is attached to the optical adapter 78 by a screw 133.

Transmission of the rotation force from the rotation transmitting device 13 is performed by the connection between the optical adapter 78 and the optical connector housing 130. Rotation force is carried out by the rotation stopper 131 and recession.

In the event of connecting the connector portion 9 to the rotation driving device 13, the slide pipe 128 is slid into the position 127, the optical connector housing 130 and ferrule 71 are connected to the optical adapter 87, and attached by a screw 133.

Next, the slide pipe 126 is inserted into the housing 65, and fixed with the attaching ring 66. In the case of the present invention, the rotation axis of the rotating shaft and the rotation axis of the shaft retainer 68 must be precisely matched, for otherwise the loss owing to rotational wobbling becomes extremely great. Accordingly, there is the need to manufacture the members such that the positional precision regarding the rotation axis of the optical adapter 78, optical connector housing 130, shaft retainer 68, connector case 125, slide pipe 126, and so forth is high.

According to the present embodiment, in addition to the advantages of the first embodiment, only one rotation transmitting means is needed for the optical connector and rotation transmitting means between the optical scanning probe and rotation transmitting means, thereby simplifying the structure and lowering costs. Further, commercially-available optical connector parts such as FC connectors can be used for the optical connector, thereby reducing costs.

According to the above first through fourth embodiments, an optical imaging apparatus, which has an optical scanning probe which irradiates low-coherence light onto a subject and performs photo-reception of the light scattered at the subject, and an observation device for constructing a cross-section image of the subject, based on information from the light received through the optical scanning probe, with the optical scanning probe detachably connected thereto, comprises:

an optical scanning probe comprising:

a sheath, the greater portion thereof being formed of a flexible resin tube with at least the tip thereof being formed of a material with good light transmittance;

mounting/detaching means for mounting housing provided at the base end of the sheath to the observation device;

a pipe member provided rotatably within the sheath, around the longitudinal axis thereof;

a rotational force transmitting means provided to the base portion of the pipe member;

a rotation holding means for holding the rotational force transmitting means rotatably to the housing;

fiber comprised of single mode fiber provided within the flexible pipe member, with the tip portion thereof being fixed to the tip of the pipe member, such that the light cast from a low-coherence light source is cast into the base end thereof;

a lens for converging light cast from the fiber provided to the fiber tip;

a cast light path changing means fixed to the lens for changing the optical path of the cast light;

a fiber end fixing means provided to the base end of the fiber;

an elastic means provided between the fiber end fixing means and the rotational force transmitting means;

an observation device, comprising:

a rotational driving device for providing rotational force to the rotational force transmitting member of the optical probe;

an optical connecting means for connecting the fiber for sending and receiving observation light, provided to the single mode fiber of the optical probe of the observation device; and wherein, at the time of connecting the optical probe and the observation device, the fiber end fixing means come into close contact with the optical connecting means due to elastic means of the optical probe, thereby performing optical connection, so the fiber end of the optical scanning probe rotates while being pressed against the fiber end of the observation device, so even in the event that there is offset between axes, angular inclination, or slack in the axial direction, between the rotation axis of the rotation transmitting member and the rotation axis of the rotation driving means, such offset can be absorbed to secure a stable connection between the fiber ends.

Next, a fifth embodiment of the present invention will be described with reference to FIGS. 13A through 14.

An object of the present invention is to obtain a rotation scanning image with a correct positional relation with the rotating angle, even in the event that irregularities in the rotation speed of the rotating tube occur.

Another object is to obtain continuous rotation scanning images.

FIGS. 13A through 13D represent the relation between the scanning timing in the depth direction according to the optical scanning means, and the rotating angle of the optical scanning probe 8.

Figure 13A:
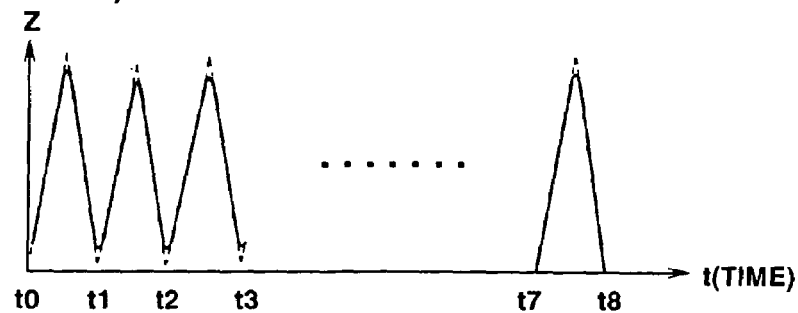

In the event of driving the galvanometer mirror 19 at high speed as shown in FIG. 13A, the driving is generally repeated at a certain cycle. At this time, the scanning cycle is constant. However, in actual practice, the rotations of the flexible shaft 40 of the optical scanning probe 8 is not constant, due to resistance from curving, and so forth.

Figure 13B:
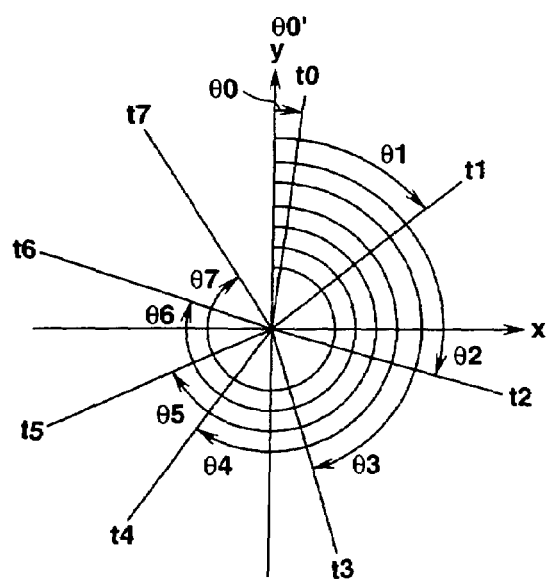

This is represented as a model in FIG. 13B. The scanning direction of one scan in the depth direction is represented by the lines t0 through t7. The time intervals for t0 through t7 are constant, but the rotation speed is not constant, so the angles between the lines t0 through t4 are wide, while the angles between the lines t5 through t7 are narrow.

Figure 13C:
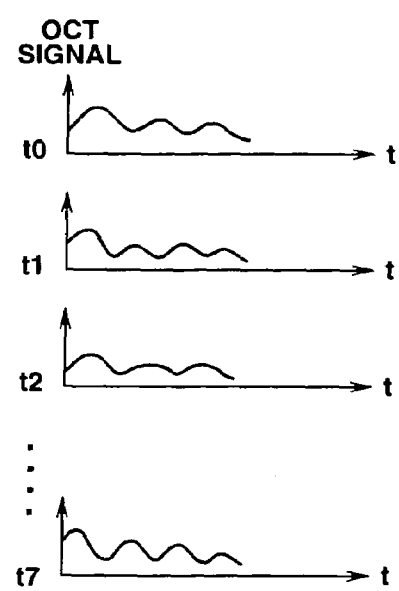
Figure 13D:
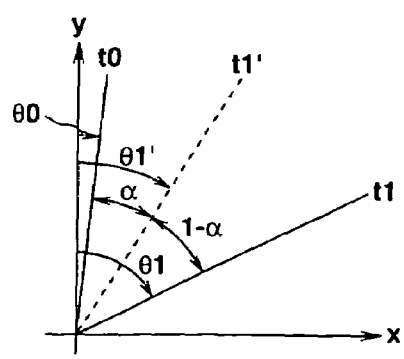

The depth-direction information obtained from OCT is represented in FIG. 13C. Here, the horizontal axis represents time t, and the vertical axis represents OCT signals (OCT information). The information obtained in the time from the point (t0 to t7) at which scanning of the mirror 19 is started corresponds with the OCT information in the depth direction.

Figure 14:
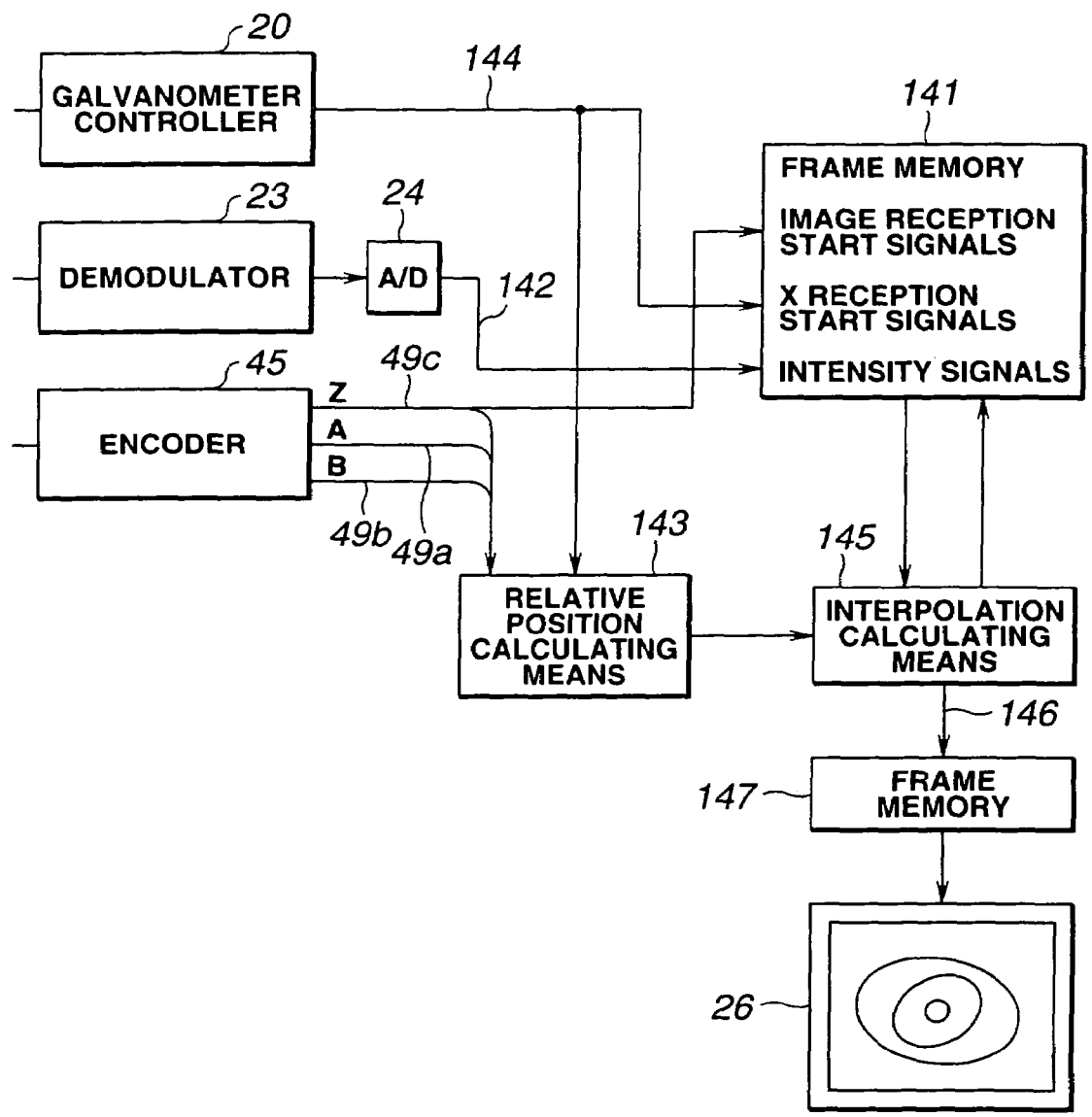

FIG. 14 shows the means for using such a scanning method to correct speed irregularities in scanning in the rotational direction of the scanning probe 8, and display as an observation image.

The scanning timing (equivalent to t0 to t7 in FIG. 13B) signal from the galvanometer controller 20 is received by the frame memory 141 as an X reception starting signal. The OCT interference signals are changed into intensity signals by the demodulator 23 and A/D converter 24, and input to the frame memory 141. The rotation angle of the optical scanning probe detected by the encoder 45 is detected with a received as the once-in-a-rotation Z signal 49c being received by the frame memory 141 as a plane reception start signal.

The output signals 49a, 49b, and 49c of the encoder 45 are input to the relative position calculating means 143, and the rotation angle of the optical scanning probe 8 is detected. Also, the timing signal 144 from the galvanometer controller 20 is input to the relative position calculating means 143, so that the relative relation for t0 through t7 and δ0 through δ7 shown in FIG. 13B can be calculated.

Based on the relation between the probe rotation angle and scanning timing from the relative position calculating means 143, the interpolation computing means 145 uses the information stored in the frame memory 141 to store observation data 146 in the frame memory 147, which is then displayed on the monitor 26 as an OCT image.

Next, the operation will be described.

The frame memory 141 is a memory which can store a great number of sets of time-series one-dimensional information, in a two-dimensional manner as a great number of rows of pieces of one-dimensional information. Storage of new two-dimensional information is started by the Z signal 49c of the encoder 45.

Once the timing signal 144 for starting scanning is input from the galvanometer controller 20, recording of the one-dimensional information row is started. Subsequently, input of the timing signal 144 performs storage of one-dimensional information rows, each time a scan is performed in the depth direction.

The relative position calculating means 143 has rotation information regarding at which rotation angle (δ0 through δ7) each scan (t0 through t7) in the depth direction has been performed. In the event that the relative position calculating means 143 attempts to obtain the image t1' with the rotation angle (δ1') of a constant interval, shown in FIG. 13D, the angle information regarding which angle position (α) between which scan (t0) and which scan (t1) this is, is sent to the interpolation computing means 145.

The interpolation computing means 145 obtains the desired information by interpolating from two or more nearby scan signals read from the frame memory 141.

The interpolation method used may be anything from a simple ratio distribution from the angle proximity, to polynomial or spline interpolation. The supplementary computation means 138 converts the signals obtained by computation so as to be displayed in the radius direction, and stores the signals in the frame memory 147.

At this time, the side close to the rotation center has information in a dense manner, but the other side only has information in a coarse manner, so that portion is subjected to interpolation using a similar technique, thereby displaying a smooth and uniform image.

In practice, the image should be obtained in real-time, so the relative position calculating means 143 performs calculations based on the information from rotation ago. The writing of the OCT intensity signal at the frame memory 141, the rearing in of the frame memory 141 by the interpolation computing means 145, and the writing of the frame memory 147 by the interpolation computing means 145 is performed almost simultaneously.

Accordingly, the frame memory 141 only needs to have capacity for storing row information for several scans.

Figure 15A:
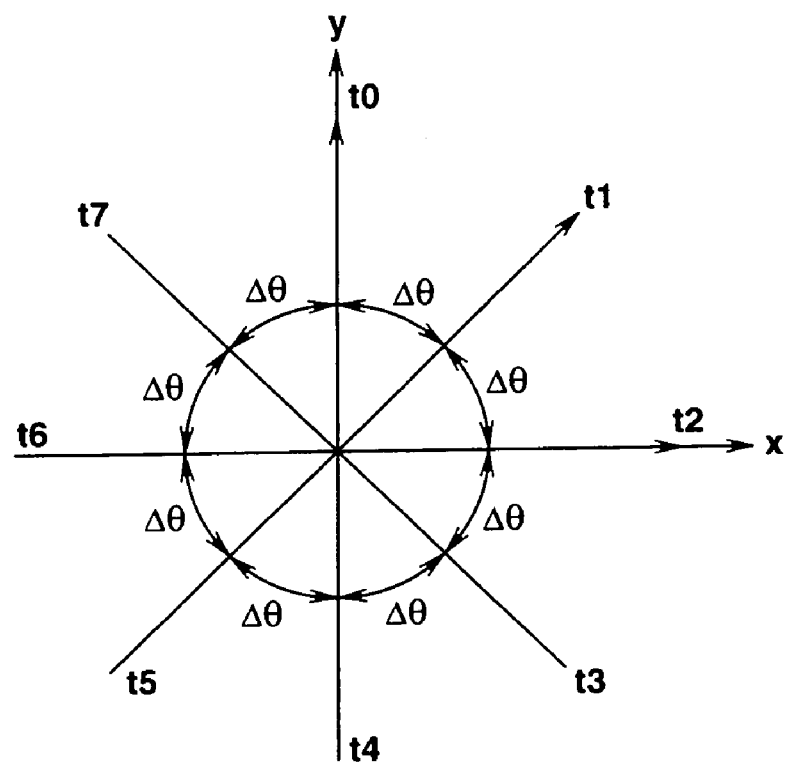
Figure 15B:
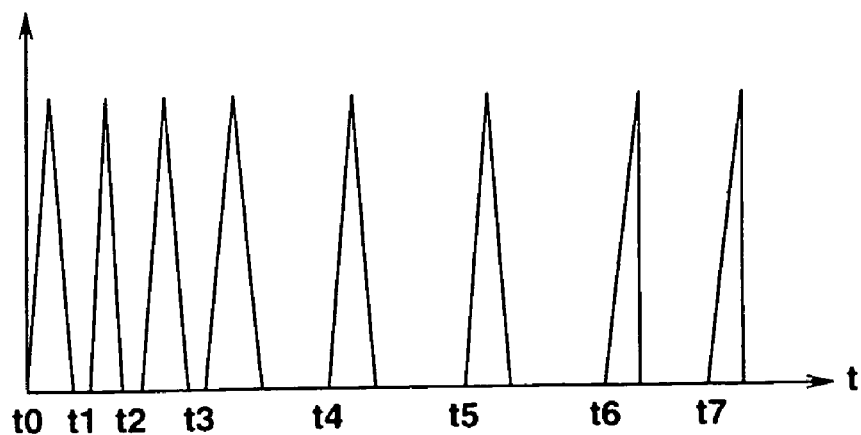

FIGS. 15A and 15b show a method according to a variation example.

Unlike the earlier method, this method involves using a high-speed variable scanning means to emit a scan start signal (t0 through t7) each time rotation of an angle Δδ of a certain interval is detected with the encoder 45, thereby performing scanning in the depth direction.

According to this method, there is no shifting between the scanning timing in the depth direction and the rotational angle, so a correct image can be displayed without using high-speed computing means such as the interoperation computing means 145 shown in FIG. 14

Next, a sixth embodiment of the present invention will be described.

An object of the present invention is to provide an optical probe wherein, even in the event that the inner side of the outer sheath is scratched, observation can be made by simply replacing the sheath portion, without replacing the entire probe device.

Also, another object is to provide an optical probe wherein inner side of the outer sheath is not easily scratched, by providing a curved plane at the holding portion of the optical element.

Another object is to provide an optical probe wherein a refractive index confirming water is sealed within the inner hollow of the outer sheath, thereby reducing reflection on the inner side of the outer sheath, consequently preventing ghosting.

Another object is to provide an optical probe wherein the refractive index conforming water can easily be sealed in following mounting or detaching, by providing a filler hole for sealing in the refractive index conforming water into the connector portion.

Another object is to provide an optical probe wherein the connection portion of the rotating tube is provided within the length range of the optical fiber connecting member, thereby reducing the stiff length.

The optical scanning probe 8A according to the sixth embodiment is of a configuration similar to that of the optical scanning probe shown in FIG. 1, with the configuration of the tip side thereof shown in FIG. 16.

The optical sheath 38 is comprised of a resin tube 50a which has flexibility, and a tip member 50b for closing off the tip opening of this resin tube 50a, with the resin tube 50a and the tip member 50b being joined by thermal fusion.

The lens unit 39 is comprised of a prism 51 serving as emission direction changing means for changing the emission direction of the low-coherence light, a Faraday rotator (Faraday rotation element) 52 for rotating the polarization plane of the low-coherence light, a converging GRIN lens (index distribution lens) 53, and a lens frame 54 for holding the above members. Also, the fourth single mode fiber is adhered to a ferrule 55, by an adhesive agent at the rear end of the ferrule 55.

The lens unit 39, ferrule 55, and flexible shaft 40 are connected with a hollow connecting member 56. Also, the tip of the flexible shaft 40 is inserted into the connecting member 56, and adhered with an adhesive agent 58 so as to be linked and fixed.

The low-coherence light transmitted following the center axis O of the single mode fiber 10 is emitted from the fiber end 10a at the tip of the single mode fiber 10, cast into the opposing GRIN lens 53 and converged, and further bent at a right angle by the prism 51, thereby transmitting the sheath 50a and becoming an observation beam 62, which is converged at a focal point 63 at a distance 59 from the outer surface of the sheath 50a, for example.

Incidentally, the tip side of the optical sheath, or more specifically the resin tube 50a of the portion facing the prism 51 at least, is formed of a good light-transmitting material which transmits low-coherence light.

Changing the spacing 61 between the fiber tip 10a at the tip of the fourth single mode fiber 10 and the GRIN lens 53 allows the position of the focal point 63 at the distance 59 from the outer surface of the sheath 50a to be changed (by changing the value of the distance 59). The connecting member 56 and the lens frame 54 rotate as to the sheath 50a by the rotation of the flexible shaft 40, so contact between the lens frame angle portion 54a and the interior of the sheath plane 173 often causes scratches.

Also, the overall length of the flexible shaft 40 changes according to the insertion form of the optical scanning probe 8, so scratches formed by contact between the lens frame angle portion 54a and the sheath interior plane 173 intersect with the observation beam 62, such that observation may not be performed normally.

In such cases, an observation image can be obtained by replacing the optical sheath 38 portion with a new optical sheath 38, as shown in FIG. 16.

FIG. 17 shows the configuration of the tip side of a scanning probe 8B according to a first variation example of the arrangement shown in FIG. 16. The optical sheath 38 is formed of a flexible nylon tube 164 and a tip cap 165 for closing off the tip opening thereof. With the nylon tube 164 and the tip cap 165 being joined by an adhesive agent. At least the tip side of the nylon tube 164 is transparent. A rounded cap 166 is connected to the tip side of the lens frame 55 of the lens unit 39. An opening portion 167 is provided in the rounded cap 166, so as to transmit the observation beam 62. The rounded portion 172 of the rounded cap 166 comes into contact with the interior plane of the sheath 173, so the interior plane of the sheath 173 is not readily scratched even when the rounded cap 166 rotates.

Incidentally, with this optical scanning probe 8B, a spacing tube 168 is introduced to the connecting member 56 so as to be attached to the lens frame 54 comprising the lens unit 39, with a certain optical path length secured therebetween.

Also, a stepped ferrule 60 is provided instead of the ferrule 55 shown in FIG. 16. The stepped ferrule 60 is provided with a stepped portion 170 formed by reducing the diameter of the rear end side of the ferrule 60 by grinding in a stepped form, so the outer diameter of the stepped portion 170 is smaller than the inner diameter of the flexible shaft 40, and inserted into the tip portion of the flexible shaft 40, so as to be fixed to the flexible shaft 40 by an adhesive agent at an adhesive filling portion 171, along with the fourth single mode fiber 10 therein.

Accordingly, the stiff length of the tip portion can be reduced by securing the adhesion length of the stepped ferrule 60 and the flexible shaft 40, and providing the adhesion portion between the flexible shaft 40 and the connecting portion within the range of the length of the stepped ferrule 60.

Also, the gap L between the rounded cap 166 and the tip cap 165 is a leeway gap to allow for relative movement between the flexible shaft 40 and the optical sheath 38 owing to expansion and shrinking or curving of the optical sheath 38 regarding the nylon tube 164 and the like, and though this differs according to the material of the optical sheath 38, around 8 mm or so is normally needed.

FIGS. 18A and 18B show a further second variation example of the configuration of the tip side of the optical scanning probe 8C. Refractive index conforming water 177 with approximately the same refractive index as the nylon tube 164 forming the light-transmitting window of the optical sheath 38 is filled in the inner hollow space between the optical sheath 38 and the lens unit 39.

Openings 166a and 166b are provided to the rounded cap 166 attached to the tip side of the lens frame 54, for transmitting observation beams 62 and also allowing passage of the refractive index conforming water 177.

The reflection plane 51a of the prism 51 comes into direct contact with the refractive index conforming water 177, and the refractive index of the prism material and the refractive index of the refractive index conforming water 177, so there is absolutely no reflection. Accordingly, a reflective coating layer such as aluminum coating or a dielectric multi-layer film coating is applied to the reflecting plane 51a, thereby causing reflection.

Also, a stainless-steel pipe 178 is provided instead of the stepped ferrule 60 shown in FIG. 17. A fiber core 179 and jacket 180 comprising the fourth single mode fiber 10 are inserted into the inner hollow of the stainless-steel pipe 178, and the jacket is fixed at an adhesion portion 184. Also, the tip of the stainless-steel pipe 178 is polished to a plane or spherical surface.

A glass material 181 is filled in the gap between the lens unit 39 and the stainless-steel pipe 178. Also, an air hole 183 for allowing air to escape from, at the time of inserting the lens unit 39, is provided to the connecting member 56 near the adhesion portion 182 with the glass material 181.

Filling the inner hollow between the optical sheath 38 and lens unit 39 with the refractive index conforming water 177 reduces the reflection at the inner plane of the optical sheath 38, and ghosting owing to multiple reflections with similar reflections occurring at the outer side of the optical sheath 38 can be prevented.

Also, the reflection at the inner plane of the optical sheath 38 is reduced, so the effects of irregular reflection owing to scratches can be reduced, even in the event that the inner plane of the optical sheath 38 is scratched.

FIG. 18B is a three-dimensional representation of the relation between the opening 166b and the connecting member 56.

FIG. 19A represents an optical scanning probe 8D with a resin cap 185 provided to the configuration of the optical scanning probe 8 shown in FIG. 16.

The resin cap 185 is formed integrally with the lens frame 54 and prism 51, and an opening 185a shown in FIG. 19B which is a cross-section along the line E—E in FIG. 109A is provided in the emitting direction of the observation beam 62 of the prism 51.

The resin cap 185 has a rounded portion similar to that of the rounded cap 166, and thereby has the same advantages of the arrangement shown in FIG. 17 and FIG. 18A, in that the inner plane of the sheath is not scratched.

Figure 20A:
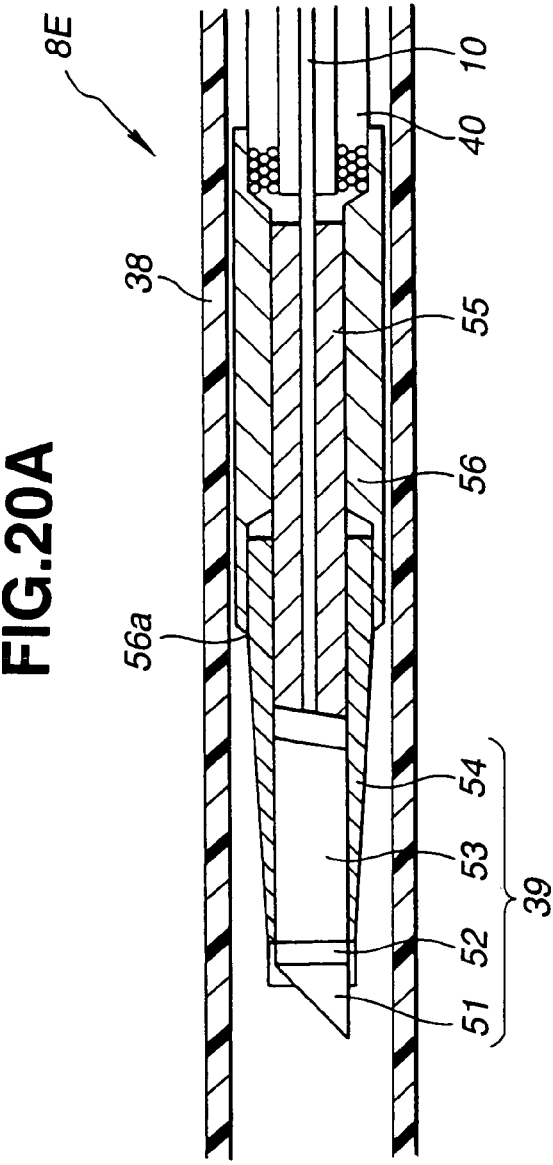
FIGS. 20A and 20B are diagrams illustrating the configuration of the tip side of the optical scanning probe according to fourth and fifth variation examples.

Another optical scanning probe 8E wherein the sheath is not scratched is shown in FIG. 20A. In the configuration shown in FIG. 16, the end portion 56a of the connection portion of the connecting member 56 with the lens frame 54 which may scratch the inner plane of the sheath is removed and positioned away from the light emitting/receiving portion.

For example, the circumference plane of the lens frame 54 is placed at the rearmost position, the tip side thereof is tapered so as to be of a small diameter, and the prism 51 and the like is attached to the tip side.

Even in the event that the lens unit 39 moves with respect to the optical sheath 38, and even in the event that the end portion 56a of the connecting member 56 causes scratches, the light emitting/receiving portion does not move that far, so there are no effects on sending and receiving of light.

Figure 20B:
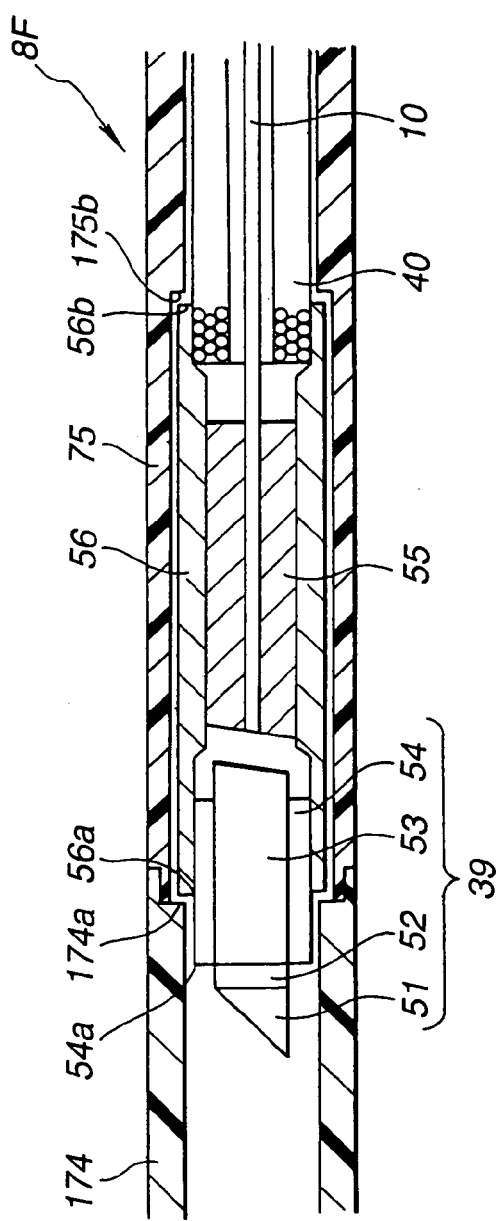

FIG. 20B shows yet another optical scanning probe 8F. A transparent sheath 174 having an abutting member 174a facing the front end 56a of the connecting member 56 across a gap, and a base side sheath 175 having an abutting member 175b facing the rear end 56b of the connecting member 56 across a gap, are joined so as to comprise the sheath 38 shown in FIG. 16.

The position of the connecting member 56 can be freely rotated, but with this configuration, the abutting member 174a and abutting member 175b perform restriction, so scratches within the sheath caused by the front end of the connecting member 56 and the angle portion 54a of the lens frame do not appear at the light emitting/receiving portion.

Figure 21:
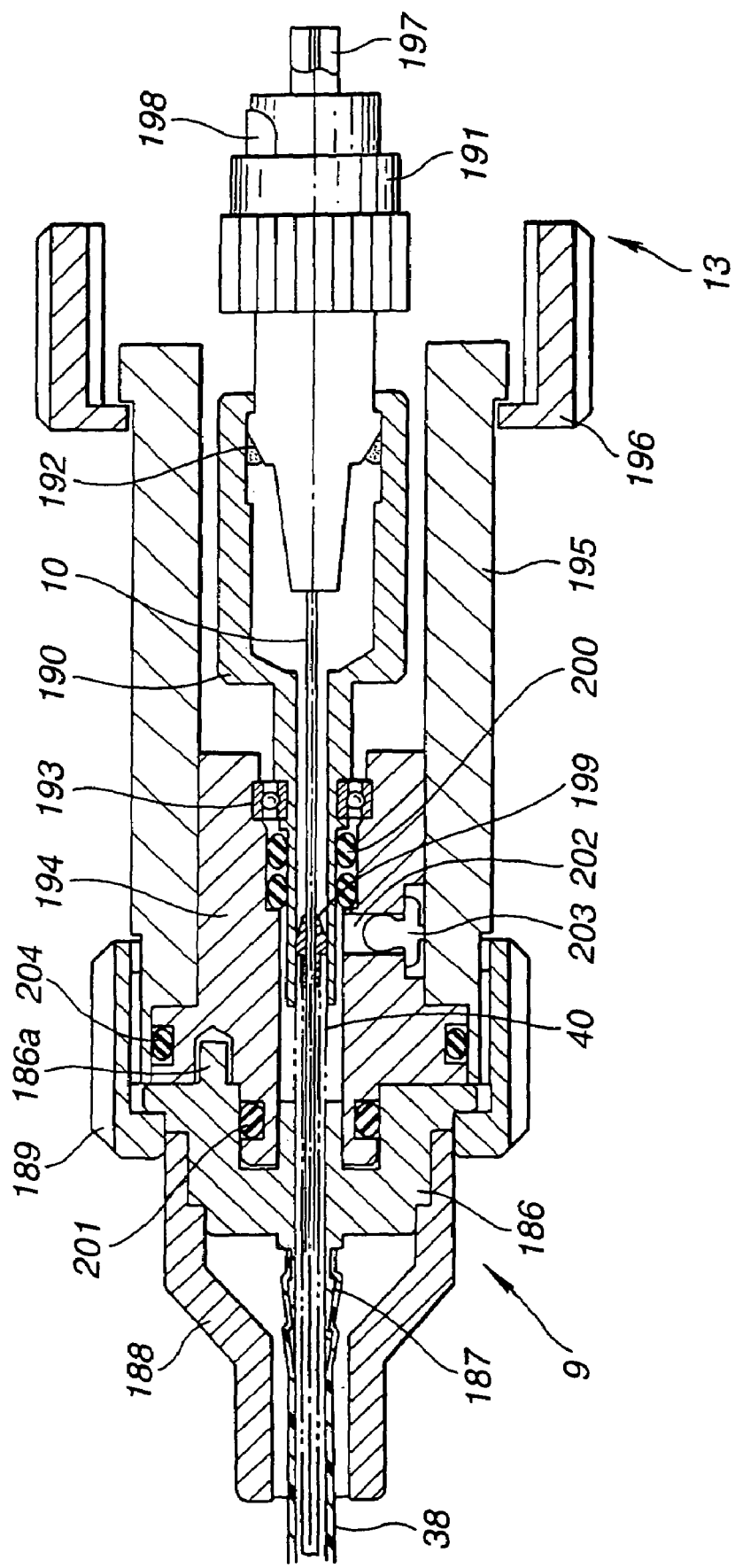

FIG. 21 shows a detailed configuration of the connector portion 9 at the base end of the optical scanning probe 8a or the like. The optical sheath 38 is detachably attached to a base member 187 having a sprout-like protrusion provided at the front of the sheath restrainer 186. Also, a buckling prevention member 188 is prevented to the sheath restrainer 186, so as to cover the rear end (base) portion of the optical sheath 38 with the buckling prevention member 188.

The flexible shaft 40 protruding from the rear end of this optical sheath 38 is attached to a connector retainer 190. This connector retainer 190 is joined to the optical connector at the adhesive portion 192.

Also, the connector retainer 190 is rotatably supported by the bearing base 194 via bearing 193. The bearing base 194 is attached to the rotation driving device 13 (see FIG. 3) by a case 195 and a tightening ring 196.

Also, the rear end plane of the sheath restrainer 186 is pressed against the front end plane of the bearing base 194, and the sheath restrainer 186 is detachably fixed to the case 195 with the screw 189.

In this case, a rotation stopping protrusion 186a provided to the end plane of the sheath restrainer 186 is fit into the recession provided in the end plane of the bearing base 194, thereby preventing the sheath restrainer 186 from moving unexpectedly.

Also, the optical connector 191 has a ferrule 197 for connecting the fourth single mode fiber 10 and the rotation driving device 13, and a rotation stopper 198 for determining the connection direction of the optical connector 191.

Rotating the optical connector 191 rotates the connector restrainer 190, so the rotation is transmitted to the flexible shaft 40. Also, the connector restrainer 190, the flexible shaft 40, and the single mode fiber 10 are adhered at a watertight adhesion portion 199 so that the watertightness thereof is maintained.

Also, an O-ring 200 is provided as a watertight seal between the connector restrainer 190 and the bearing base 194. Also, an O-ring 201 serving as a watertight seal is also provided between the sheath restrainer 186 and the bearing base 194.

These watertight seals allow refractive index conforming water 177 to be sealed in from the filler hole 202 provided to the bearing base 194, without the refractive index conforming water 177 filled in the space between the optical sheath 38 and the flexible shaft 40, from leaking.

Also, there is no leaking out of water seeping in from the gaps of the flexible shaft 40. The filler hole 202 is usually closed off with a filler hole lid 203.

Also, an O-ring 204 is also introduced between the bearing base 194 and the case 195, securing watertightness.

According to the present embodiment, as shown in FIG. 21, the base end of the optical sheath is detachably connected to the base portion 187 of the sheath retainer 186, and so in the event that a scratch is formed on the inner plane of the optical sheath, all that is necessary is to remove the optical sheath 38 from the base portion 187 and replace with a new optical sheath; the other members can be used as they are.

Next, a seventh embodiment of the present invention will be described with reference to FIG. 22. The object of the present embodiment is to exchange the sheath and thus allow observation to be made even in the event that the inner plane of the outer sheath is scratched.

Another object is to arrange for only the light transmitting portion of the sheath tip portion to be replaceable, thereby reducing costs.

Also, a hard coating is provided to the point of contact between the optical element holding portion and the inner plane of the sheath, thereby preventing scratches owing to contact from occurring.

Also, a reflection prevention coating is provided at the light-transmitting portion of the inner side of the sheath for transmitting irradiated light and observation light, thereby reducing reflection within the sheath, and preventing ghosting.

Figure 22:
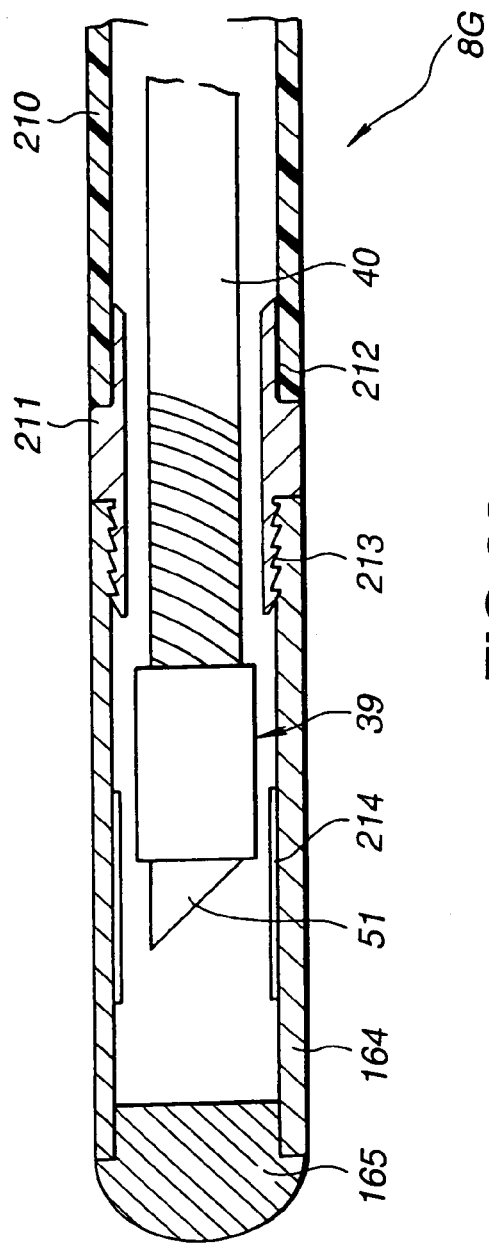
FIG. 22 is a cross-section diagram illustrating the tip side of the optical scanning probe according to a seventh embodiment of the present invention.

The optical probe 8G shown in FIG. 22 differs from the optical scanning probe 8B shown in FIG. 17 according to the sixth embodiment is that a resin tube 110 wherein the optical sheath is not light-conductive (or either light-transmitting or not light-transmitting) and a light-transmitting tube 164 are connected by a connecting tube 211.

The connecting tube 211 and the tube 210 fit and are joined by an adhesive portion for example. A base portion 213 of the connecting tube 211 having a sprout-like protrusion provided thereto is inserted and connected to the rear end of the tube 164.

Also, a hard coating portion 214 is provided to the portion at the inner side of the tube where there is a possibility of the lens unit 39 and the prism coming in contact with the tube 54, so that scratching dies not easily occur even in the event that there is such contact. A thin-film ceramic coating such as titanium nitride and so forth is an example of an appropriate hard coating for the resin. Or, a thin glass tube may be sealed in instead of the coating.

In the event that the inner plane of the sheath 164 is scratched, the sheath 164 and the connecting tube 211 are not connected by adhesion, so the sheath 164 can easily be replaced by cutting away the old sheath 164 and mounting the new sheath 164 to the base portion 213 of the connecting tube 211.

Also, a reflection prevention coating formed of a dielectric multi-layer film or the like may be provided instead of or in addition to this hard coating portion 214, thereby reducing reflection due to the refractive index difference between the air inside the tube 164 and the tube 164 itself, consequently obtaining effects the same as the refractive index conforming water 177 in the first embodiment shown in FIG. 18A.

Further, ghosting owing to multiple reflections between reflections at the inner plane and reflections with the interface of inner optical elements can be prevented, by providing reflection prevention coating formed of a dielectric multi-layer film or the like corresponding with ambient air, spirit water, organic tissue, and other mediums, and providing a reflection preventing coating formed of a dielectric multi-layer film or the like of a medium of the exterior of the tube 164.

According to the present embodiment, the above objects can be realized.

That is to say, even in the event that the inner plane of the tube 164 forming the optical sheath 38 according to the sixth embodiment is scratched, observation can be made by exchanging the tube 164 portion. In this case, the entire sheath does not have to be replaced, but only the light-transmitting portion at the tip end portion is made to be replaceable, thereby reducing costs.

Also, scratching due to contact does not occur so easily, since a hard coating portion 214 is provided to the contact portion between the optical element holding portion and the inner plane of the sheath.

Also, a reflection preventing coating is provided to the portion for transmitting irradiated light and observation light, thereby reducing reflection within the sheath and preventing ghosting.

Next, an eighth embodiment of the present invention will be described.

It is an object of the present embodiment to provide an optical imaging device wherein the length of the optical path can be automatically corrected even when replacing optical probes, thereby obtaining a tomogram in a sure manner.

Figure 23:
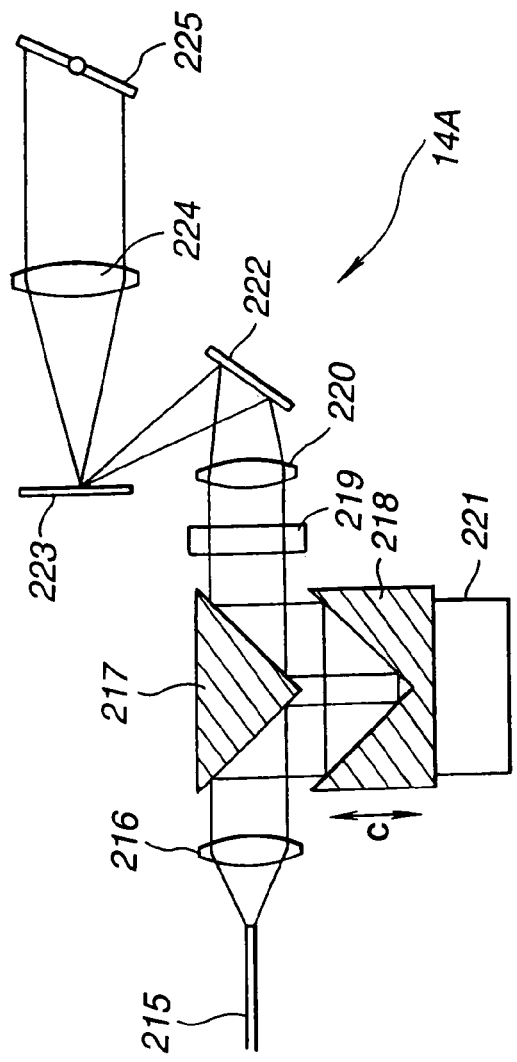

FIG. 23 illustrates the configuration of a variable-length optical path mechanism 14A according to the optical imaging device of the eighth embodiment, having a first optical path length changing means and a second variable-length optical path mechanism.

This is equivalent to another embodiment of the variable-length optical path mechanism 14 provided to the end portion of the second single mode fiber 5, shown in FIG. 1.

The light emitted from the second single mode fiber (equivalent to reference numeral 5 in FIG. 1) according to the present embodiment is converted into parallel rays by the collimating lens 216, cast into a reflecting mirror 217, and reflected at a right angle. The light from this reflecting mirror 217 is cast into the reflecting mirror 217 again from a corner mirror, is transmitted through the Faraday rotator 219, and is cast into the lens 220.

The corner mirror 218 is attached to a monoaxial slider 221, movable in the direction shown by the arrow c, and changing the spacing between the reflecting mirror 217 and the corner mirror 218 allows the optical path length to be changed greatly.

The light cast into the lens 220 is reflected from a mirror 222, cast into grating 223, and the light split by the grating is cast into a galvanometer mirror 225 by an optical lens 224. The light reflected off of the galvanometer mirror 225 passes through the reverse optical path and is cast into the fifth single mode fiber 215.

The light delay time can be changed by scanning the galvanometer mirror 225. Other configurations are the same as those described with the first embodiment shown in FIG. 1.

The fact that birefringence generated by bending of internal fiber due to bending or the optical scanning probe 8 (or 8A) can be compensated for by the Faraday rotator 52 provided to the optical scanning probe 8 (or 8A) on the arm of the interferometer toward the object side, shown in FIG. 4 for the first embodiment (or FIG. 16 for the sixth embodiment), and the Faraday rotator 219 shown in FIG. 23 on the arm of the reference light side, is disclosed in "Rapid acquisition of in vivo biological images by user of optical coherence tomography," G. J. Teamey et al., Optics Letters, Vol. 21, No. 17, pp. 1408–1410, 1996.

Figure 24:
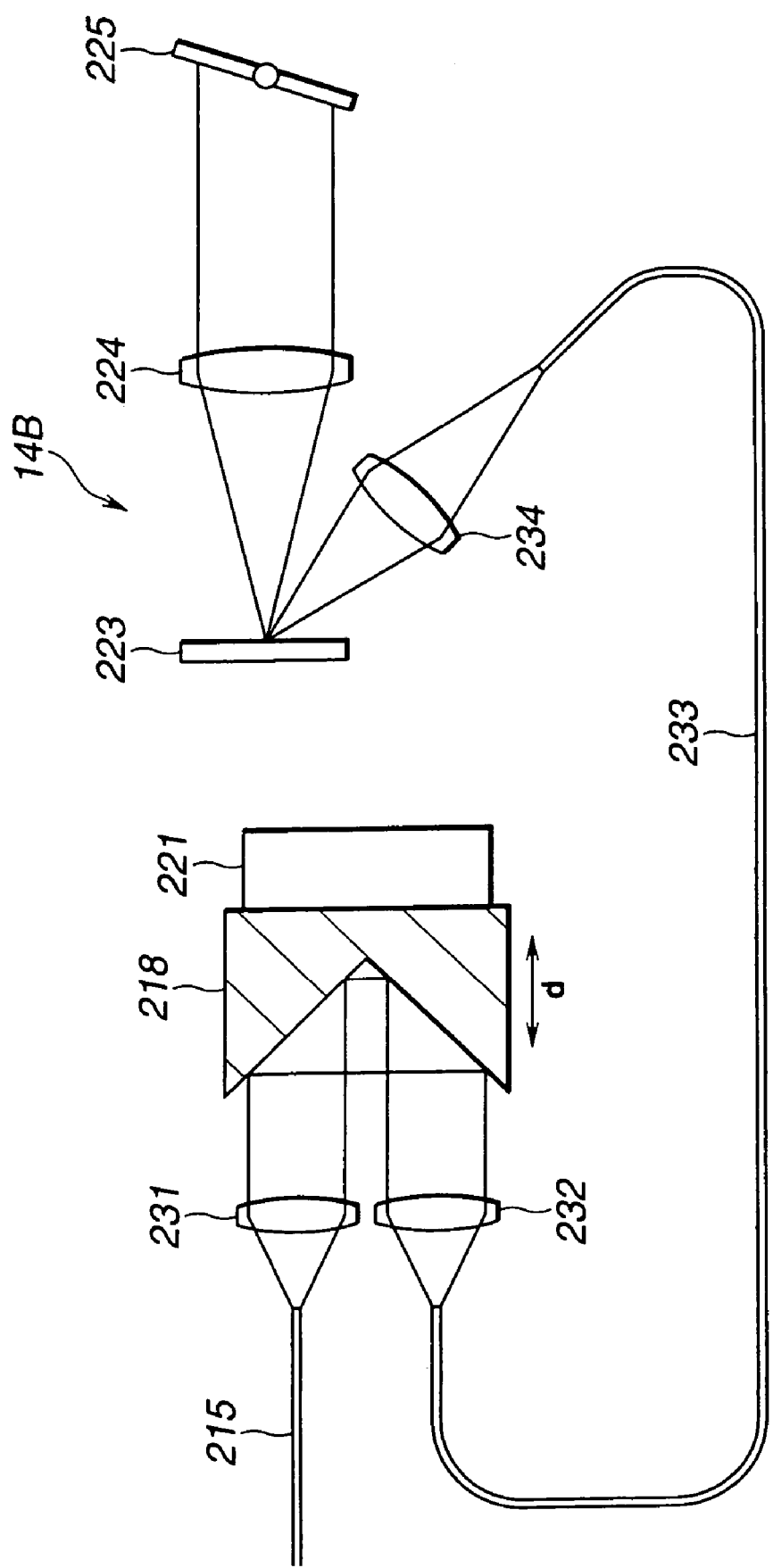

FIG. 24 illustrates the variable-length optical path mechanism 14B having the first optical path length changing mechanism and a second variable-length optical path mechanism. The light emitted from the second single mode fiber 215 is converted into parallel rays by the collimating lens 231, reflected twice from the corner mirror 218, and cast into the lens 232.

The corner mirror 218 is attached to a monoaxial slider 221, and changing the spacing between the reflecting mirror 217 and the corner mirror 218 allows the optical path length to be changed greatly.

The light cast into the lens 220 is reflected from a mirror 222, cast into grating 223, and the light split by the grating is cast into a galvanometer mirror 225 by an optical lens 224. The light reflected off of the galvanometer mirror 225 passes through the reverse optical path and is cast into the fifth single mode fiber 215.

The light delay time can be changed by scanning the galvanometer mirror 225. Other configurations are the same as those described with the first embodiment shown in FIG. 1.

Figure 25A:
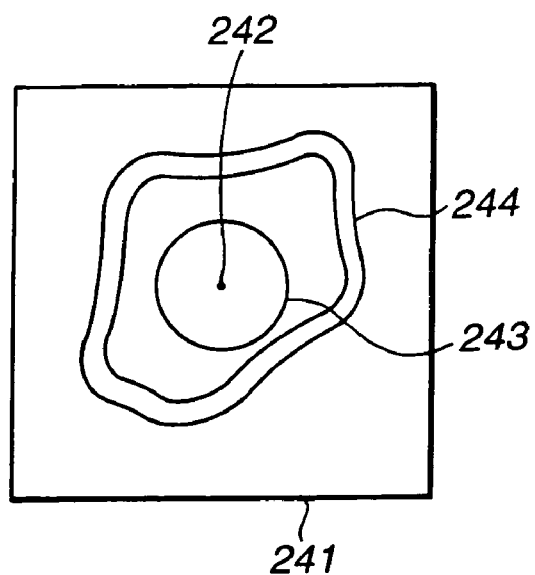
FIGS. 25A and 25B are diagrams illustrating a monitor image.

FIG. 25A shows an image obtained by the optical imaging apparatus according to the present embodiment.

A reflected image 243 of the environment at the outer side of the sheath, and an image 244 of the organic tissue is provided with the center of the monitor image 241 as the center thereof. The monitor center 242 corresponds with the rotational center of the optical probe 8.

Figure 25B:
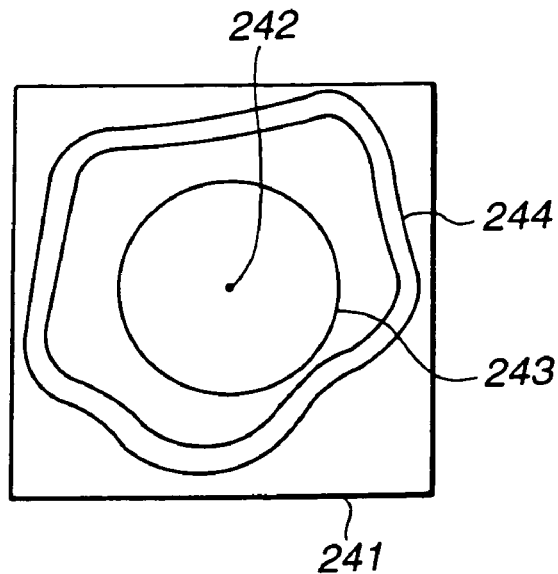

FIG. 25B indicates an image wherein the monitor center 242 and the rotational center of the optical probe 8 have shifted.

This occurs in the event that the optical path length of the fourth single mode fiber 10 and the lens unit 39 differs from the supposed length.

The diameter of the reflecting image 243 of the outer side of the sheath has increased, and the image 244 of the organism tissue has also enlarged. Accordingly, accurate diagnosis is difficult. Thus there is the need to calculate the optical path length accurately.

We can obtain reflection intensity while changing the optical path length using the variable-length optical path mechanism shown in FIGS. 23 and 24. We can obtain the relationships between the optical path length (distance), and the reflection intensity.

The reflection peak corresponding with the fiber end, the reflection at the incident end of the GRIN lens, at the incident end of the Faraday rotator, at the incident end of the prism, at the inner side of the sheath, at the outer side of the sheath, and the reflection at the organism tissue being measured. The intervals between the reflection peaks corresponds with the optical path lengths of the optical elements.

Figure 26:
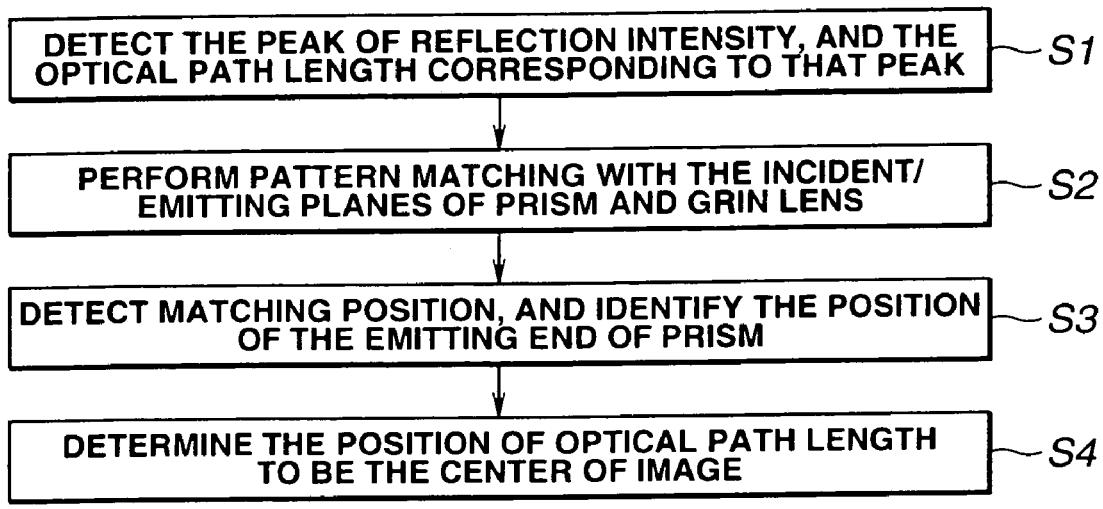

FIG. 26 illustrates a method for determining the position of the optical path length serving as the center of the image.

First, in step S1, the reflection intensity peak, and the optical path length corresponding to that peak are detected.

In the next step S2, patterning matching is performed with the optical path length of the prism and the incident/emission planes of the GRIN lens.

Next, in step S3, a matching position is detected, and the position of the emitting end of the prism is identified.

Next, in step S4, the position of the optical path serving as the center of the image is determined.

Figure 28:
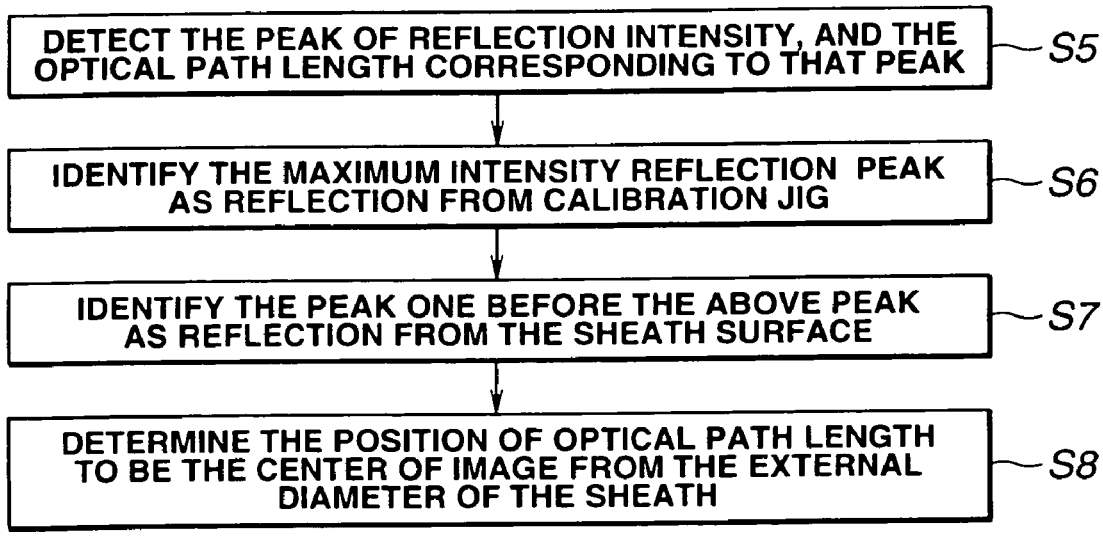
Figure 27:
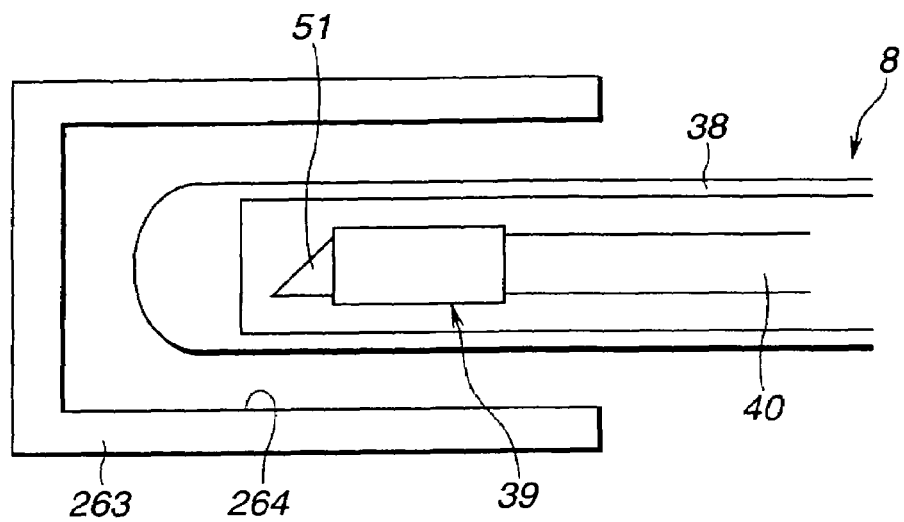

Also, FIGS. 27 and 28 illustrate another method for determining the position of the optical path serving as the center of the image.

As shown in FIG. 27, a calibration jig 263 is placed at the tip end of the optical probe.

This calibration jig 263 has a coating film 264 with high reflectance formed on the inside thereof.

Then, as shown in FIG. 28, in the first step S5, the peak of the reflection intensity and the optical path length peak corresponding with that reflection intensity are detected.

In the next step S7, the reflection peak of the maximum intensity is identified as the reflection from the calibration jig 263.

In the next step S8, the peak one before the above peak is identified as the reflection from the sheath surface.

Then, the next step S9, the position of the optical path length serving as the center of the image is determined from the outer diameter of the sheath.

Figure 29:
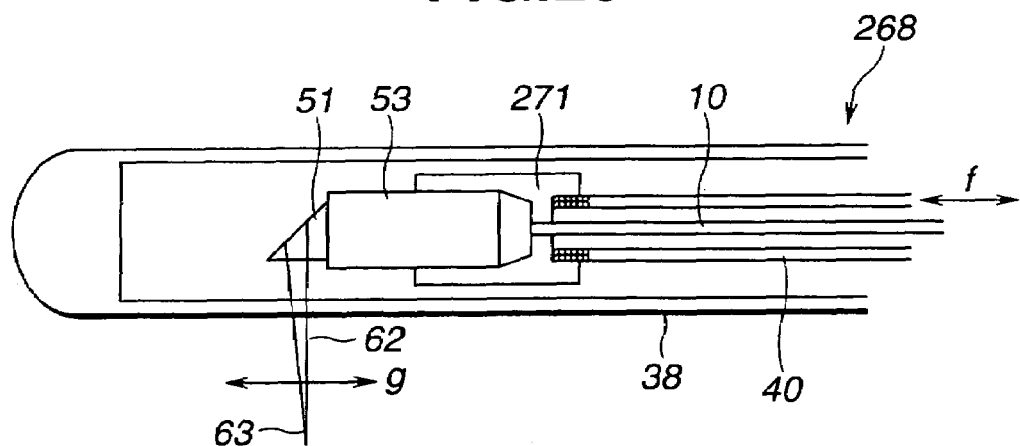

FIG. 29 illustrates an optical scanning probe which scans in the horizontal direction.

The flexible shaft 40, GRIN lens 53, prism 51, and the single mode fiber 10 are joined by the holding member 271. Scanning the flexible shaft in the horizontal direction f causes the observation beam 62 and the focal point 63 to be scanned in the horizontal direction g, thereby obtaining the image for scanning in the horizontal direction.

Figure 30:
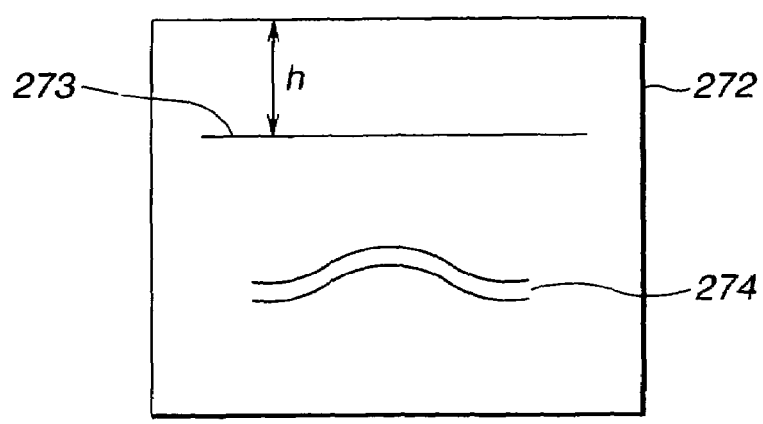

FIG. 30 shows the monitor image 272 obtained by the probe 268 shown in FIG. 29. The image 273 of the outer plane of the sheath and the image 274 of the organism tissue are obtained as the monitor image 272. The distance h between the top side of the monitor and the image 273 of the outer side of the sheath can calculate the optical length by the same method as that shown in FIGS. 27 and 28.

Figure 31:
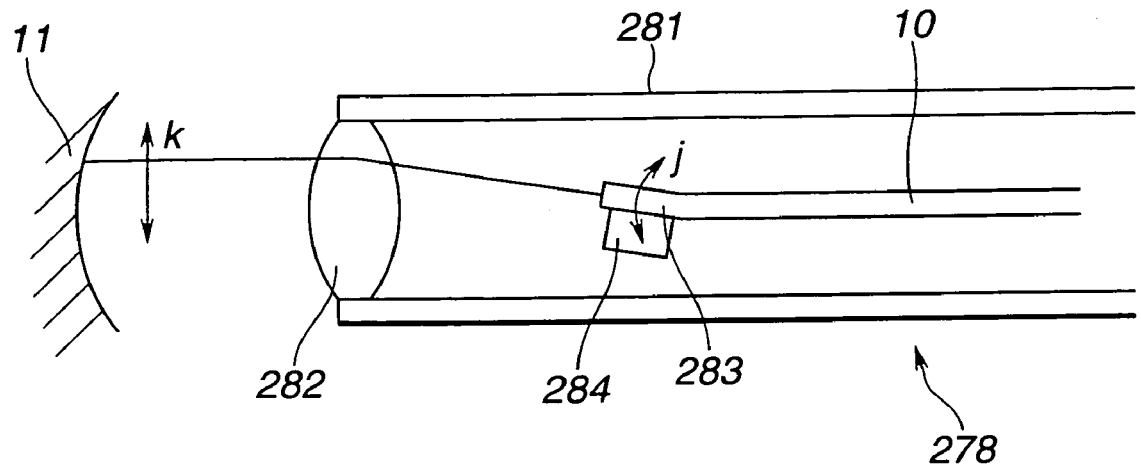

FIG. 31 indicates an optical scanning probe 278 which scans in the frontal direction of the probe.

The optical scanning probe 278 is arranged such that a single mode fiber 10 is positioned on the inner side of the sheath of the lens frame 281, and that light can be emitted through an object lens 282 attached to the tip opening of the lens face facing that tip plane.

Also, a piezoelectric device 284 or the like is attached to the tip portion of the single mode fiber 10, such that applying driving signals which change in level to the electrode of the piezoelectric device 284 via an unshown signal line scans the tip portion 283 in the vertical direction j, as shown in FIG. 31.

Scanning the tip portion 283 of the single mode fiber 10 in the vertical direction with this piezoelectric device 284 causes the observation beam to be scanned in the vertical direction k over the organism tissue 11, thereby obtaining an image of the organism tissue 11.

Figure 32:
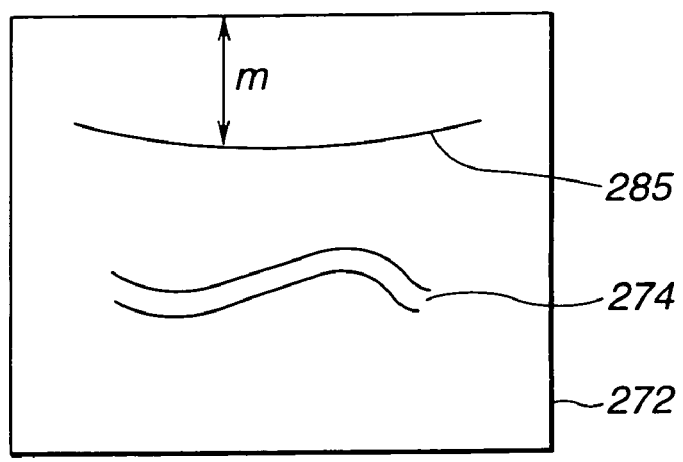

FIG. 32 shows an image obtained by the optical scanning probe shown in FIG. 31. An image 285 of the outer side of the sheath and an image 274 of the organism tissue 11 can be obtained as the monitor image 272. The distance m between the top side of the monitor and the image 285 of the outer side of the sheath can calculate the optical length by the same method as that shown in FIGS. 26 and 28.

Next, a ninth embodiment of the present embodiment will be described with reference to FIGS. 33 through 34B.

As shown in FIG. 33, the optical tomography apparatus 1B according to the present invention is comprised of a laser beam source 141 for supplying laser beams serving as guide beams for the wavelength in the visible area, facing the emitting end of the second single mode fiber 5, and a dichroic mirror 142 which transmits the laser beams, so that the low-coherence light emitted from the emitting end of the second single mode fiber 5 are reflected at the dichroic mirror 142 and received at the optical detector 12'.

Except for the configuration of the optical scanning probe 8H, the other configurations are the same as those of the first embodiment shown in FIG. 1, and accordingly description thereof will be omitted here.

Also, FIG. 34A shows the optical scanning probe 8H according to the present embodiment. The optical sheath 38 is formed of a cylindrical tube 151 and a tip cap 152 provided to the tip end thereof, with the convergence optical system being stored in the tip side of this sheath 38.

In other words, as shown in FIG. 34A, the arrangement is comprised of a second single mode fiber 10 which guides low-coherence light and guide light to the tip of the optical scanning probe 8H and returns reflected light from the subject, a GRIN lens 53 which converges the light comprised of low-coherence light emitted from the tip of the second single mode fiber 10 and guide light at a certain position, a rectangular dichroic mirror 154 which transmits the low-coherence light and selectively reflects the wavelength of the guide light, a Faraday rotator 52 which rotates the polarized plane of the low-coherence light, a micro prism which changes the optical path of the low-coherence light by reflection, and an optical system fixing member 155 which integrally fixes the GRIN lens 53, dichroic mirror 154, Faraday rotator 52, and micro prism 51.

The optical system fixing member 155 is a cylindrical form which has an opening according to the plane of the dichroic mirror 154 which reflects the guide light, and does not obstruct the optical path of the guide light. Also, the GRIN lens 53, second single mode fiber 10, and flexible shaft 40 through which the single mode fiber 10 is inserted and transmits rotational force, are fixed to a tip fixing member 156 which faces the GRIN lens at the tip thereof.

Next, the operation of the present embodiment will be described.

The subject side is illuminated from the illumination window at the tip portion of the insertion portion, by guiding illumination light from the endoscope light source device with the light guide of the endoscope. The illuminated subject is imaged on the solid image-taking element by the object optical system at the observation window, subjected to signal processing with the video processor, and displayed on the display monitor as an endoscope image.

In the event of displaying a monogram with the low-coherence light, the optical scanning probe 8H is passed through the forceps insertion opening of the endoscope, while watching the endoscope image, so that the tip portion of the optical scanning probe 8H protrudes from the opening of the endoscope tip side.

Then, low-coherence light is introduced from the low-coherence light source to the first single mode fiber 3. The first single mode fiber 3 is connected to the second single mode fiber 7 via the optical rotary joint 6, so as to guide the low-coherence light to the tip of the optical scanning probe 8H.

Also, one end of the second single mode fiber 5 is arranged so that guide light from a laser beam source 141 which emits light of a certain wavelength within the visible spectrum, is input thereto via the dichroic mirror. Accordingly, the guide light is transmitted through the dichroic mirror 142 and is cast into the one end of the second single mode fiber 5.

The second single mode fiber 5 is optically connected to the first single mode fiber 3 by the optical coupler 4, so the fourth single mode fiber 10 inserted through the optical scanning probe 8H guides the low-coherence light, and also guide light which has been synthesized with this low-coherence light.

The low-coherence light and guide light are guided by the fourth single mode fiber 10 and emitted to the opposing GRIN lens 53 side as shown in FIG. 34A, and converged by this GRIN lens 53. The guide light cast into the rectangular dichroic mirror 154 fixed to the tip plane of the GRIN lens 53 is emitted in a direction differing by 90 degrees by a dielectric multi-layer film formed within the dichroic mirror 154 so as to reflect the spectrum of the guide light, and is irradiated onto the subject.

Also, the low-coherence light cast into the dichroic mirror 154 is transmitted with no change, and is cast into the Faraday rotator 52. The low-coherence light which is transmitted through the Faraday rotator 52 has the polarized plane thereof rotated by 45 degrees, is cast into a micro prism 51 fixed to the tip of the Faraday rotator 52, and is totally reflected from the inclined plane thereof such that the direction thereof has changed by 90 degrees and emitted in the same direction as the dichroic mirror 154. The low-coherence light emitted from the micro prism is irradiated onto the subject.

The low-coherence light and guide light irradiated onto the subject is reflected at the surface of the subject and at inner tissue portions near the surface thereof which have differing optical properties, and scattered within the tissue, and a part of the light is cast into the fourth single mode fiber 10 through the optical path reverse to irradiation, and is transmitted to the rear end side thereof.

Then, this light is cast into the tip plane of the first single mode fiber 3 via the rotary joint 6 and a portion of the light shifts to the second single mode fiber by the optical coupler 4 located partway on the optical path.

Here, the low-coherence reflected light is mixed with the light reflected by the galvano mirror 19.

Of the light emitting from the rear end of the second single mode fiber 5, only the guide light is transmitted through the dichroic mirror 142, and the other components are reflected and cast into a photo detector 12'.

The light cast into this photo detector 12' is subjected to photoelectric conversion, thereby forming electric signals. Only the low-coherence light component of these signals is extracted and detected. Then, the signals are converted into digital signals and input to the computer 25.

The computer 25 obtains tomogram data in the depth direction of the subject by changing the optical path length with the variable-length optical path mechanism 14, and also controls the rotation riving device 13 so as to rotate an unshown motor within the optical rotary joint 6, thereby obtaining one frame of tomography data.

The computer 25 temporarily stores the tomography data sequentially obtained in the memory thereof, and reads this out at certain cycles so as to display the tomogram on the monitor 26.

The technician judges the position of the tomogram being observed from the irradiation position of the guide light displayed on the endoscope image, and moves the optical scanning probe 8H to the desired position to obtain the necessary tomogram.

Though the irradiation positions of the guide light and the low-coherence light on the subject differ slightly, this offset is only several millimeters, and accordingly does not pose a problem for positioning the optical scanning probe 8H.

Also, as shown in FIG. 34B, changing the angle of the dielectric multi-layer film from 45 degrees, and using the rectangular dichroic mirror 156 with a reflection angle greater than 90 degrees, enables better matching at the irradiation position of the low-coherence light.

Also, according to the present invention, the dichroic mirrors 154 and 156 are described as being rectangular, but the form is not restricted to such.

Thus, according to the present embodiment, guide light alone is reflected from the subject before the guide light is cast into the Faraday rotator 52, thereby enabling irradiation of the guide light to the subject, meaning that the optical scanning probe 8H can be scanned at a desired position while observing the endoscope image, thus obtaining the needed tomogram.

According to the sixth through ninth embodiments as described above, an optical scanning probe device for use in an optical imaging apparatus for irradiating low-coherence light onto a subject and constructing a cross-section image of a subject, based on information from the light scattered at the subject, comprises:

a sheath, the greater portion thereof being formed of a flexible resin tube with at least the tip thereof being formed of a material with good light transmittance; and a light emission/incident light unit provided on the inner side of the portion of the sheath formed of a material with good light transmittance, for emitting light to the inner side of the sheath and irradiating the transmitted light onto the external subject, and for casting in and transmitting reflection/scattering/excitation light from the subject through wherein at least the portion provided with the light emission/incident light unit is exchangeable, so that in the event that the inner plane of the sheath is scratched, observation can be made by replacing the scratched sheath alone.

Next, description will be made regarding a tenth embodiment having a variable-length optical path mechanism whereby the scanning range can be widened at high speeds.

First, the principle of the variable-length optical path will be described.

Figure 35:
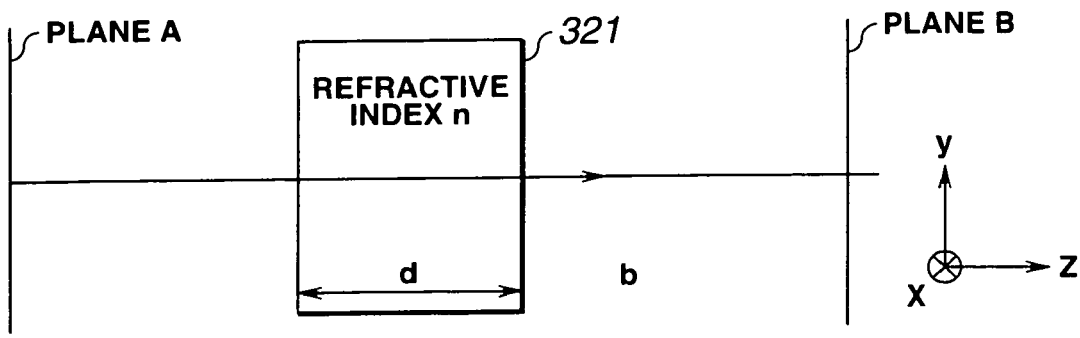
FIGS. 35 through 40 relate to a tenth embodiment of the present invention, with FIG. 35 being a first explanatory diagram for describing the principle for the variable-length optical path optical system.

As shown in FIG. 35, let us say that parallel light is emitted perpendicularly from a plane A, passes through a parallel flat glass plate 321 with a thickness of d, and reaches a plane B parallel with the plane. A. The parallel flat glass plate 321 is arranged so as to rotate with a line parallel to the X-axial direction as the axis thereof. Here, the direction of the light emitted from the plane A is the Z-axis, and the directions perpendicular to the Z axis are the X-axis and Y-axis.

Figure 36:
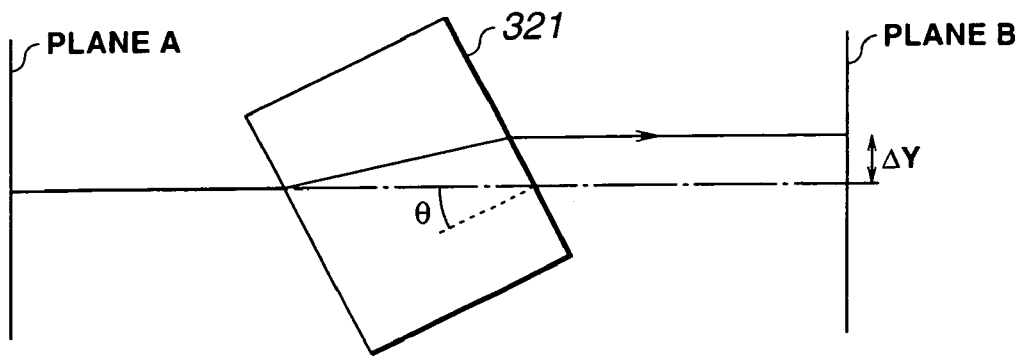

Let us say that the inclination of the parallel flat glass plate 321 to the normal line Z-axis is simply the inclination of the parallel flat glass plate 321. In the event that the inclination of the parallel flat glass plate 321 is zero, the light is not refracted and proceeds straight as shown in FIG. 35, but in the event that the parallel flat glass plate 321 is inclined, the light is refracted at the plane of incidence and the plane of emergence of the parallel flat glass plate 321, as shown in FIG. 36. At this time, the plane of incidence and the plane of emergence of the parallel flat glass plate 321 are parallel, so though the light before being cast into the parallel flat glass plate 321 and the light following emerging from the parallel flat glass plate 321 shift in the Y-axial direction, the light rays are parallel.

With the optical path length L(0) of the distance of light emitted from the plane A to the plane B as a reference in the event that the inclination of the parallel flat glass plate 321 is zero, the optical path length L($\theta$) of the distance of light emitted from the plane A to the plane B in the event that the inclination of the parallel flat glass plate 321 is ($\theta$) has the following relation:

$$L(\theta)=L(0)+d\{1-n-\cos\theta+(n^2-\sin^2\theta)^{1/2}\} \quad (1)$$

Accordingly, the optical path length difference $\Delta L$ in the event that the angle of the normal line of the parallel rays and the parallel flat glass plate 321 is zero and $\theta$ is as follows:

$$\Delta L = L(\theta) - L(0) \quad (2)$$
$$= d\{1 - n - \cos\theta + (n^2 - \sin^2\theta)^{\frac{1}{2}}\}$$

Also, the shift amount $\Delta Y$ in the Y-axial direction following passage through the parallel flat glass plate as compared to the rays before passing through the parallel flat glass plate 321 is as follows:

$$\Delta Y=d\cdot\sin\theta\{1-\cos\theta/(n^2-\sin^2\theta)^{1/2}\} \quad (3)$$

Thus, changing the inclination of the parallel flat glass plate 321 as to the light rays allows the optical path length to be changed, but in the event that only one parallel flat glass plate 321 is used, the light ray shifts in the Y-axial direction (referred to as Y-directional shift). However, the Y-directional shift of the rays can be cancelled by causing the rays to pass through parallel flat plates with equal refractive indexes and thickness, an even number of times.

Figure 37:
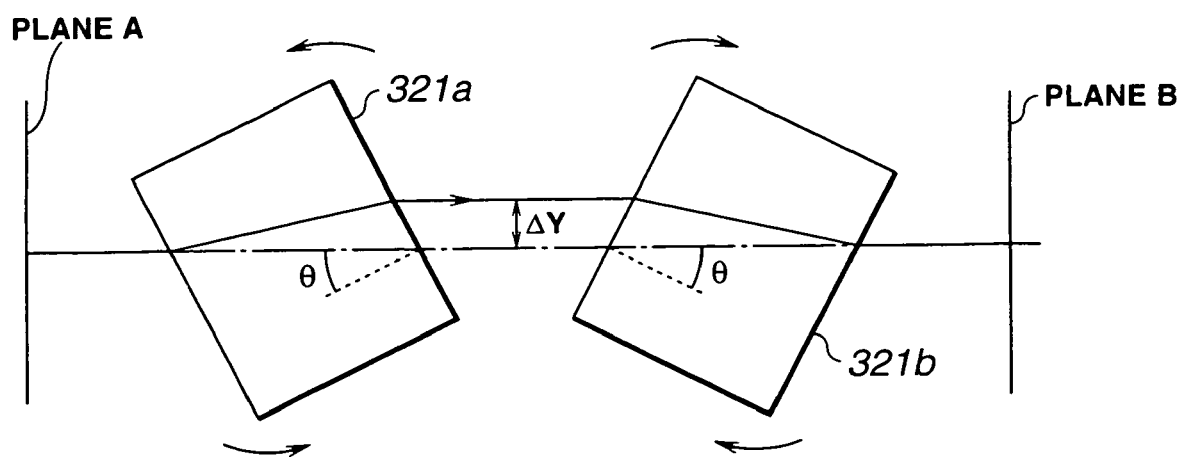

FIG. 37 is a specific illustrating of the configuration of this method. Parallel light beams are cast out in a perpendicular direction from the plane A, and the emitted parallel light passes through the first parallel flat glass plate 321a and second parallel flat glass plate 231b, and thus reaches the plane B. The first parallel flat glass plate 321a and second parallel flat glass plate 231b have equal refractive indexes and thickness, and the first parallel flat glass plate 321a and second parallel flat glass plate 231b are arranged so as to incline or rotate in opposite directions with the same phase.

That is, at the time that the first parallel flat glass plate 321a is inclined at an angle $\theta$ as to the incident light, the second parallel flat glass plate 321b is inclined at the angle of $-\theta$. Accordingly, though the light is $\Delta Y$ shifted in the Y-axial direction after passing through the first parallel flat glass plate 321a, it is $-\Delta Y$ shifted in the Y-axial direction by passing through the second parallel flat glass plate 321b, so regardless of the inclination of the first parallel flat glass plate 321a and second parallel flat glass plate 231b, the Y-direction shift of the light rays before passing through the first parallel flat glass plate 321a and after passing through the second parallel flat glass plate 231b is always zero.

At this time, the light passes through parallel flat glass plates twice, so the optical path length difference ΔL in the event that the inclination of the parallel flat glass plate 321a and 213b is zero and θ (at this time, the inclination of the first parallel flat glass plate 321a is θ, and the inclination of the second parallel flat glass plate 321b is −θ) is as follows:

$$\Delta L = 2d\{1 - n - \cos\theta + (n^2 - \sin^2\theta)^{1/2}\} \quad (4)$$

Here, the light only passes through the parallel flat glass plates twice, but arranging such an optical system in a series so that the light passes through the parallel flat glass plate an even number of times does away with Y-directional shifting.

Also, introduction of light to the variable-length optical path and extraction of light from the variable-length optical path is readily performed using single mode optical fiber. Accordingly, single mode optical fiber is used for introduction of light to the variable-length optical path and extraction of light from the variable-length optical path in endoscopes, since effects of air turbulence and the like do not easily occur.

In the event of using single mode optical fiber for the variable-length optical path introduction and variable-length optical path extraction, a positive power collimating lens is used for making the light from the introducing single mode optical fiber, and a positive power converging lens is used for extracting the parallel light and combining at the extracting optical fiber.

The present embodiment is based on such a principle, and a configuration allows the optical path to be changed in length without changing the position of incident angle cast into the extracting single mode fiber and the incident angle thereto, so an extremely stable variable-length optical path optical system can be configured. Also, the parallel flat glass plates can be rotated at high speeds by matching the inertia axis and the rotation axis, thereby allowing tomograms of the organism to be observed in motion.

The tenth embodiment will be described with reference to FIGS. 38 through 40.

Figure 38:
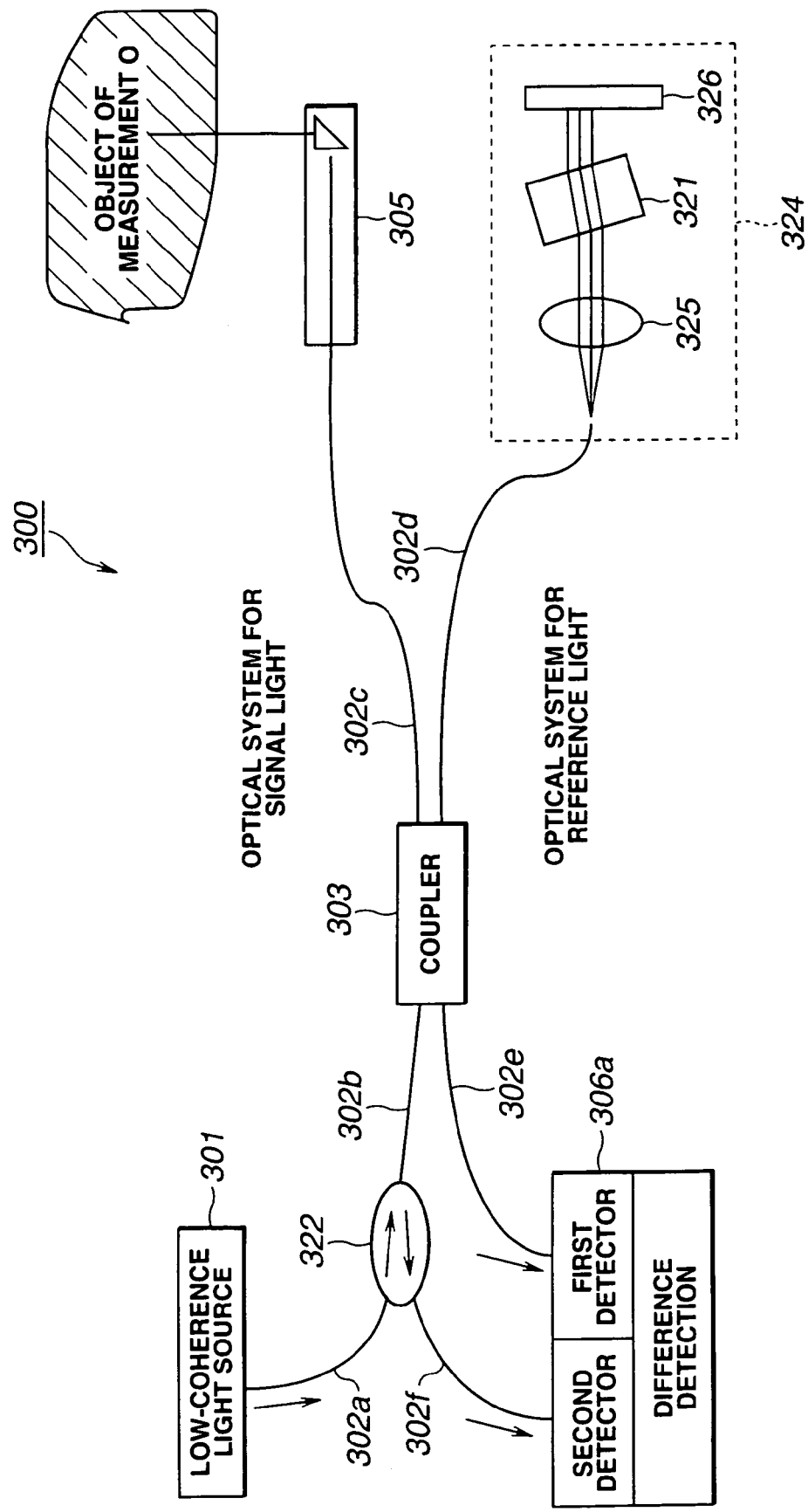

The optical imaging apparatus 300 according to the tenth embodiment shown in FIG. 38 is based on a Michelson interferometer.

In this embodiment, the light from a low-coherence light source 301 passes through a first single mode optical fiber 302a and passes through an optical circulator 322, and is guided to a coupler 303 via a second single mode optical fiber 302b. The light is split into the signal light side and reference light side at the coupler 303.

The light at the signal light side passes through a third single mode optical fiber 302c and a signal light side tip optical system 305 to be irradiated on the object O, and the light returning from the object passes through the signal light side tip optical system 305 and third single mode optical fiber 302c, and returns to the coupler 303.

On the other hand, the light from the reference light side split at the coupler 303 passes through a fourth single mode optical fiber 302d to reach a variable-length optical path optical system 324. Then, the light subjected to change in the optical path length in the variable-length optical path optical system 324 passes through the fourth single mode optical fiber 302d and returns to the coupler 303.

The light returning from the signal light side and the light returning from the reference light side are synthesized at the coupler 303. The interference signals synthesized at the coupler 303 are split into the fifth single mode optical fiber 302e for a first detector 306a side, and the second single mode optical fiber 302b for an optical circulator 322.

The light which heads to the fifth single mode optical fiber 302e for a first detector 306a side passes through the fifth single mode optical fiber 302e, and optical intensity detection is performed at the first detector 306a. On the other hand, the light which heads to the second single mode optical fiber 302b for the optical circulator 322 side is selectively guided to the sixth single mode optical fiber at the optical circulator 322, and optical intensity detection is performed at the second detector 306b.

The first detector 306a and second detector 306b form a difference detector for detecting difference, so only interference signal components are output, and other components are removed.

Figure 39:
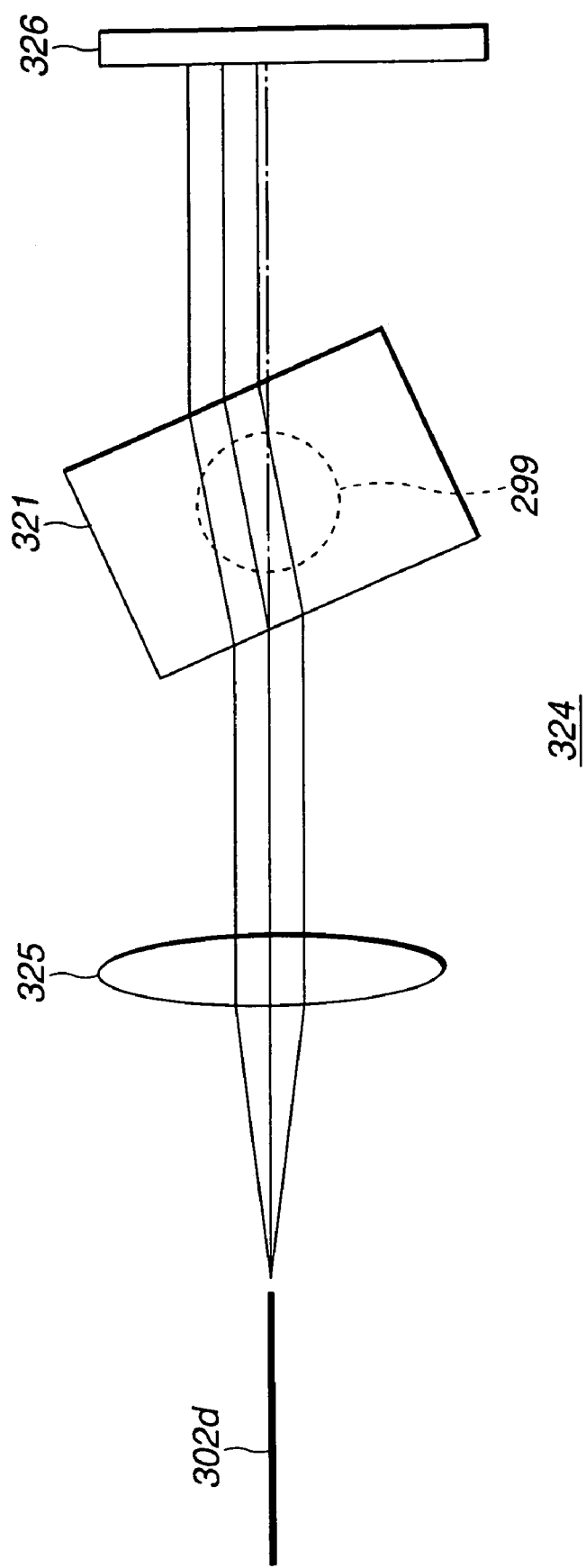
Figure 40:
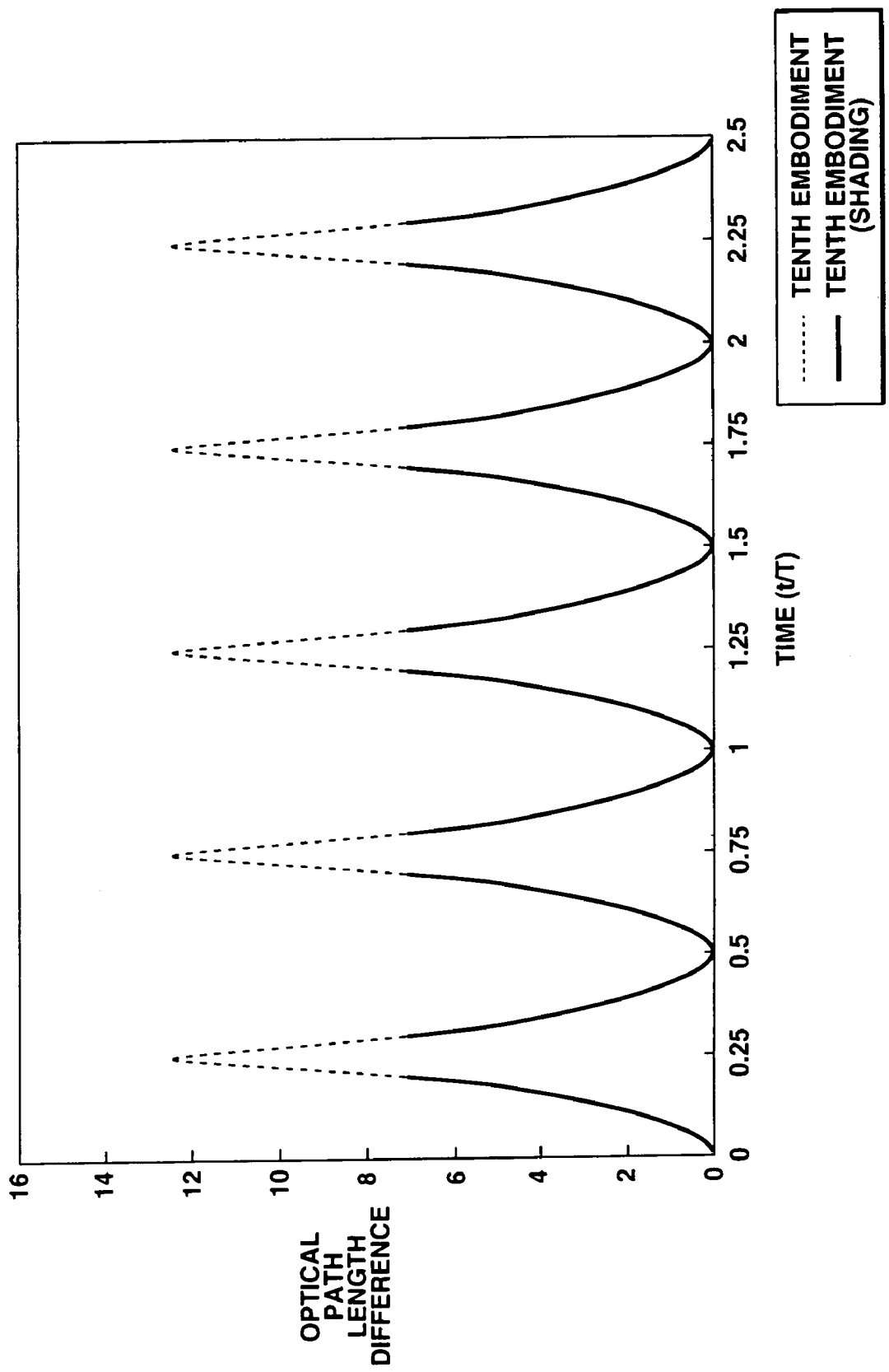

As shown in FIG. 39, the variable-length optical path optical system 324 is comprised of a single mode optical fiber (fourth single mode optical fiber) 302d serving both as an introducing single mode optical fiber and extracting single mode optical fiber, a positive lens 325 serving both as a collimator lens and converging lens, a parallel flat glass plate 321 having mutually parallel planes, and a flat mirror 326 for reflecting the light back in the direction from whence it came.

The optical axis of the single mode optical fiber 302d, positive lens 325, and flat mirror 326 are matched such that the light cast from the single mode optical fiber. 302d is made generally parallel at the positive lens 325, which passes through the parallel flat glass plate 321, and further through the positive lens 325, then returning to the single mode optical fiber 302d.

Then, the parallel flat glass plate 321 is attached to the rotating axis of a motor 299 rotating with the axis of rotation perpendicular to the optical axis, so that the optical path length of the light emerging from the single mode optical fiber 302d and then returning to the single mode optical fiber 302d is changed.

Incidentally, as described in the later-described twelfth embodiment, the parallel flat glass plate 321 may be made to oscillate (rotationally vibrate) instead of rotating. This can also be applied to other embodiments and variations.

In the present embodiment, the light passes through the parallel flat glass plate 321 an even number of times, so the position of the light returning to the single mode optical fiber 302d is not changed by the parallel flat glass plate 321.

The difference ΔL between the optical path length in the event that the normal line of the parallel planes of the parallel flat glass plate 321 is 0 and the optical path length in the event that the angle is θ is:

$$\Delta L = 2d\{1 - n - \cos\theta + (n^2 - \sin^2\theta)^{1/2}\} \quad (5)$$

wherein n and d are the reflective index of the parallel flat glass plate 321 and thickness of the parallel flat glass plate 321, respectively.

According to the configuration of the present embodiment, rotating the parallel flat glass plate 321 at a cycle T results in the optical path length difference ΔL (t) at a time t being:

$$\Delta L(t) = 2d\{1 - n - |\cos(2\rho t/T + \phi)| + \{n^2 - \sin^2(2\pi/T + \phi)\}^{1/2} \quad (6)$$

wherein φ represents the inclination of the parallel flat glass plate 321 in the event that t=0. The dotted line in FIG. 40 represents the time difference of the optical path length in the event that the parallel flat glass plate 321 has a refractive index of 1.5 and thickness of 10 mm, and is rotated at a cycle T.

In practice, in the event that the angle of the parallel flat glass plate 321 increases, there is a limit to the size of the parallel flat glass plate 321, so there is time that light is rejected and not passed, and thus the optical path length difference behaves like the solid line.

Next, a first variation of the tenth embodiment will be described with reference to FIGS. 41A through 42.

Figure 41A:
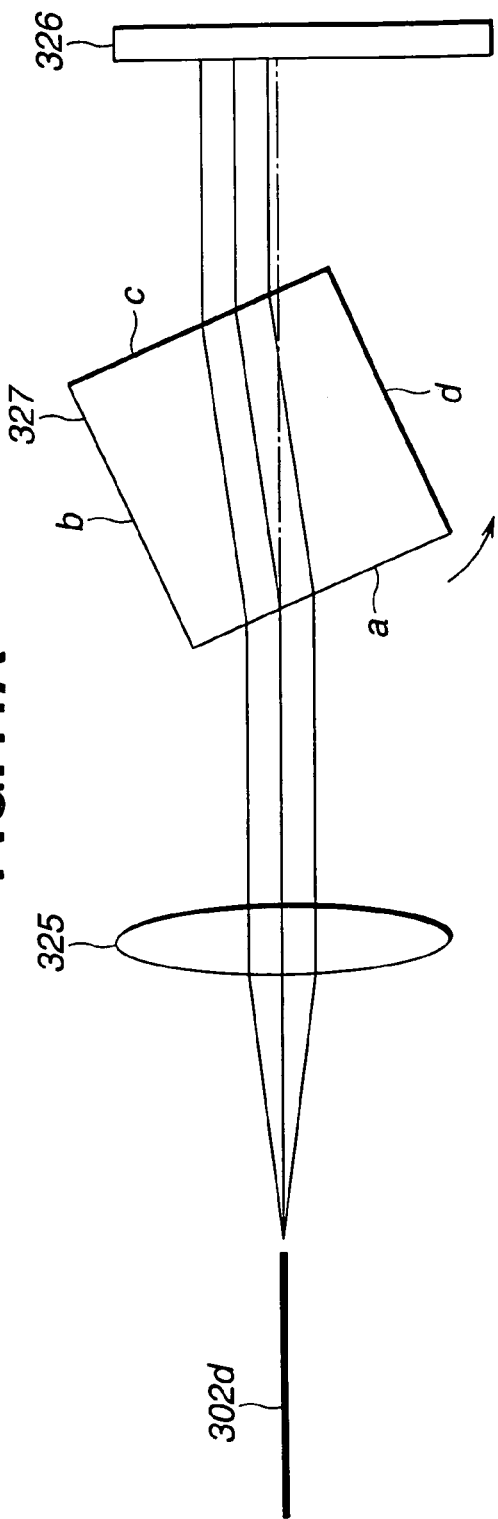
FIGS. 41A and 41B are configuration diagrams illustrating the variable-length optical path optical system acquiring to a first variation example of the tenth embodiment.
Figure 41B:
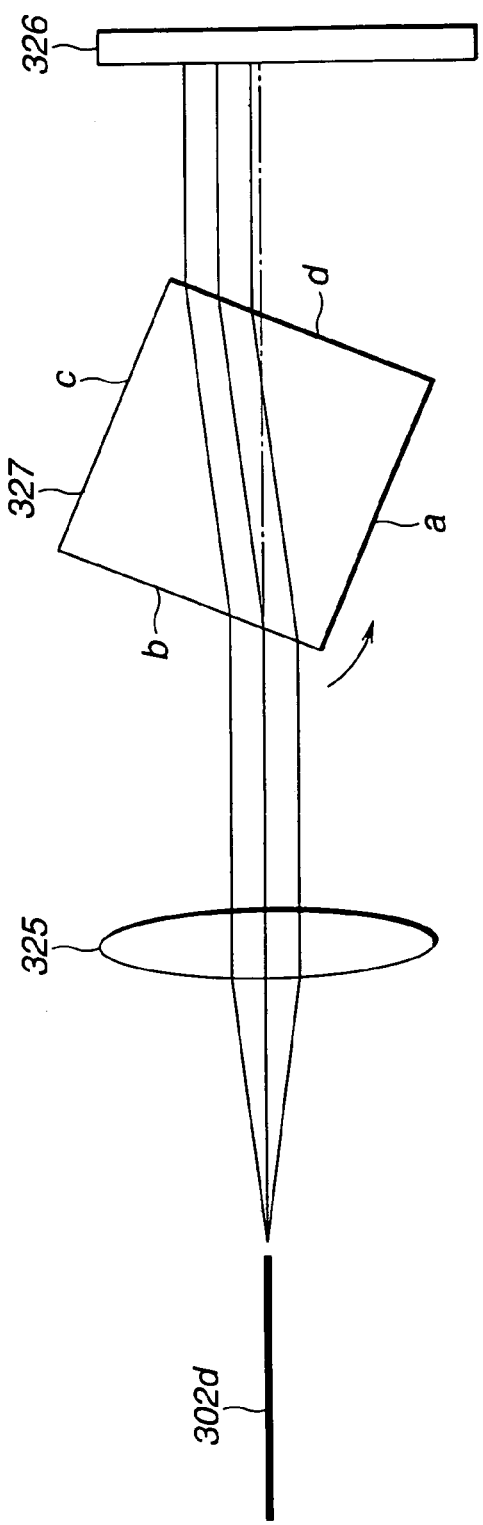

FIG. 41A represents the variable-length optical path optical system of a first variation, with FIG. 41B being a diagram showing the glass block in FIG. 41A being rotated by several tens of degrees. The only thing that has been changed in the first variation is the variable-length optical path optical system 324, and the other unshown members are the same as the tenth embodiment, including the interferometer.

With the present embodiment, the parallel flat glass plate 321 in the variable-length optical path optical system 324 in the tenth embodiment has been replaced with a glass block 327 having a square cross-section. Also, the dotted line A in FIG. 43 illustrates the time difference of the optical path length difference at the time that a glass block 327 with a refractive index of 1.5 and a thickness (the length of one side of the cross-sectional square) of 10, being rotated at a cycle T. Using the glass block 327 with a square cross-section, such as in the present embodiment, allows the time wherein the light beam is not passable to be reduced. That is, in the tenth embodiment, as the inclination angle of the parallel flat glass plate 321 nears 90 degrees, the light is rejected by the side plane of the parallel flat glass plate 321, so there is a long time wherein light does not pass.

On the other hand, with the present embodiment, as shown in FIG. 41A, even in the event that the glass block 327 rotates from the initial state wherein light passes through the plane a and the plane c of the glass block 327, so that light no longer passes through the plane a and the plane c, the light passes through the plane b and the plane d, so the light can be constantly passed through except for the instant that the apex of the glass block 327 rejects the light flux.

Also, according to the tenth embodiment, only two reciprocal scans could be made per rotation of the parallel flat glass plate 321, the present variation is advantageous in that the number of scans can be increased to four reciprocal scans. Also, though the present variation has the cross-section of the glass block 327 as a square, the scanning cycle of the optical path length can be reduced even without increasing the rotational speed of the glass block.

Next, the second variation will be described with reference to FIGS. 43A and 43B. The only thing that has been changed in the second variation is the variable-length optical path optical system 324, and the other unshown members are the same as the tenth embodiment, including the interferometer.

FIGS. 43A and 43B are diagrams illustrating the variable-length optical path optical system according to the second variation, with FIG. 43A being a diagram viewing the variable-length optical path optical system from the Y-axial direction and FIG. 43B from the X-axial direction, with the optical axis of the single mode optical fiber 302d as the Z-axis.

The variable-length optical path optical system according to the present variation is comprised of a single mode optical fiber (fourth single mode optical fiber) 302d serving both as an introducing single mode optical fiber and extracting single mode optical fiber, a positive lens 325 serving both as a collimator lens and converging lens, a glass block 327 with a square cross-section to serve as an optical element having mutually parallel sides, a roof mirror 328 which is an optical path deviating element for shifting the position of incident light and emitting the light in the opposite direction, and a flat mirror 326 for reflecting the light back in the direction from whence it came.

The roof mirror 328 is formed of two reflecting planes joined at right angles, and the light cast into this roof mirror 328 is shifted in the X-axial direction, and also the diffraction is reversed and emitted.

The present variation behaves as follows. The light cast from the single mode optical fiber 302d is made generally parallel at the positive lens 325, which passes through the glass block 327, and then is subjected to direction reversal in the −Z direction by the roof mirror 328 and also receives a shift in the X-axial direction.

The light which has exited the roof mirror 328 passes through the same glass block 327 again, and reaches the flat mirror 326. The light reaching the flat mirror 326 is reflected in the opposite direction and proceeds down the path from whence it came in the opposite direction, finally returning to the single mode optical fiber 302d. The expression "the path from whence it came" here refers to the path passing through the glass block 327, roof mirror 328, glass block 327, and positive lens 325, to reach the single mode optical fiber 302d.

The optical path length changes by rotating the glass block 327 on an axis parallel to the X-axis. In the present embodiment, the light passes through the glass block 327 having parallel planes an even number of times, so the light returning to the single mode optical fiber 302d can be made to be stationary in position even when the glass block 327 rotates.

Also, according to the first variation, the light emitted from the single mode optical fiber 302d and returning thereof only passes twice through the glass block 327 capable of changing the optical path length, but the light passes through the glass block 327 four times with the present embodiment, so in the event that a glass block 327 with the same refractive index and size as the first variation is used, the difference in optical path length is twice that of the first variation.

The solid line B in FIG. 42 illustrates the optical path length difference over time, while the glass block 327 with a refractive index of 1.5 and a thickness (the length of one side of the cross-sectional square) of 10 is being rotated at a cycle T. It can be understood that the optical path length difference is twice that of the first variation.

The scanning width of the optical path length can be increased by using an optical path deviating element such as the roof mirror 328 to pass the light multiple times through the optical element with parallel planes.

Though a roof mirror 328 was used with the present embodiment as the optical path deviating element, any object capable of shifting the position of incident light and reversing the emission direction thereof, such as a prism or the like, may be used as the optical path deviating element.

Next, the eleventh embodiment of the present invention will be described with reference to FIGS. 44 through 46.

Figure 44:
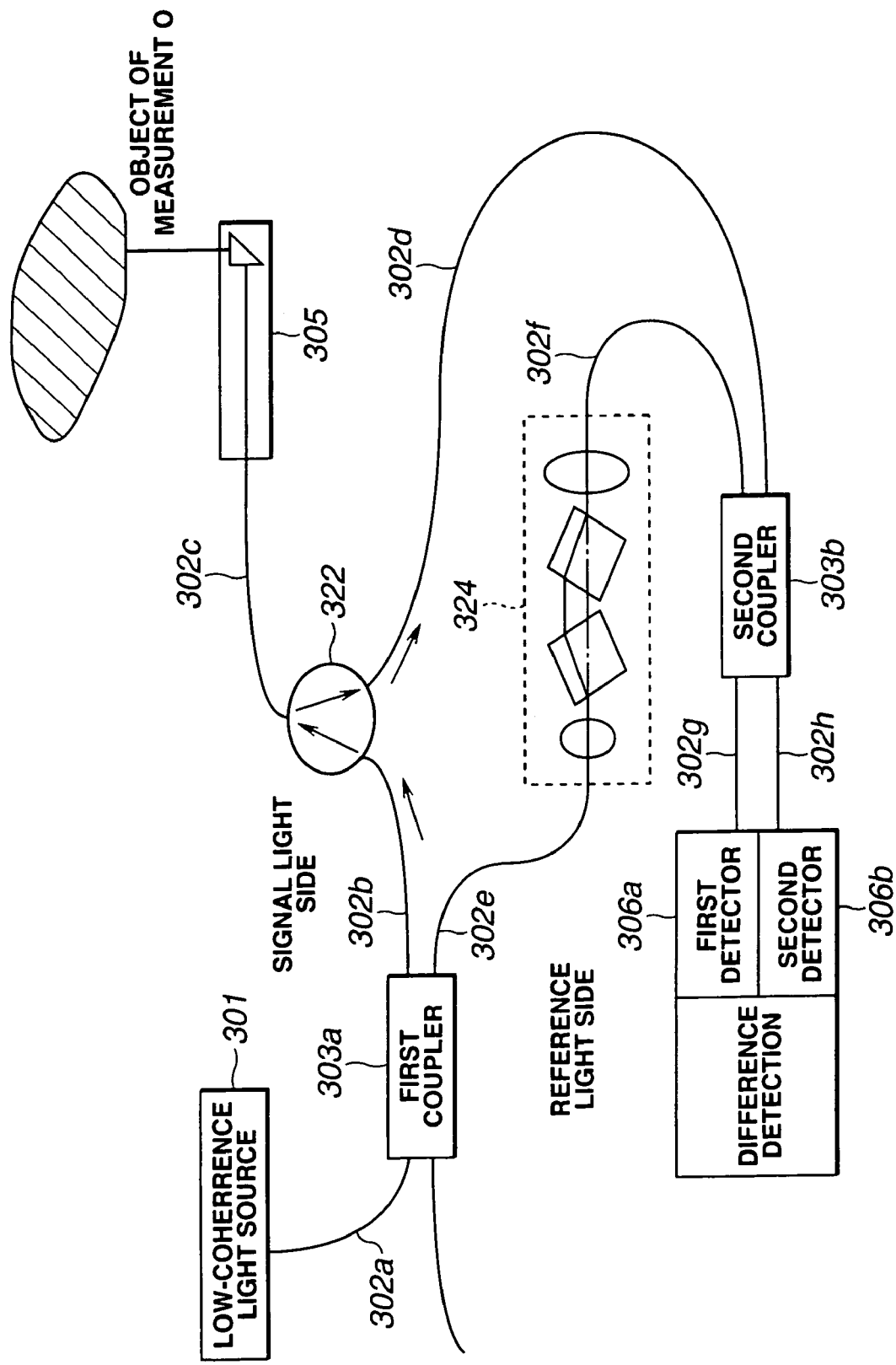
FIG. 44 is a configuration diagram illustrating the optical imaging apparatus according to the eleventh embodiment.

The optical imaging apparatus according to the eleventh embodiment of the present invention shown in FIG. 44 is based on a Mach-Zehnder interferometer.

According to the present embodiment, the light emitted from the low-coherence light source 301 passes throughout the first single mode optical fiber 302a and is guided to the first coupler 303a. The light is split into the signal light side and reference light side at the coupler 31.

The light at the signal light side passes through the second single mode optical fiber 302b and an optical circulator 322, and then further through the third single mode optical fiber 302c and signal light side tip optical system 305, to be irradiated on the object O.

The light returning from the object O passes through the signal light side tip optical system 305 and third single mode optical fiber 302c, and returns to the optical circulator 322. The light at the signal light side which has returned to the optical circulator 322 is selectively guided to the fourth single mode optical fiber 302d connected to the second coupler 303b.

On the other hand, the light from the reference light side split at the coupler 303a passes through a fifth single mode optical fiber 302e for guiding to the variable-length optical path optical system 324, to reach the variable-length optical path optical system 324. Then, the light subjected to change in the optical path length in the variable-length optical path optical system 324 passes through the sixth single mode optical fiber 302f for extraction, and is guided to the second coupler 303b.

The light guided from the signal light side and the light guided from the reference light side are synthesized at the second coupler 303b, and the interference signals synthesized at the coupler 303b are guided to the first detector 306a and the second detector 306b, by the seventh and eighth single mode optical fibers 302g and 302h. Optical intensity detection is performed at the first detector 306a and the second detector 306b.

The first detector 306a and second detector 306b form a difference detector for detecting difference, so only interference signal components are output, and other components are removed.

Figure 45:
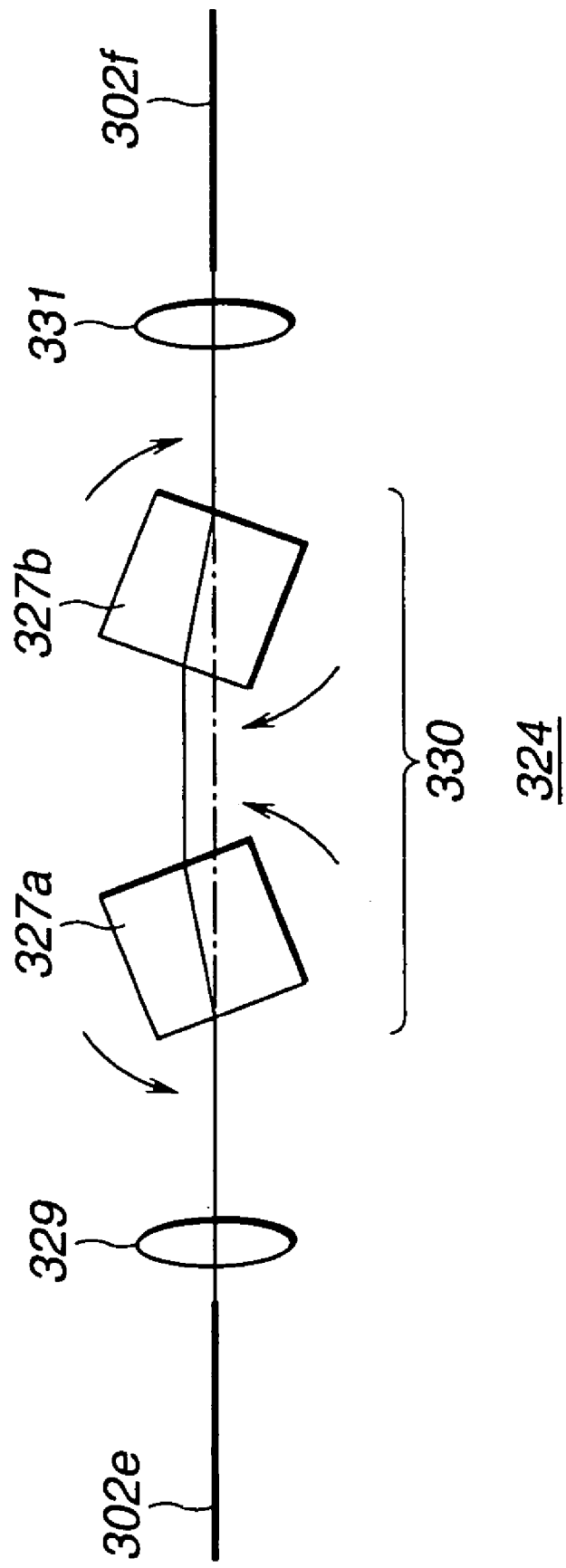
FIG. 45 is a configuration diagram of the variable-length optical path optical system according to the eleventh embodiment.

As shown in FIG. 45, the variable-length optical path optical system 324 is formed of an introducing single mode optical fiber 302e for introducing light to the optical system, a collimator lens 329 for collimating light from the introducing single mode optical fiber 302e, a variable-length optical path optical element group 330, a converging lens for converging parallel light, and an extracting single mode optical fiber 302f for extracting light, in that order.

Also, with this optical system, the introducing single mode optical fiber 302e, collimator lens 329, converging lens 331, and extracting single mode optical fiber 302f are arranged so that the optical axis matches, so the light emitted from the introducing single mode optical fiber 302e passes through the collimator lens 329 and converging lens 331, and is cast into the extracting single mode optical fiber 302f.

Also, the variable-length optical path optical element group 330 has two glass blocks 327a and 327b, with exactly the same refractive index and form. The glass blocks 327a and 327b each have square cross-sections with two sets of parallel planes.

The glass blocks 327a and 327b of the variable-length optical path optical element group 330 are configured to be rotated in mutually opposing directions at the same angle, whereby the optical path length between the introducing single mode optical fiber 302e and the extracting single mode optical fiber 302f can be changed without the converging position of light at the extracting single mode optical fiber 302f shifting.

According to the present embodiment, the difference ΔL of the optical path length in the event that the normal line of the mutually parallel planes of the glass blocks 327a and 327b is 0 and θ as to the optical axis is:

$$\Delta L = 2d\{1 - n - \cos\theta + (n^2 - \sin^2\theta)^{1/2}\} \quad (7)$$

wherein −45°<θ<45° holds, n and d are the reflective index of the glass blocks 327a and 327b, and thickness of the square cross-section of the glass blocks 327a and 327b, respectively.

The dotted line A in FIG. 46 illustrates the time elapsing of the optical path length difference at the time that the glass blocks 327a and 327b with a refractive index of 1.8 and a thickness of 10 are rotated at a cycle T.

Next, a first variation of the eleventh embodiment will be described with reference to FIGS. 47B and 47B. With the first variation in FIGS. 47A and 47B, the only thing that has been changed from the eleventh embodiment is the variable-length optical path optical system, and the other unshown members are the same as the tenth embodiment, including the interferometer.

FIG. 47A is a diagram viewing the variable-length optical path optical system from the Y-axial direction and FIG. 47B from the X-axial direction, with the optical axis of the single mode optical fibers 302e and 302f as the Z-axis.

The variable-length optical path optical system according to the present embodiment is formed of an introducing single mode optical fiber 325 for guiding light from the first coupler 303a (see FIG. 44) to the variable-length optical path optical system 324, a first GRIN lens (refractive index distribution lens) serving as a collimator lens, a glass block 327 with a square cross-section serving as an optical element having mutually parallel planes, an optical path deviating prism 333 serving as an optical path deviating optical element which shifts the position of the incident light and emits the light in the opposite direction, a second GRIN lens serving as a converging lens, and an extracting single mode optical fiber 302f for extracting light. The glass block 327 rotates on an axis which is parallel to the X-axis.

The cross-sectional form of the optical path deviating prism 333 along the X-Z plane is an isosceles right triangle, so light cast into the prism is shifted in the X direction, and reversed and emitted in the opposite direction.

Light in the present variation behaves as follows. The light cast from the introducing single mode optical fiber 302e is made generally parallel at the first GRIN lens 332a, passes through the glass block 327, and then is subjected to direction reversal in the −Z direction by the optical path deviating prism 333 and also receives a shift in the X-axial direction.

The light emerging from the optical path deviating prism 333 passes through the same glass block 327 again, is converged by the second GRIN lens 332b, and is taken into the extracting single mode optical fiber 302f.

The optical path length is changed by the glass block 327 rotating on an axis which is parallel to the X-axis. In the present embodiment, the light passes through the glass block 327 having parallel planes an even number of times, so the light returning to the single mode optical fiber 302f can be made to be stationary in position even when the glass block 327 rotates.

Also, the present variation only uses one glass block 327, and there is no need to match the phase of two glass blocks 327a and 327b in opposite directions as with the eleventh embodiment, which is advantageous since the control of the rotating mechanism can be simplified.

With the present variation, the light passes twice through the glass block 327 which acts to change the optical path length, which is the same number of times as the eleventh embodiment. Accordingly, in the event that the glass block 327 used in the present variation has the same refractive index and size as the glass block used in the eleventh embodiment, the difference in the optical path length is the same as that of the eleventh embodiment.

Though normal positive lenses may be used instead of the GRIN lenses 332a and 332b used as the collimator lens and converging lens in the present embodiment, relatively small diameter items are being manufactured, such as SELFOC product name) manufactured by Nippon Sheet Glass Co., Ltd. so the optical system can be reduced in size by using this.

Also, a prism 333 with an isosceles right triangle cross-section is used in the variation as the optical path deviating element, but other optical devices such as a roof mirror may be used for the optical path deviating element, so long as the position of the incident light is shifted, and reversed and emitted in the opposite direction.

Next, a second variation of the eleventh embodiment will be described with reference to FIGS. 48A and 48B. With the second variation in FIGS. 48A and 48B, the only thing that has been changed from the eleventh embodiment is the variable-length optical path optical system, and the other unshown members are the same as the tenth embodiment, including the interferometer.

FIG. 48A is a diagram viewing the variable-length optical path optical system from the Y-axial direction and FIG. 48B from the X-axial direction, with the optical axis of the single mode optical fibers 302e and 302f as the Z-axis.

The variable-length optical path optical system according to the present embodiment is formed of an introducing single mode optical fiber 302e for guiding light from the first coupler 303a (see FIG. 44) to the variable-length optical path optical system 324, a first GRIN lens 332a serving as a collimator lens, a glass block 327 with a square cross-section serving as an optical element having mutually parallel planes, first, second, and third optical path deviating prisms 333a, 333b, and 333c serving as three optical path deviating optical elements which shift the position of the incident light and emit the light in the opposite direction, a second GRIN lens serving as a converging lens, and an extracting single mode optical fiber 302f for extracting light. The glass block 327 rotates on an axis which is parallel to the X-axis.

The cross-sectional forms of the optical path deviating prisms 333a, 333b, and 333c along the X-Z planes are isosceles right triangles, so light cast into the prisms is shifted in the X direction, and reversed and emitted in the opposite direction.

Light in the present variation behaves as follows. The light cast from the introducing single mode optical fiber 302e is made generally parallel at the first GRIN lens 332a, passes through the glass block 327, and then is subjected to direction reversal in the –Z direction by the first optical path deviating prism 333a and also receives a shift in the X-axial direction.

The light emerging from the first optical path deviating prism 333a passes through the same glass block 327 again, and then is subjected to direction reversal in the Z direction by the second optical path deviating prism 333b and also receives a shift in the X-axial direction. The light emerging from the second optical path deviating prism 333b passes through the same glass block 327 again, and then is subjected to direction reversal in the Z direction by the third optical path deviating prism 333c and also receives a shift in the X-axial direction, and then passes through the same glass block 327 again.

Finally, the light is converged by the second GRIN lens 332b, and is taken into the extracting single mode optical fiber 302f.

The optical path length is changed by the glass block 327 rotating on an axis which is parallel to the X-axis.

Also, with the present embodiment, the light passes through the glass block 327 having parallel planes an even number of times, so the light returning to the single mode optical fiber 302f can be made to be stationary in position even when the glass block 327 rotates.

Also, according to the first variation, the light emitted from the single mode optical fiber 302e and returning thereof only passes twice through the glass block 327 capable of changing the optical path length, but the light passes through the glass block 327 four times with the present embodiment, so in the event that a glass block 327 with the same refractive index and size as the first variation is used, the difference in optical path length is twice that of the first variation.

Thus, the scanning range of the optical path length can be expanded without increasing the size of the glass block 327, by passing the light through the glass block 327 multiple time using the optical path deviating prisms 333a, 333b, and 333c.

The solid line B in FIG. 47 illustrates the optical path length difference over time, while the glass block 327 with a refractive index of 1.8 and a thickness (the length of one side of the cross-sectional square) of 10 is being rotated at a cycle T. It can be understood that the optical path length difference is twice that of the first variation.

Also, prisms 333a, 333b, and 333c with isosceles right triangle cross-sections are used in the variation as the optical path deviating element, but other optical devices such as a roof mirror may be used for the optical path deviating element, so long as the position of the incident light is shifted, and reversed and emitted in the opposite direction.

Next, a third variation of the eleventh embodiment will be described with reference to FIGS. 49A and 49B.

With the third variation in FIGS. 49A and 49B, the only thing that has been changed from the eleventh embodiment is the variable-length optical path optical system, and the other unshown members are the same as the tenth embodiment, including the interferometer.

FIG. 49A is a diagram viewing the variable-length optical path optical system from the Y-axial direction and FIG. 49B from the X-axial direction, with the optical axis of the single mode optical fibers 302e and 302f as the Z-axis.

The variable-length optical path optical system according to the present variation is formed of an introducing single mode optical fiber 302e for guiding light from the first coupler 303a (see FIG. 44) to the variable-length optical path optical system 324, a first GRIN lens serving as a collimator lens, a second GRIN lens serving as a converging lens, an extracting single mode optical fiber 302f for extracting light, a variable-length optical path optical element group 330 made up of glass blocks 327a and 327b, and an optical path deviating element 335 which shifts the position of the incident light and emits the light in the opposite direction.

The variable-length optical path optical element group 330 is comprised of a first glass block 327a serving as a first optical element, and a second glass block 327b, serving as a second optical element. The first glass block 327a and second glass block 327b each have square cross-sections on the X-Z plane, with exactly the same refractive index and form.

The glass blocks 327a and 327b of the variable-length optical path optical element group 330 are configured to be rotated in mutually opposing directions at the same angle.

The optical path deviating element 335 is configured of an optical path deviating single mode optical fiber 334, a third GRIN lens 332c serving as an optical path deviating element converging lens for converging light to the deviating single mode optical fiber 334, and a fourth GRIN lens 332d serving as an optical path deviating element collimating lens for making the light emitted from the deviating single mode optical fiber 334 to be generally parallel.

Also, the deviating single mode optical fiber 334 has the incident side end plane and the emitting side end plane thereof arrayed parallel in the X-direction so as to face in the same direction, so the optical path deviating element 335 acts to shift the light cast into the optical path deviating single mode optical fiber 334 in the X-direction and also reverse the direction thereof and emit the light.

Light in the present variation behaves as follows. The light cast from the introducing single mode optical fiber 302e is made generally parallel at the first GRIN lens 332a, passes through the variable-length optical path optical element group 330, and then is subjected to direction reversal in the –Z direction by the optical path deviating element 335 and also receives a shift in the X-axial direction. The light emerging from the optical path deviating element 335 passes through the same variable-length optical path optical element group 330 again, and then is converged by the second GRIN lens 332b, and taken into the extracting single mode optical fiber 302f.

The glass blocks 327a and 327b of the variable-length optical path optical element group 330 are configured to be rotated in mutually opposing directions at the same angle, but the light emitted from the introducing single mode optical fiber 302e reaching the optical path deviating single mode optical fiber 334 and the extracting single mode optical fiber 302f has passed through the glass blocks 327a and 327b an even number of times, so the converging position of light does not change, even when the glass blocks 327a and 327b rotate.

According to the present variation, the optical path length difference over time involves the light being passed through the glass blocks four times while the glass blocks 327 with a refractive index of 1.8 and a thickness (the length of one side of the cross-sectional square) of 10 are being rotated at a cycle T. It can be understood that the optical path length difference is the same as that of the second variation.

According to the present variation as well, the scanning range of the optical path length can be expanded by passing the light throughout the same glass blocks 327a and 327b multiple times, as with the second embodiment. Also, the optical system can be reduced in size, by using the GRIN lenses 332a through 332d.

Also, with the present embodiment, the third GRIN lens 332c serving as the converging lens for the optical path deviating element 335 and the fourth GRIN lens 332d serving as a collimating lens for the optical path deviating element is on the side with regard to the variable-length optical path optical element group 330, but an arrangement wherein the third GRIN lens 332c serving as the converging lens for the incident side of the optical path deviating single mode optical fiber 334 for the optical path deviating element 335 and the optical path deviating element 335, and the fourth GRIN lens 332d serving as a collimating lens for the emitting side of the optical path deviating element 335 and the optical path deviating element are provided on opposite sides with the variable-length optical path optical element group 330 introduced therebetween as shown in FIGS. 50A and 50B yields the same operations as the arrangement shown in FIGS. 50A and 50B.

Next, a fifth variation of the eleventh embodiment will be described with reference to FIGS. 51A and 51B.

With the fifth variation in FIGS. 51A and 51B, the only thing that has been changed from the eleventh embodiment is the variable-length optical path optical system, and the other unshown members are the same as the tenth embodiment, including the interferometer.

FIG. 51A is a diagram viewing the variable-length optical path optical system from the Y-axial direction and FIG. 51B from the X-axial direction, with the optical axis of the single mode optical fibers 302e and 302f as the Z-axis.

The variable-length optical path optical system according to the present variation is formed of an introducing single mode optical fiber 302e for guiding light from the first coupler 303a (see FIG. 44) to the variable-length optical path optical system 324, a first GRIN lens serving as a collimator lens, a second GRIN lens serving as a converging lens, an extracting single mode optical fiber 302f for extracting light, a variable-length optical path optical element group 330 made up of glass blocks 327a and 327b, and two optical path deviating elements 335a and 335b which shift the position of the incident light and emit the light in the opposite direction.

The variable-length optical path optical element group 330 is comprised of a first glass block 327a serving as a first optical element, and a second glass block 327b, serving as a second optical element. The first glass block 327a and second glass block 327b each have true hexagon cross-sections on the X-Z plane, with the same refractive index and form.

The glass blocks 327a and 327b of the variable-length optical path optical element group 330 are configured to be rotated in mutually opposing directions at the same angle.

The first optical path deviating element 335a is configured of a third GRIN lens 332c serving as an optical path deviating element converging lens for converging light to a deviating single mode optical fiber 334a, and a fourth GRIN lens 332d serving as an optical path deviating element collimating lens for making the light emitted from the deviating single mode optical fiber 334a to be generally parallel.

Also, the deviating single mode optical fiber 334a has the incident side end plane and the emitting side end plane thereof arrayed parallel in the X-direction so as to face in the same direction, so the first optical path deviating element 335a acts to shift the light cast into the optical path deviating single mode optical fiber 334a in the X-direction and also reverse the direction thereof and emit the light.

The second optical path deviating element 335b is configured of a fifth GRIN lens 332e serving as an optical path deviating element converging lens for converging light to a deviating single mode optical fiber 334b, and a sixth GRIN lens 332f serving as a serving as an optical path deviating element collimating lens for making the light emitted from the deviating single mode optical fiber 334b to be generally parallel.

Also, the deviating single mode optical fiber 334b has the incident side end plane and the emitting side end plane thereof arrayed parallel in the X-direction so as to face in the same direction, so the second optical path deviating element 335b acts to shift the light cast into the optical path deviating single mode optical fiber 334a in the X-direction and also reverse the direction thereof and emit the light.

Light in the present variation behaves as follows. The light cast from the introducing single mode optical fiber 302e is made generally parallel at the first GRIN lens 332a, passes through the variable-length optical path optical element group 330, and then is subjected to direction reversal in the −Z direction by the first optical path deviating element 335a and also receives a shift in the X-axial direction.

The light emerging from the first optical path deviating element 335a passes through the same variable-length optical path optical element group 330 again, and then is subjected to direction reversal in the Z direction by the second optical path deviating element 335b and also receives a shift in the X-axial direction. The light then passes through the same variable-length optical path optical element group 330 again, and is converged by the second GRIN lens 332b, and taken into the extracting single mode optical fiber 302f.

Figure 52:
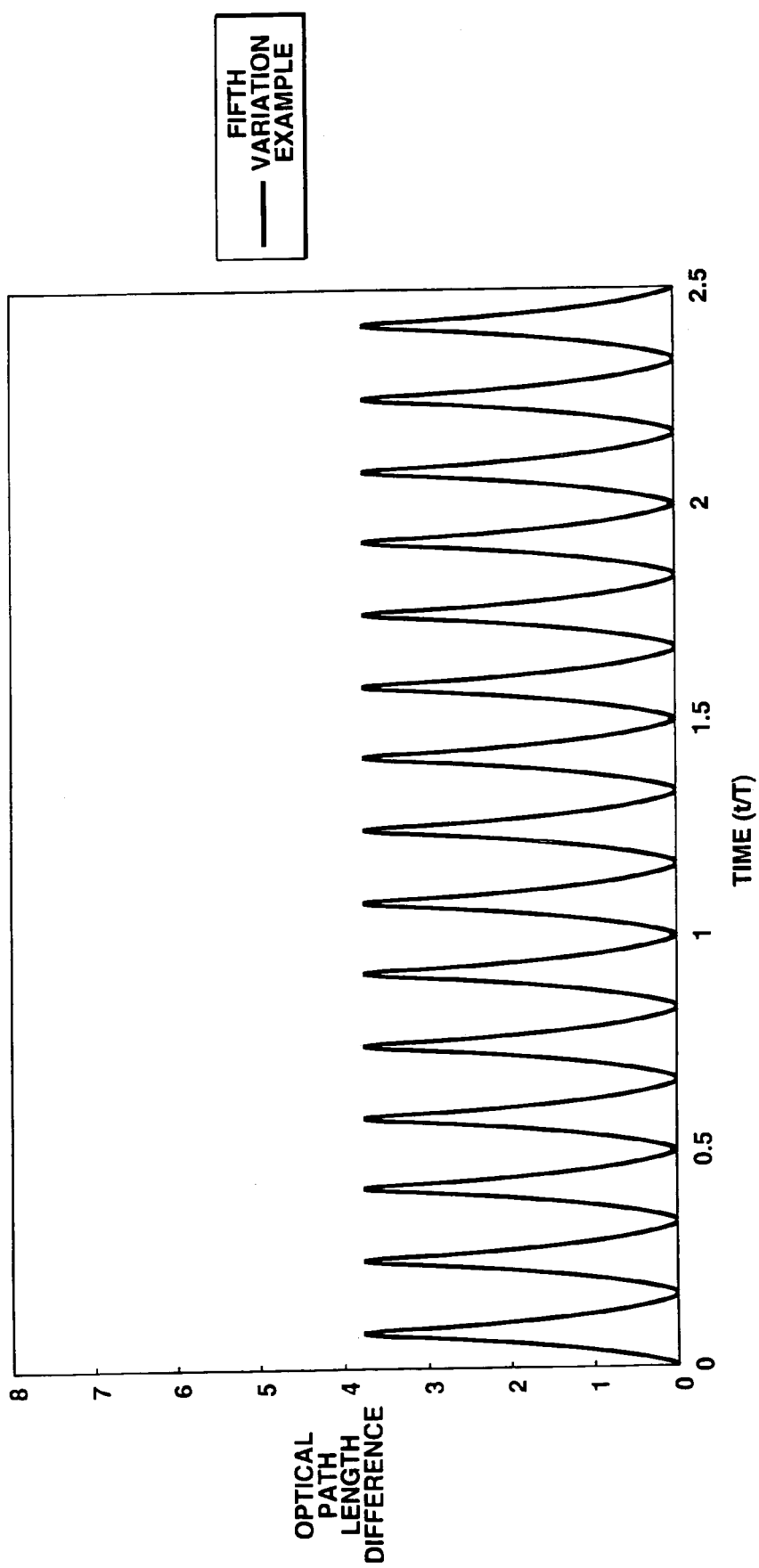
FIG. 52 is a diagram illustrating time-change of the optical path length in the fifth variation example.

FIG. 52 illustrates the optical path length difference over time wherein the glass blocks with a refractive index of 1.8 and a thickness (the distance between mutually parallel planes) of 10 are rotated at a cycle T.

Change in the optical path length is performed by the glass blocks 327a and 327b of the variable-length optical path optical element group 330 rotating in mutually opposing directions at the same angle; but the light emitted from the introducing single mode optical fiber 302e reaching the ends (both incident and emerging) of the optical path deviating single mode optical fibers 334a and 334b and the extracting single mode optical fiber 302f, has passed through the glass blocks 327a and 327b an even number of times, so the converging position of light does not change, even when the glass blocks 327a and 327b rotate. According to the present variation, the cross-sections of the glass blocks 327a and 327b are true hexagons, so reciprocal scanning is performed for six round trips each time the glass blocks 327a and 327b rotate once.

In this way, increasing the number of polygon apexes of the cross-sectional forms of the glass blocks 327a and 327b from a square to a polygon, octagon, and so forth, allows high-speed scanning to be performed even in the event that the number of rotations of the glass blocks 327a and 327b are the same. However, increasing the number of polygon apexes narrows the scanning width, so a great number of optical path deviating elements 335a, 335b, are used to increase the number of times passing through the variable-length optical path optical element group 330, thereby widening the scanning width.

Incidentally, while the description of the above tenth embodiment through the fifth variation of the eleventh embodiment has involved optical elements having at least one pair of parallel planes all being formed of glass, but the present invention is by no means restricted to glass; rather, any material capable of transmitting and refracting light such as optical plastics or the like may be used, and further, it is needless to say that the variable-length optical path optical system is not restricted to the reference light side and also may be provided to the signal light side, as well.

Using the variable-length optical path optical system according to the above tenth embodiment through the fifth variation of the eleventh embodiment realizes a variable-length optical path optical system with high speeds, a wide scanning area, and with little change in light intensity, thereby providing an optical imaging apparatus enabling tomogram observation of the esophagus, stomach, intestines, etc., as moving pictures with excellent quality.

Figure 53:
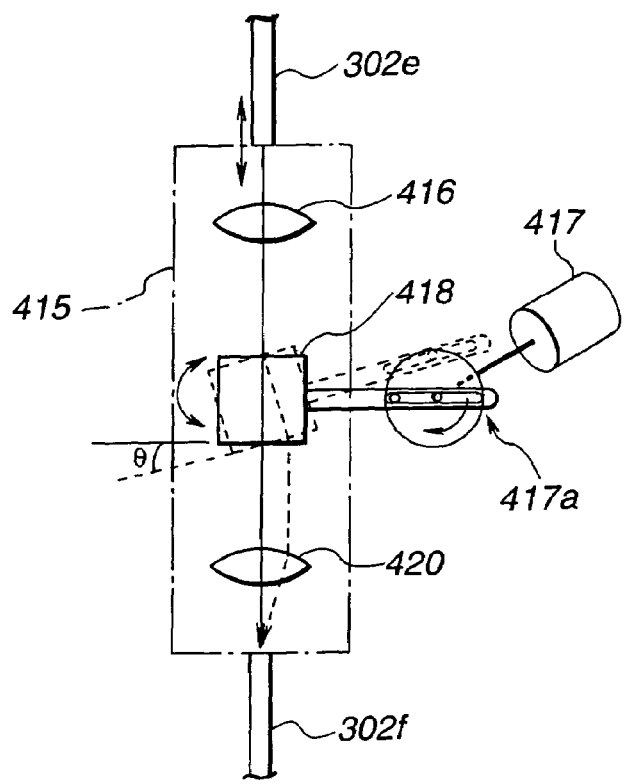
FIG. 53 is a configuration diagram illustrating the variable-length optical path mechanism acquiring to a twelfth embodiment of the present invention.

Next, a twelfth embodiment of the present invention will be described with reference to FIG. 53. FIG. 53 illustrates a variable-length optical path optical system 415 according to the twelfth embodiment of the present invention. This variable-length optical path optical system 415 is used instead of the variable-length optical path optical system 324 in the optical imaging apparatus shown in FIG. 44, for example.

Reference light from the first optical coupler 303a is guided to the variable-length optical path optical system 415 through the fifth single mode optical fiber 302e.

The variable-length optical path optical system 415 is comprised of a lens which forms parallel light out of the light emitted from the end of the fifth single mode optical fiber 302e, a parallel plate prism 418 with a square cross-section which varies the optical path length of the parallel light via the lens 416 by means of turning within a certain angle range, and a converging lens 420 for converging the light from the parallel plate prism 418 to the incident end of the sixth single mode optical fiber 302f.

The actuator is controlled by an unshown control device. Also, the parallel plate prism 418 is not restricted to a square cross-section, but may have a rectangular cross-section instead.

At the variable-length optical path optical system 415, the angle of the parallel plate prism 418 is changed by turning within a certain angle range by the actuator 417, thereby causing interference with reflected light at a depth position in the organism tissue of the same value as this optical path length, with reflection light at other depth portions being non-interfering.

The variable-length optical path optical system 415 forms parallel light out of the light emitted from the end of the fifth single mode optical fiber 302e with the lens 416, varies the optical path length of the parallel light via the lens 416 with the parallel plate prism 418 being turned within a certain angle range by the actuator 417, and converges the light from the parallel plate prism 418 to the incident end of the sixth single mode optical fiber 302 with the converging lens 420.

With the variable-length optical path optical system 415, the parallel plate prism 418 is reciprocally turned (oscillated) within a certain angle range at a frequency of several hundred Hz, by the actuator 417.

As shown in FIG. 53 for example, the actuator 417 and parallel plate prism 418 are lined by a cam mechanism 417a so that the parallel plate prism 418 can be reciprocally turned (oscillated), such that rotations of the actuator 417 causes reciprocal turning (oscillating) of the parallel plate prism 418.

With the parallel plate prism 418, the length of the optical path changes according to the angle θ of reciprocal turning (oscillating) according to Expression (2), as described earlier.

For example, in the event that the light is guided to the parallel plate prism 418 perpendicularly and the optical path length is at its shortest (solid line in FIG. 53), the optical path length increases at the variable-length optical path optical system 415 as the guided light inclines away from perpendicular (dotted line in FIG. 53), and the interference position with the measurement light fluctuates. That is, the position from which reflection is obtained from the organism tissue which is the subject (i.e., the depth) fluctuates.

Incidentally, regarding adjusting of the interference position, adjustment is performed by moving the position of the emitting end of the tip end side of the fifth single mode optical fiber 302e for casting light into the variable-length optical path optical system 415.

At the second coupler portion 303b, there is interference between the reference light and the signal light (measurement light), and the reference light and the signal light of differing phases that have exhibited interference are detected with the first and second detectors 306g and 306h, and the interference intensity is obtained from the differential detection thereof.

This interference intensity is processed by an unshown image processing device, and synchronized with the angle information of the parallel plate prism 418 of the variable-length optical path optical system 415, thereby displaying a two-dimensional optical tomogram on the monitor.

Thus, according to the present embodiment, the optical path length changing means of the variable-length optical path optical system 415 is formed of a lightweight parallel plate prism 418, thereby enabling the parallel plate prism 418 to be reciprocally driven by the actuator 417 within the certain angle range θ at a frequency of several hundred Hz, almost 1 KHz, thereby providing detection data to the image processing device at high speeds compared with conventional arrangement which we are only capable of preparing detection data at several tens of Hz, consequently greatly improving the image reproducing speed of image processing devices capable of organism diagnosis.

Incidentally, though the present embodiment has been described as a parallel plate prism 418 with a square cross-section, being reciprocally driven by the actuator 417 within the certain angle range θ at a frequency of several hundred Hz, the present invention is not restricted to this arrangement; rather, as a first variation example of the variable-length optical path optical system 415, the parallel plate prism 418 may be rotated in the same direction, and in the case the rotational speed can be raised to several KHz, so the image reproducing speed can be increased to the video rate level, allowing the two-dimensional optical tomography image to be displayed on the monitor in real-time.

Figure 54:
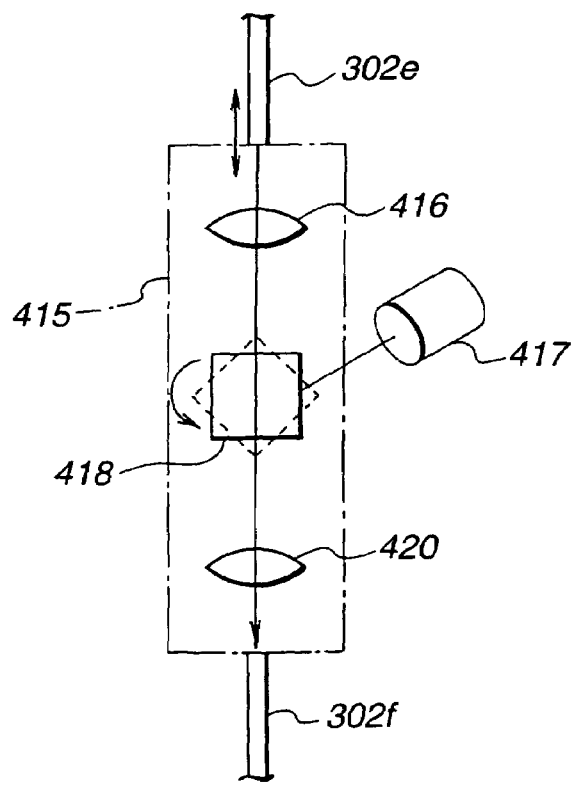
FIG. 54 is a configuration diagram illustrating the variable-length optical path mechanism shown in FIG. 53 acquiring to a first variation example.

However, in the event that the parallel plate prism 418 is rotated in the same direction, as shown in FIG. 54, the optical axis of the incident reference light does not enter the parallel plate prism 418 when positioned at the corner thereof, so the processing of this position is excluded by the image processing device.

Figure 55:
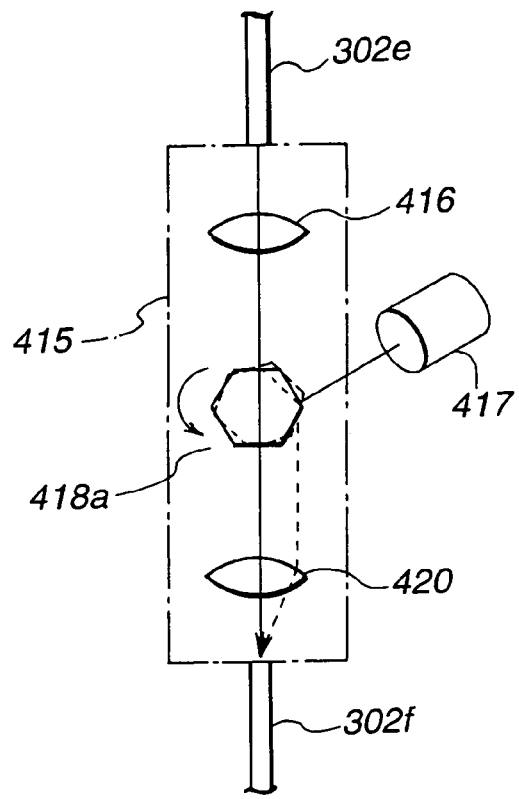
FIG. 55 is a configuration diagram illustrating the variable-length optical path mechanism shown in FIG. 53 acquiring to a second variation example.

As a second variation example of the variable-length optical path optical system 415, the parallel plate prism may be a parallel plate prism 418a with a hexagon cross-section which is rotated in the same direction as shown in FIG. 55, and in this case also, the rotational speed can be raised to several KHz, so the image reproducing speed can be further increased to the video rate level, allowing the two-dimensional optical tomography image to be displayed on the monitor in real-time.

However, in this case as well, the optical axis of the incident reference light does not enter the parallel plate prism 418a when positioned at the corner thereof, so the processing of this position is excluded by the image processing device.

Figure 56:
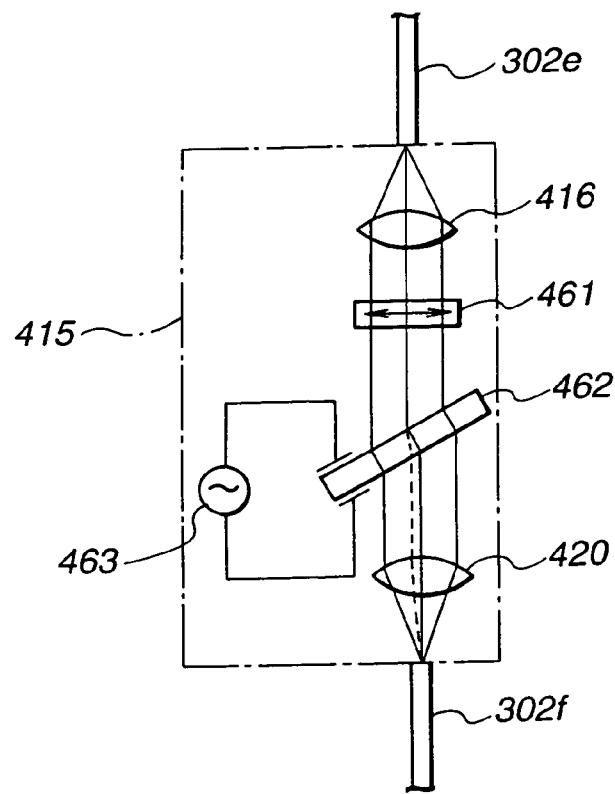
FIG. 56 is a configuration diagram illustrating the variable-length optical path mechanism shown in FIG. 53 acquiring to a third variation example.

As a third variation example of the variable-length optical path optical system 415, as shown in FIG. 56, the parallel plate prism may be replaced with a polarizing plate 461 which changes the incident reference light into linearly polarized light, a plate-shaped liquid crystal device 462 formed of pneumatic liquid crystal for varying the optical path length of the incident reference light, and a liquid crystal driving unit 463 for driving the liquid crystal device 462 at high-frequency driving signal voltage.

In this case, the refraction index n of the liquid crystal device 462 can be continuously changed around 0.3, e.g., n=1.5 to 1.8, by application of voltage from the liquid crystal driving unit 463. Such changing of the refraction index n shifts light as shown by the broken line in FIG. 56, thereby changing the optical path length. Incidentally, the amount of change is represented in the above-described Expression (2).

Also, the above description involved providing the variable-length optical path optical system 415 to the optical path system for reference light, but this may be provided to the optical path system for measuring light.

What is claimed is:

1. An optical imaging apparatus having an optical scanning probe configured to irradiate low-coherence light onto a subject and to perform photo-reception of light scattered at the subject, and an observation device adapted to construct a cross-section image of the subject, based on information from the light received through said optical scanning probe, having said optical scanning probe detachably connected thereto, said optical imaging apparatus comprising:

an optical scanning probe comprising:
a sheath, a greater portion thereof being formed of a flexible resin tube with at least a tip thereof being formed of a material with good light transmittance, and the tip thereof not being opened;
a housing provided to a base end of the sheath, and a mounting structure adapted to mount the housing to said observation device;
a flexible pipe member provided rotatably within said sheath, around a longitudinal axis thereof;
a rotational force transmitting member provided to a base portion of said pipe member;
a rotation holding structure adapted to hold said rotational force transmitting member rotatably to said housing;
a fiber comprised of a single mode fiber provided within said flexible pipe member, with a tip portion thereof being fixed to the tip of said pipe member, such that the light cast from a low-coherence light source is cast into a base end thereof;
a lens for converging light cast from said fiber provided to said fiber tip; and
a cast light path changing member fixed to said lens and adapted to change the optical path of the cast light;
a fiber end fixing member provided to the base end of said fiber; and
an elastic structure provided between said fiber end fixing member and said rotational force transmitting member; and
an observation device, comprising:
a rotational driving device configured and arranged to provide rotational force to said rotational force transmitting member of said optical probe; and
an optical connecting member adapted to connect said fiber of said optical probe with said observation device to send said low-coherence light to said fiber and to receive the light scattered at the subject from said fiber,
wherein, at the time of connecting said optical probe and said observation device by said mounting structure, said fiber end fixing member comes into close contact with said optical connecting member due to the elastic structure of said optical probe, thereby performing optical connection, and any of said fiber end fixing member, elastic member, and rotational force transmitting member has a gap enabling parallel movement of mutual rotational axes, in a diameter direction of the rotational axes.

2. An optical imaging apparatus according to claim 1, comprising a bearing between any of said fiber end fixing member, elastic structure, and rotational force transmitting member, such that mutual rotational axes rotate with an angle.

3. An optical imaging apparatus according to claim 1 or claim 2, wherein said elastic structure comprises an elastic member and a holding member configured to hold the elastic member.

4. An optical imaging apparatus according to claim 2, wherein said bearing is a spherical bearing.

5. An optical imaging apparatus according to claim 2, wherein said bearing comprises a tapered plane and a curved plane which meet.

6. An optical imaging apparatus according to claim 1 or claim 2, further comprising a rotation restricting member adapted to prevent a rotational offset exceeding a certain amount from occurring between said rotational force transmitting member and said fiber end fixing member.

7. An optical imaging apparatus, comprising:
  an optical scanning probe, comprising:
    a sheath with at least a tip thereof being formed of a material with good light transmittance;
    a mounting structure covered by a connector case provided at a base of said sheath;
    a pipe member provided within said sheath so as to be rotatable around an axis in the longitudinal direction;
    a rotational force transmitting member provided at a base portion of said pipe member;
    a rotational holding structure configured and arranged to rotatably hold said rotational force transmitting member within said connector case;
    a first light guiding member provided within said pipe member, such that light emitted from a low-coherence light source is cast into a base portion thereof;
    an optical scanning direction changing structure provided at the tip portion of said first light guiding member, to emit low-coherence light to a subject side, and to perform photo-reception of scattered light from the subject and to guide the light to the base portion side of said first light guiding member;
    a base portion fixing member provided at the base portion of said first light guiding member; and
    an elastic structure provided between said base portion fixing member and said rotational force transmitting member, to press said base portion fixing member against the base side thereof in an elastic manner; and
  an observation device, comprising:
    a low-coherence light source configured and arranged to generate said low-coherence light;
    a second light guiding member provided within said observation device, guiding said low-coherence light emitted from the low-coherence light source;
    an optical connecting member to which said mounting structure is detachably connected, adapted to connect the base portion of said first light guiding member with an end portion of said second light guiding member such that the low-coherence light guided by said second light guiding member is emitted to the base portion of said first light guiding member, and the scattered light from the subject is cast from said first light guiding member into the end portion of said second light guiding member; and
  a rotational driving device for applying a rotational force to said rotational force transmitting member in the state that said mounting means is connected;
  wherein any of said base portion fixing member, said elastic structure and said rotational force transmitting member has a gap enabling parallel movement of mutual rotational axes in the diameter direction of the rotational axes, and in the state that the base portion of said optical scanning probe is mounted to said observation device by said mounting structure, said elastic structure presses said base portion fixing member against said optical connecting member, thereby performing optical connection.

* * * * *